US008188239B2

(12) United States Patent
Hansen et al.

(10) Patent No.: US 8,188,239 B2
(45) Date of Patent: *May 29, 2012

(54) MULTIVALENT CARRIERS OF BI-SPECIFIC ANTIBODIES

(75) Inventors: Hans J. Hansen, Picayune, MS (US); William J. McBride, Boonton, NJ (US); Zhengxing Qu, Warren, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/089,645

(22) Filed: Apr. 19, 2011

(65) Prior Publication Data

US 2011/0223645 A1 Sep. 15, 2011

Related U.S. Application Data

(60) Continuation of application No. 12/436,352, filed on May 6, 2009, now Pat. No. 7,951,921, which is a division of application No. 10/882,151, filed on Jul. 1, 2004, now abandoned.

(60) Provisional application No. 60/483,832, filed on Jul. 1, 2003.

(51) Int. Cl.
*C07K 17/00* (2006.01)

(52) U.S. Cl. ............... 530/391.1; 530/387.1; 530/387.3

(58) Field of Classification Search ............... 530/387.1, 530/387.3, 391.1
See application file for complete search history.

(56) References Cited

U.S. PATENT DOCUMENTS

| | | | |
|---|---|---|---|
| 5,256,395 A | 10/1993 | Barbet et al. | |
| 5,530,101 A | 6/1996 | Queen et al. | |
| 5,618,920 A | 4/1997 | Robinson et al. | |
| 5,789,554 A | 8/1998 | Leung et al. | |
| 5,874,540 A | 2/1999 | Hansen et al. | |
| 6,217,869 B1 | 4/2001 | Meyer et al. | |
| 6,451,980 B1 | 9/2002 | Khaw et al. | |
| 7,951,921 B2 * | 5/2011 | Hansen et al. | 530/391.1 |
| 2002/0009444 A1 | 1/2002 | Grillo-Lopez | |
| 2002/0076406 A1 | 6/2002 | Leung | |
| 2003/0113333 A1 | 6/2003 | Rossi et al. | |
| 2003/0198595 A1 | 10/2003 | Goldenberg et al. | |
| 2004/0001825 A1 | 1/2004 | Govindan et al. | |
| 2004/0018557 A1 | 1/2004 | Qu et al. | |
| 2004/0166115 A1 | 8/2004 | Griffiths et al. | |

FOREIGN PATENT DOCUMENTS

| | | |
|---|---|---|
| WO | 94/11026 | 5/1994 |
| WO | 95/09917 | 4/1995 |
| WO | 99/66951 | 12/1999 |

OTHER PUBLICATIONS

Bardies et al., "Bispecific Antibody and Iodine-131-Labeled Bivalent Hapten Dosimetry in Patients with Medullary Thyroid or Small-Cell Lung Cancer", J. Nucl. Med. 37(11):1853-1859 (1996).

Behr et al., "Variables Influencing Tumor Dosimetry in Radioimmunotherapy of CEA-Expressing Cancers with Anti-CEA and Antimucin Monoclonal Antibodies", J. Nucl. Med. 38(3):409-418 (1997).

Blumenthal et al., "Carcinoembryonic antigen antibody inhibits lung metastasis and augments chemotherapy in a human colonic carcinoma xenograft", Cancer Immunol. Immunother. 54(4):315-327 (2005).

Boerman et al., "Pretargeting of Renal Cell Carcinoma: Improved Tumor Targeting with a Bivalent Chelate", Cancer Res. 59:4400-4405 (1999).

Coloma et al., "Design and Production of Novel Tetravalent Bispecific Antibodies", Nature Biotechnology, vol. 15, No. 2, p. 159-163 (1997).

Hornick et al., "Single Amino Acid Substitution in the Fc Region of Chimeric TNT-3 Antibody Accelerates Clearance and Improves Immunoscintigraphy of Solid Tumors", J. Nucl. Med. 41(2):355-362 (2000).

Karacay et al., "Pretargeting for Cancer Radioimmunotherapy With Bispecific Antibodies: Role of the Bispecific Antibody's Valency for the Tumor Target Antigen", Bioconjugate Chem. 2002, vol. 13, No. 5, p. 1054-1070.

Karacay et al., "Experimental Pretargeting Studies of Cancer with a Humanized anti-CEA x Murine anti-[In-DTPA] Bispecific Antibody Construct and a 99mTc-/188Re-Labeled Peptide", Bioconjugate Chem. 11:842-854 (2000).

Kipriyanov et al., "Affinity enhancement of a recombinant antibody: formation of complexes with multiple valency by a single-chain Fv fragment-core streptavidin fusion", Protein Eng. 1996 Feb;9(2):203-11.

Le Gall et al., "Di-, tri- and tetrameric single chain Fv antibody fragments against human CD19: effect of valency on cell binding", FEBS Lett. Jun. 18, 1999;453(1-2):164-8.

Lu et al., "Fab-scFv Fusion Protein: an Efficient Approach to Production of Bispecific Antibody Fragments", J. Immunol. Methods, Sep. 15, 2002, vol. 267, No. 2, p. 213-226.

Morel et al., "Recognition of imidazole and histamine derivatives by monoclonal antibodies", Mol. Immunol. 27 (10):995-1000 (1990).

Paul, W. (ed) Fundamental Immunology, Chapter 8, p. 242, Raven Press, NY (1993).

Willuda et al., "Tumor targeting of mono-, di-, and tetravalent anti-p185(HER-2) miniantibodies multimerized by self-associating peptides", J Biol Chem. Apr. 27, 2001;276(17):14385-92.

* cited by examiner

*Primary Examiner* — Misook Yu
*Assistant Examiner* — Brad Duffy
(74) *Attorney, Agent, or Firm* — Richard A. Nakashima

(57) ABSTRACT

Provided herein are targetable constructs that are multivalent carriers of bi-specific antibodies, i.e., each molecule of a targetable construct can serve as a carrier of two or more bi-specific antibodies. Also provided are targetable complexes formed by the association of a targetable construct with two or more bi-specific antibodies. The targetable constructs and targetable complexes of the invention are incorporated into biosensors, kits and pharmaceutical compositions, and are used in a variety of therapeutic and other methods.

14 Claims, 9 Drawing Sheets

1:1 hMN-14IgG$^{(I253A)}$-(734scFv)$_2$/Tc-99m IMP 192

| | Name | Retention Time | Area | % Area | Height | Type | Amount | Units | Peak Type | Codes |
|---|---|---|---|---|---|---|---|---|---|---|
| 1 | | 0.382 | 11055 | 0.52 | 1260 | BB | | | Unknown | |
| 2 | | 2.140 | 5816 | 0.27 | 427 | BB | | | Unknown | |
| 3 | | 7.167 | 18513 | 0.87 | 767 | BV | | | Unknown | |
| 4 | | 7.744 | 16150 | 0.76 | 1181 | VV | | | Unknown | |
| 5 | | 8.299 | 145299 | 6.86 | 4660 | VV | | | Unknown | |
| 6 | | 9.563 | 1861902 | 87.89 | 50902 | VB | | | Unknown | |
| 7 | | 10.984 | 5821 | 0.27 | 480 | BB | | | Unknown | |
| 8 | | 14.293 | 17128 | 0.81 | 1036 | BB | | | Unknown | |
| 9 | | 14.861 | 14490 | 0.68 | 784 | BV | | | Unknown | |
| 10 | | 15.363 | 22307 | 1.05 | 1438 | VB | | | Unknown | |

94% Recovery from column

MULTIVALENT CARRIERS OF BI-SPECIFIC ANTIBODIES

RELATED APPLICATIONS

The present application is a continuation of U.S. patent application Ser. No. 12/436,352 (now issued U.S. Pat. No. 7,951,921), filed May 6, 2009, which is a divisional of U.S. patent application Ser. No. 10/882,151 (now abandoned), filed Jul. 1, 2004, which claims priority to provisional U.S. Patent Application Ser. No. 60/483,832, filed Jul. 1, 2003, the contents of which are incorporated herein in their entirety.

FIELD OF THE INVENTION

The invention relates to compounds that are multivalent carriers of bi-specific antibodies (bsAbs), i.e., each molecule of the compound can serve as a carrier of two or more bi-specific antibodies. The invention further relates to complexes formed by the association of a multivalent compound with two or more bi-specific antibodies. In preferred embodiments, the compounds of the invention form complexes that have desirable attributes such as increased affinity, high stability in vitro and/or in vivo, and preferred pharmacokinetics. The compounds and complexes of the invention are useful for therapy and in vitro applications.

BACKGROUND OF THE INVENTION

The following description of the background of the invention is provided simply as an aid in understanding the invention and is not admitted to describe or constitute prior art to the invention.

An approach to cancer therapy and diagnosis involves directing antibodies (Abs) or antibody fragments to disease tissues, wherein the antibody or antibody fragment can target a therapeutic agent to the disease site, i.e., a targeted tissue. A "targeted tissue" is any biological entity (e.g., a system, organ, tissue, cell, organelle, receptor, surface antigen, transmembrane protein, secreted polypeptide, or intracellular component) to which a targetable construct is preferentially delivered. The term "delivered" encompasses being contacted with, bound to, and/or internalized by, a targeted tissue. As used herein, the term "and/or" has the meaning of "and, additionally or alternatively" or "and, in addition to or in the alternative."

In therapeutic aspects of the invention, the targeted tissue is malignant, infected, inflamed (as in certain autoimmune diseased sites), dysfunctional or displaced or ectopic (e.g., infected cells, cancer cells, endometriosis, etc.), or otherwise diseased (e.g., atherosclerosis, ischemia, clots). Antibodies are used to deliver therapeutic agents to the targeted tissue.

The use of a bsAb/low molecular weight (MW) hapten system is not without some limitations. The arm of the bsAb that binds to the low MW hapten must bind with high affinity, since a low MW hapten is desirably one that clears the living system rapidly when not bound by bsAb. The non-bsAb-bound low MW hapten needs to clear the living system rapidly to avoid non-target tissue uptake and retention. Moreover, the therapeutic agent must remain associated with the low MW hapten throughout its application within the bsAb protocol employed.

This application incorporates by reference the entirety of U.S. application Ser. No. 09/337,756, entitled "Use of bi-specific antibodies for pre-targeting diagnosis and therapy", which was filed Jun. 22, 1999.

This application incorporates by reference the entirety of U.S. application Ser. No. 09/382,186, entitled "Use of bi-specific antibodies for pre-targeting diagnosis and therapy", which was filed Aug. 23, 1999.

This application incorporates by reference the entirety of U.S. application Ser. No. 09/823,746, entitled "Production and use of novel peptide-based agents for use with bi-specific antibodies", which was filed Apr. 3, 2001.

This application incorporates by reference the entirety of U.S. Provisional Application Ser. No. 60/361,037, entitled "Bispecific antibody point mutations for enhancing rate of clearance", which was filed Mar. 1, 2002.

This application incorporates by reference the entirety of published PCT Application WO 99/66951 by Hansen et al., entitled "Use of bi-specific antibodies for pre-targeting diagnosis and therapy", which describes some of the reagents used in the Examples herein.

The synthesis of IMP 192 is described in Karacay et al., Experimental pretargeting studies of cancer with a humanized anti-CEA x murine anti-[In-DTPA] bispecific antibody construct and a (99m)Tc-/(188)Re-labeled peptide, *Bioconjug. Chem.* 11:842-854, 2000.

The radiolabeling of Ac-Phe-Lys(-DTPA)-Tyr-Lys(-DTPA)-NH$_2$ (SEQ ID NO:1) with $^{111}$In is described in Boerman et al., Pretargeting of renal cell carcinoma: improved tumor targeting with a bivalent chelate, *Cancer Res.* 59:4400-4405, 1999.

SUMMARY OF THE INVENTION

The present invention provides multimeric targetable complexes that are multivalent and/or polyspecific. The invention further relates to methods of making such complexes, compositions for making such complexes, and methods of using the multimeric targetable complexes of the invention.

Targetable Complexes

The present invention relates to multimeric targetable complexes that are multivalent and/or polyspecific. A non-limiting example of a multimeric, multivalent targetable complex is a tetravalent targetable complex, which comprises (a) a targetable construct and (b) 2 molecules of a bi-specific antibody, each molecule comprising (i) two arms, each of which binds a carrier epitope, and (ii) two arms, each of which is capable of binding a target epitope. The complex is tetravalent because it comprises a total of 4 arms, each of which is capable of binding a target epitope (2 molecules of an antibody that has 2 arms capable of binding the target epitope).

A targetable complex of the invention may be polyspecific, multivalent, or both.

A tetravalent complex is examplary of a multivalent complex and may be a homodimer or a heterodimer.

In a homodimer (e.g., a tetravalent targetable complex of the invention) both of 2 bi-specific antibodies have 2 arms that bind the same target epitope, and 2 arms that bind a carrier epitope. The homodimeric complex is bi-specific because its arms either recognize (a) a carrier epitope or (b) a target epitope, and is tetravalent because it has 4 arms that recognize the target epitope.

A tetravalent targetable complex of the invention has four arms capable of binding a target epitope, and comprises:
  (a) a targetable construct comprising (i) a molecular scaffold and (ii) two pairs of a carrier epitope; and
  (b) two molecules of a bi-specific antibody, each antibody comprising (i) two arms, each arm comprising a binding site for said carrier epitope, and (ii) two arms, each comprising a binding site for said target epitope.

Preferably, a tetravalent complex of the invention has one or more of the following attributes:
(I) the targetable complex has a Kd for said target epitope from about 0.1 nM to about 100 nM,
(II) mixing the targetable construct and the bi-specific antibody at relative concentrations ranging from about $10^{-3}$ to about $10^3$ results in a mixture in which greater than about 75% of the complexes therein have a defined stoichiometry of two molecules of said bi-specific antibody, and one molecule of said targetable construct, and
(III) a pair of carrier epitopes is bound by said bi-specific antibody in a 1:1 ratio.

In a heterodimer (e.g., a targetable complex that is divalent for each of two target epitopes), each of 2 bi-specific antibodies have two arms that bind different target epitopes, and two arms that bind a carrier epitope. The heterodimeric complex is bi-specific (it recognizes two different target epitopes) and divalent for each target epitope because it has four arms, wherein two of said arms recognize a first carrier epitope, and wherein the other two arms recognize a second target epitope.

A targetable complex of the invention that is divalent for each of two target epitopes comprises:
(a) a targetable construct comprising (i) a molecular scaffold and (ii) two pairs of carrier epitopes, wherein the first of said two pairs of carrier epitopes is specifically bound by a first bi-specific antibody, and the second of said two pairs of carrier epitopes is specifically bound by a second bi-specific antibody, wherein the targetable construct forms a targetable complex when combined with
(b) a first bi-specific antibody, the first bi-specific antibody comprising (i) two copies of a first arm comprising a binding site for said carrier epitope, and (ii) two copies of a second arm comprising a binding site for a first target epitope, and
(c) a second bi-specific antibody, the second bi-specific antibody comprising (i) two copies of a first arm comprising a binding site for said carrier epitope, and (ii) two copies of a second arm comprising a binding site for a second target epitope.

Preferably, a targetable complex of the invention that is divalent for each of two target epitopes has one or more of the following attributes:
(I) said targetable complexes have a Kd for said target epitope from about 0.1 nM to about 100 nM,
(II) mixing said targetable construct and said bi-specific antibody at relative concentrations ranging from about $10^{-3}$ to about $10^3$ results in a mixture in which greater than about 75% of the complexes therein have a defined stoichiometry of two molecules of said bi-specific antibody, and one molecule of said targetable construct, and
(III) each pair of carrier epitopes is bound by one of said bi-specific antibodies in a 1:1 ratio.

Both homodimeric and heterodimeric tetrameric complexes are encompassed by targetable complexes that comprise:
(a) a targetable construct comprising (i) a molecular scaffold and (ii) two pairs of carrier epitopes, wherein the first of said two pairs of carrier epitopes is specifically bound by a first bi-specific antibody, and the second of said two pairs of carrier epitopes is specifically bound by a second bi-specific antibody, wherein said targetable construct forms a targetable complex when combined with
(b) a first bi-specific antibody, said first bi-specific antibody comprising (i) two copies of a first arm comprising a binding site for said carrier epitope, and (ii) two copies of a second arm comprising a binding site for a first target epitope, and
(c) a second bi-specific antibody, said second bi-specific antibody comprising (i) two copies of a first arm comprising a binding site for said carrier epitope, and (ii) two copies of a second arm comprising a binding site for a second target epitope;

wherein said first bi-specific antibody and said second bi-specific antibody can be the same or different, said pairs of carrier epitopes can be the same or different, and said target epitopes can be the same or different, and wherein one or more of the following applies:
(I) the targetable complex has a Kd for a target epitope from about 0.1 nM to about 100 nM,
(II) mixing the targetable construct and the bi-specific antibody at relative concentrations ranging from about $10^{-3}$ to about $10^3$ results in a mixture in which greater than about 75% of the complexes therein have a defined stoichiometry of two molecules of the bi-specific antibody, and one molecule of the targetable construct, and
(III) each pair of carrier epitopes is bound by one of said bi-specific antibodies in a 1:1 ratio.

In general, multivalent and/or polyspecific complexes comprise:
a targetable construct comprising a molecular scaffold and X pairs of carrier epitopes, wherein each of said pairs of carrier epitopes is specifically bound by one of X bi-specific antibodies, each bi-specific antibody comprising (a) two copies of a first arm comprising a binding site for a carrier epitope, and (b) two copies of a second arm comprising a binding site for one of Y target epitopes, wherein
(i) X is a whole integer $\geqq 2$,
(ii) Y is a whole integer $>1$,
(iii) said X bi-specific antibodies can be the same or a mixture of different bi-specific antibodies,
(iv) said X pairs of carrier epitopes can be the same or a mixture of different carrier epitopes, and
(v) when Y>2, said Y target epitopes can be the same or a mixture of different target epitopes, and
a pair of carrier epitopes is bound by a bi-specific antibody in a 1:1 ratio.

Targetable Constructs

The present invention relates to multivalent targetable constructs that may be used to form targetable complexes with bi-specific antibodies prior to and/or after administration to a subject. The constructs comprise two or more pairs of carrier epitopes that are bound by an arm of a bi-specific antibody and are thus multivalent constructs.

For tetrameric complexes, a tetravalent (i.e., comprising two pairs of carrier epitopes) targetable construct comprises a molecular scaffold, and two pairs of a carrier epitope, wherein the targetable construct, when combined with a bi-specific antibody comprising (i) two copies of a first arm comprising a binding site for the carrier epitope, and (ii) two copies of a second arm comprising a binding site for a target epitope, forms a targetable complex.

A tetrameric targetable complex of the invention that is divalent for each of two target epitopes comprises a molecular scaffold and two pairs of carrier epitopes, wherein the first pair of carrier epitopes is specifically bound by a first bi-specific antibody, and the second pair of carrier epitopes is specifically bound by a second bi-specific antibody, wherein the targetable construct forms a targetable complex when combined with
(a) a first bi-specific antibody, the first bi-specific antibody comprising (i) two copies of a first arm comprising a binding site for a carrier epitope, and (ii) two copies of a second arm comprising a binding site for a first target epitope, and (b) a second bi-specific antibody, said second bi-specific antibody comprising (i) two copies of a first arm comprising a binding site for said carrier epitope, and (ii) two copies of a second arm comprising a binding site for a second target epitope.

In general, multivalent and/or polyspecific constructs comprise a molecular scaffold and X pairs of carrier epitopes, wherein each of said pairs of carrier epitopes is specifically bound by one of X bi-specific antibodies, each bi-specific antibody comprising (a) two copies of a first arm comprising a binding site for a carrier epitope, and (b) two copies of a second arm comprising a binding site for one of Y target epitopes, wherein (i) X is a whole integer 2, (ii) Y is a whole integer >1, (iii) said X bi-specific antibodies can be the same or a mixture of different bi-specific antibodies, (iv) said X pairs of carrier epitopes can be the same or a mixture of different carrier epitopes, and (v) when Y>2, said Y target epitopes can be the same or a mixture of different target epitopes, and a pair of carrier epitopes is bound by a bi-specific antibody in a 1:1 ratio.

Preferably, a targetable complex formed using a targetable construct of the invention of the invention has one or more of the following attributes:

(a) the targetable complex has a Kd for the target epitope from about 0.1 nM to about 100 nM, and (b) mixing the targetable construct and the bi-specific antibody at relative concentrations ranging from about $10^{-3}$ to about $10^3$ results in a mixture in which greater than about 75% of the complexes therein have a defined stoichiometry of two molecules of the bi-specific antibody, and one molecule of the targetable construct, (c) a pair of carrier epitopes is simultaneously bound by said two copies of a first arm comprising a binding site for said carrier epitope, wherein said two copies of a first arm comprising a binding site for said carrier epitope are part of said bi-specific antibody.

Embodiments

It has been discovered that it is advantageous to prepare and use multimers of polyspecific antibodies, e.g., antibodies that have two or more arms that specifically bind a targetable construct that is capable of carrying one or more therapeutic agents, and two or more arms that bind a targeted tissue. By utilizing this technique, the multimerization of bi-specific antibodies and other polyspecific antibodies, targetable constructs, chelators, metal chelate complexes, therapeutic agents can be varied to accommodate differing applications.

Because a polyspecific antibody must, by definition, specifically bind at least two different targets, a bispecific antibody (bsAb) is the simplest type of polyspecific antibody. Similarly, a multivalent antibody must, by definition, have at least two binding sites for a single target, and a divalent antibody is thus the simplest type of multivalent Abs. Thus, at a minimum, the Abs of the invention are bispecific (i.e., bind 2 different targets) and divalent (comprising 2 copies of an arm that binds a target).

An antibody used in the invention may be a monoclonal antibody, a humanized antibody, a human antibody, a chimeric antibody, a single chain antibody, a camelid antibody, a CDR, a soluble TCR, a fusion protein, a naked antibody, or a fragment of any of the preceding.

The targetable construct may comprise a peptide; a carbohydrate; and/or one or more haptens including but not limited to a chelator or metal-chelate complex. By way of non-limiting example, the chelator may be a hard base chelator for a hard acid cation, and at least one of the chelators is a soft base chelator for a soft acid cation; or a hard base chelator that comprises carboxylate and amine groups. Non-limiting examples of hard base chelators include DTPA, NOTA, DOTA and TETA.

The invention further relates to methods utilizing multivalent and/or polyspecific targetable constructs and complexes. In some embodiments, the targetable construct or complex comprises a biologically active moiety, such as one that initiates, enhances, limits or prevents a biochemical process. A bioactive moiety of the present invention is selected from the group consisting of a drug, a prodrug, an enzyme, a hormone, an immunomodulator, an oligonucleotide; a radionuclide, an image enhancing agent and a toxin. A "biochemical process" is any process that alters any activity or process of a cell, or of a subcellular portion. A subcellular portion may be an organelle, e.g., a mitochondrion, the endoplasmic reticulum, the nucleus, the nucleolus, or the cell membrane and/or a receptor thereon. By way of non-limiting example, a biochemical process may be a signaling cascade, a complement cascade, apoptosis, a biochemical pathway, or one or more reactions that occur in any of the preceding.

A biochemical process comprises one or more reactions. A "reaction" is any response of one or more molecules to being brought into contact with one or more other molecules, or any response of one or molecules to a change in the proximity of one or more other molecules. A chemical reaction, in which a molecule is split into two or more molecules, and/or two or more molecules are reacted with each other to form one or more different molecules, is a non-limiting example of a reaction. A non-covalent association of two or more molecules with each other is another example of a reaction. A transfer of an electron or ion from one molecule to another is another example of reaction. A change in conformation in response to contact with another molecule is another example of a reaction. Intracellular and intercellular translocations of molecules are reactions.

In some embodiments, the targetable constructs and complexes are biologically active not because they comprise a bioactive moiety per se but because the binding of the targetable construct or complex to its targeted tissue initiates, enhances, limits or prevents a biochemical process. For example, in some embodiments, the bi-specific antibodies of the targetable complex may be naked antibodies. A "naked antibody" is, generally, an antibody that lacks the Fc portion of an antibody. The Fc portion of the antibody molecule provides effector functions, such as complement fixation and ADCC (antibody dependent cell cytotoxicity), which set mechanisms into action that may result in cell lysis. However, the Fc portion may nor be required for therapeutic function in every instance, with other mechanisms, such as apoptosis, coming into play.

The targetable constructs and complexes may comprise one or more agents useful for killing or slowing the growth of diseased tissue. By way of non-limiting example, the agent may be a radioactive isotope, particularly the therapeutically useful therapeutic radionuclides set forth herein. The agent may also be a toxin; one or more drugs; and/or one or more prodrugs. By way of non-limiting example, the targetable construct or complex may comprise doxorubicin, CPT-11 or SN38.

One embodiment of the invention involves using compositions and methods of the disclosure in boron neutron capture therapy (BNCT). In BNCT, the targetable constructs comprise boron atoms, in which case the method further comprise the step of irradiating the boron atoms localized at the diseased tissue, thereby effecting BNCT.

Various embodiments of the invention provide pre-targeting methods and compositions using pre-formed targetable complexes of the invention. A targetable complex comprises a multivalent targetable construct, which optionally carries one or more bioactive agents; and one or more pairs of a bi-specific antibody comprising a pair of arms that specifically bind the multivalent targetable construct, and two or more arms that bind a targeted tissue.

A further embodiment of the invention involves a kit comprising the targetable complexes of the invention, which may further comprise one or more compounds selected from the group consisting of one or more radioactive isotopes useful for killing or slowing the growth of diseased tissue, one or more toxins, one or more drugs, and one or more prodrugs.

In a further embodiment, the invention provides compositions and methods for targeting cardiovascular lesions such as atherosclerotic plaques, vascular clots including thrombi and emboli, myocardial infarction, and other organ infarcts.

The invention also provides compositions and methods for targeting metabolic disease, such as amyloid in amyloidosis, as well as a neurodegenerative disease such as Alzheimer's disease.

In a further embodiment, the invention provides compositions and methods for treating a mammal having a hypoplastic, absent, anatomically displaced or ectopic tissue or organ.

In a further embodiment, the invention provides compositions and methods for treating diseases, including, for example, pathogenic diseases, cancer, cardiovascular diseases, neurodegenerative diseases, metabolic diseases, and autoimmune diseases.

In a further embodiment, the invention provides pharmaceutical compositions and kits comprising the compositions of the invention.

In a further embodiment, the invention provides compositions and methods for making a biosensor that may be used to detect substances in samples or in the environment.

In a further embodiment, the invention provides compositions and methods for in vitro immunochemical methods, including but not limited to immunoassays and immunoaffinity purification. In these and other embodiments, the compositions of the invention may be attached to solid supports. Representative solid supports include dipsticks, beads, multititer plates, the interior surface of wells in a multiwell/microtiter plate, and membranes.

In a further embodiment, the invention provides compositions and methods for separating a compound of interest from undesirable substances in a composition. In this embodiment, a targetable construct or complex is attached to a solid support, to which the composition is contacted. A compound of interest or an undesirable substance is bound by the targetable construct or complex that is attached to the solid support. In a further step, the compound of interest or the undesirable substance are separated from each other as either the compound of interest or the undesirable substance is retained by the immobilized targetable construct or complex. The compositions and methods of the invention can be used in a dialysis machine or system, as well as in a manufacturing process.

In addition, the present invention provides a bi-specific antibody having the structure $[IgG_1]$-$[scFv]2$; where the antibody has a pair of heavy chains and a pair of light chains, where each heavy chain has an IgG1 heavy chain and an scFv, and where the scFv is fused to the C-terminus of the IgG1 heavy chain, optionally via a linker peptide. The antibody binding sites formed by the heavy chain and the light chain may specifically bind to an epitope on a targeted tissue. Each of the scFv moieties may specifically bind to a carrier epitope. The IgG1 and/or the scFv molecules may be human, humanized, chimeric, or CDR-grafted. The antibody further contain a bioactive moiety. The bioactive moiety may be, for example, a drug, a prodrug, an enzyme, a hormone, an immunomodulator, an oligonucleotide; a radionuclide, an image enhancing agent and/or a toxin. The bi-specific antibody may be formulated into a pharmaceutical composition.

Specific examples of such bi-specific antibodies include, but are not limited to hMN-14-IgG-(734scFv)$_2$ and hMN-14IgG$^{(I253A)}$-(734scFv)$_2$, hMN-14IgG-(679scFv)$_2$ and hMN-14IgG$^{(I253A)}$-(679scFv)$_2$, hA20-IgG-(734scFv)$_2$ and hA20-IgG$^{(I253A)}$-(734scFv)$_2$, hA20-IgG-(679scFv)$_2$ and hA20-IgG$^{(I253A)}$-(679scFv)$_2$, hLL2-IgG-(734scFv)$_2$ and hLL2-IgG$^{(I253A)}$-(7-34scFv)$_2$, and hLL2-IgG-(679scFv)$_2$ and hLL2-IgG$^{(I253A)}$-(679scFv)$_2$.

The invention further provides a binding complex having a tetravalent binding molecule bound to a targetable construct, where the tetravalent binding molecule has two binding sites for a carrier epitope and two binding sites for a target epitope, and where the targetable construct has a molecular scaffold and at least two carrier epitopes. The targetable construct may have at least two pairs of carrier epitopes and in the complex at least two of the tetravalent binding molecules may be bound to the targetable construct. The targetable construct may contain at least two pairs of different carrier epitopes and in the complex the first tetravalent binding molecule may be bound to one pair of carrier epitopes and a second tetravalent binding molecule may be bound to a second pair of carrier epitopes. The pairs of carrier epitopes may be different epitopes. The first and second tetravalent binding molecules may bind to the same target epitope. The targetable construct may be selected from the group consisting of IMP 246, IMP 156, IMP 192 and IMP 222. The carrier epitope may be a hapten. The carrier epitope may be a chelator, where the chelator optionally is bound to a metal ion. The chelator may be, for example, DTPA, DOTA, benzyl DTPA, NOTA, or TETA. The tetravalent binding molecule may be a bi-specific antibody having the structure $[IgG_1]$-$[scFv]2$, where the antibody has a pair of heavy chains and a pair of light chains, and where each heavy chain has an IgG1 heavy chain and an scFv, where the scFv is fused to the C-terminus of the IgG1 heavy chain, optionally via a linker peptide. In the binding complex the molecular scaffold may be, for example, a peptide or peptide derivative.

In each of these examples, the target epitope may be an antigen associated with, for example, a disease, such as a hyperproliferative disease, pathogenic disease, cancer, cardiovascular disease, neurodegenerative disease, metabolic disease, or autoimmune disease. The cancer may be, for example, a cancer such as acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid, non-Hodgkin's lymphoma, ovarian cancer, pancreatic cancer, glioma, melanoma, liver cancer, prostate cancer, and/or urinary bladder cancer. The target epitope may be, for example, a tumor associated antigen selected from the group consisting of A3, antigen specific for A33 antibody, BrE3, CD1, CD1a, CD3, CD5, CD15, CD19, CD20, CD21, CD22, CD23, CD25, CD30, CD45, CD74, CD79a, CD80, HLA-DR, NCA 95, NCA90, HCG and its subunits, CEA, CSAp, EGFR, EGP-1, EGP-2, Ep-CAM, Ba 733, HER2/neu, KC4, KS-1, KS1-4, Le-Y, MAGE, MUC1, MUC2, MUC3, MUC4, PAM-4, PSA, PSMA, RS5, S100, TAG-72, p53, tenascin, IL-6, insulin growth factor-1 (IGF-1), Tn antigen, Thomson-Friedenreich antigens, tumor necrosis antigens, VEGF, 17-1A, an angiogenesis marker, a cytokine, an immunomodulator, an oncogene marker, an oncogene product, and other tumor associated antigens.

The present invention also provides a method of treating a disease in a subject, by administering to a subject suffering from the disease (i) a tetravalent binding molecule having two binding sites for a carrier epitope and two binding sites for a target epitope, where the target epitope is an epitope associated with the disease, (ii) optionally, a clearing agent, and (iii) a targetable construct having a molecular scaffold and at least two carrier epitopes. The disease may be, for example, a hyperproliferative disease, pathogenic disease, cancer, cardiovascular disease, neurodegenerative disease, metabolic disease, or autoimmune disease. The targetable construct used in the method may contain a bioactive moiety.

The present invention also provides a method of diagnosing/detecting a disease in a subject, by administering to a subject suspected of suffering from the disease (i) a tetravalent binding molecule having two binding sites for a carrier epitope and two binding sites for a target epitope, (ii) optionally, a clearing agent, and (iii) a targetable construct having a molecular scaffold and at least two carrier epitopes, where the construct has a detectable label. The target epitope may, for example, be contained within, displayed by or released from one or more cells, tissues, organs or systems of the subject.

The present invention also provides a kit, having (i) a tetravalent binding molecule having two binding sites for a carrier epitope and two binding sites for a target epitope, (ii) optionally, a clearing agent, and (iii) a targetable construct having a molecular scaffold and at least two carrier epitopes.

Additional aspects, features and advantages of the invention will be set forth in the description which follows, and in part will be obvious from the description, or may be learned by practice of the invention. The embodiments and advantages of the invention may be realized and obtained by means of the instrumentalities and combinations particularly pointed out in the appended embodiments.

DETAILED DESCRIPTION OF THE INVENTION

Figure 1:
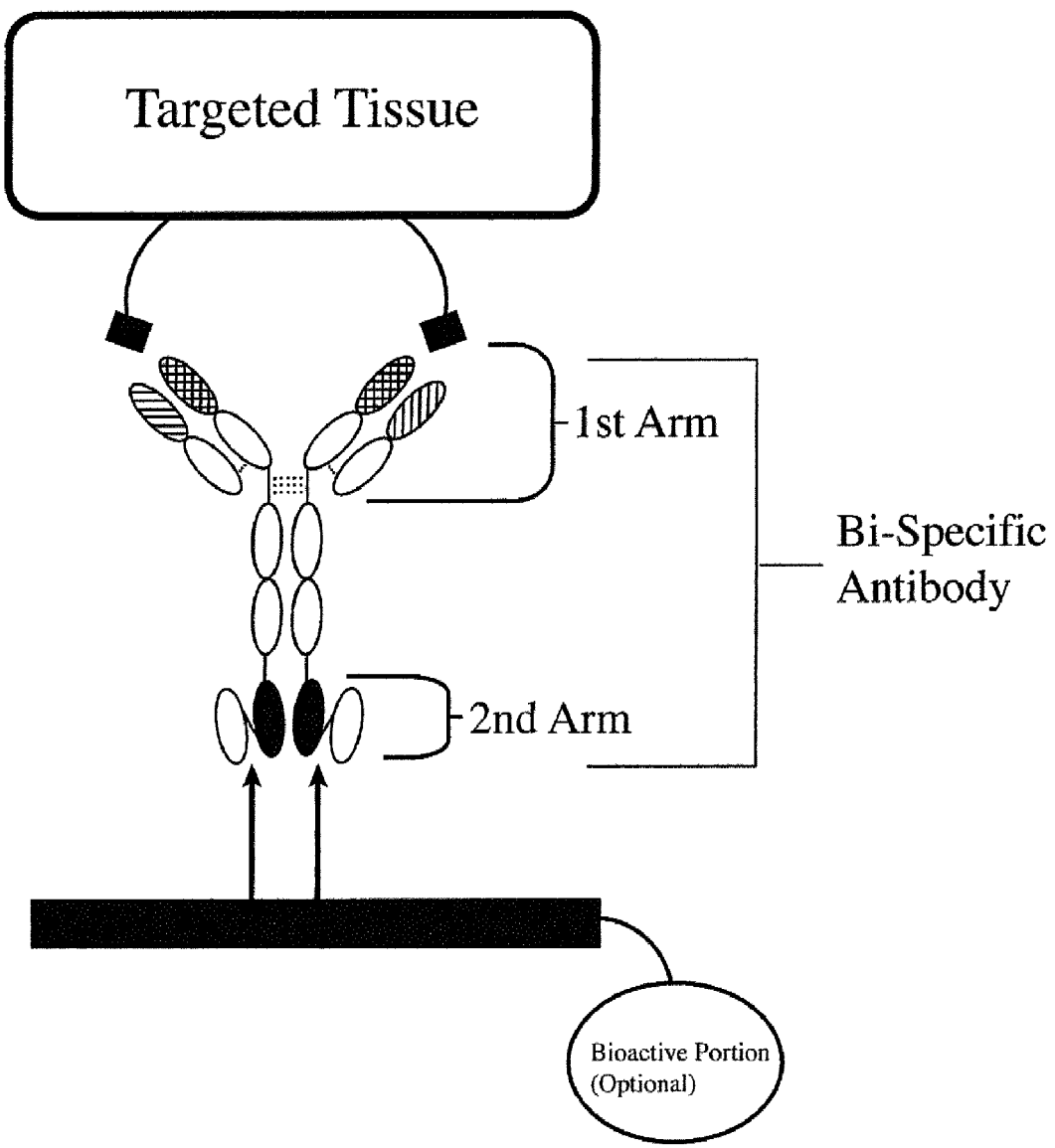
FIG. 1 schematically illustrates hMN14-734scFv, an example of a bispecific and divalent antibody of the invention. See published PCT Application WO 99/66951 for details of the structure and preparation of hMN14-734scFv. Symbols: solid black rectangle, molecular scaffold; → carrier epitopes, open circle, optional biologically active moiety; filled diamonds, target epitopes; and ovals, antibody domains. Each pair of filled and open ovals (bottom) represent an arm of the bi-specific antibody that binds a carrier epitope, and each pair of striped and cross-hatched ovals (top) represent an arm of the bi-specific that binds a target epitope.
Figure 2:
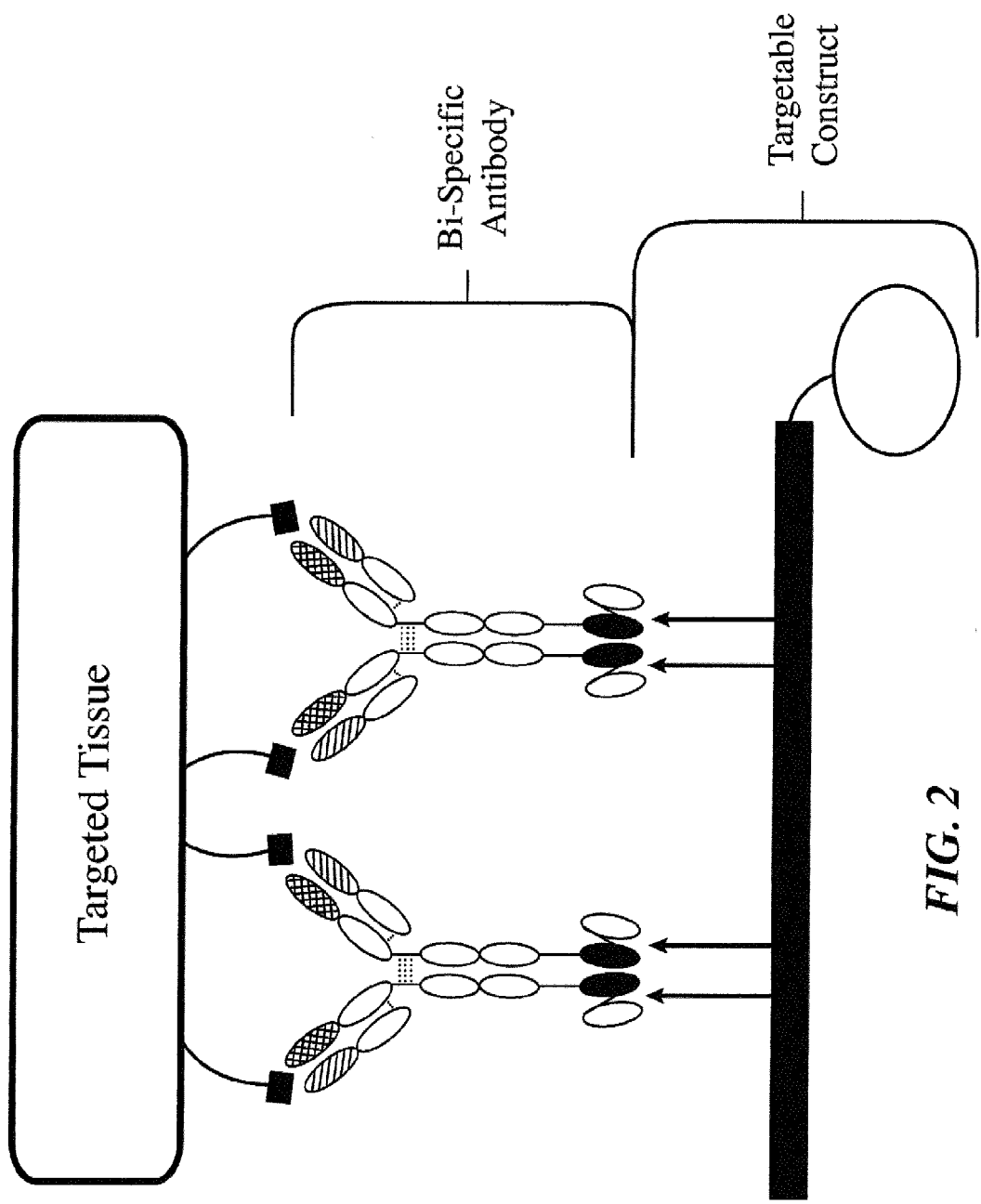
FIG. 2 schematically illustrates a tetravalent targetable complex of the invention. Two bi-specific and divalent antibody molecules are shown bound to a targetable construct. Symbols are the same as in FIG. 1.

The present invention provides targetable complexes comprising multivalent and polyspecific (e.g., bi-specific) antibodies. Bi-specific antibodies have at least one arm that specifically binds a targeted tissue and at least one other arm that specifically binds a targetable construct.

A "targeted tissue" is a system, organ, tissue, cell, intracellular component, receptor, or organelle to which a targetable construct is preferentially delivered. In the therapeutic aspects of the invention, the targeted tissue is infected and/or misfunctioning (e.g., cancer cells, infected cells, ectopic cells, etc.).

In addition to antibodies, the complexes comprise at least one targetable construct. A "targetable construct" comprises a molecular scaffold which comprises or bears at least two pairs of carrier epitopes recognized by the arm of the bi-specific antibody. As used herein, a "molecular scaffold" (or simply "scaffold") is any chemical structure to which epitopes and other moieties can be attached at a variety of positions, and/or with a variety of orientations, relative to the scaffold and/or other moieties. Non-limiting examples of molecular scaffolds include polymers such as peptides or peptide derivatives, oligopeptides and oligonucleotides. See Skerra, Engineered protein scaffolds for molecular recognition, *J. Mol. Recog.* 13:167-187, 2000; Erratum in: *J. Mol. Recog.* 14:141, 2001. The oligonucleotides can be antisense oligonucleotide molecules or genes that correspond to p53. Also, an oligonucleotide, such as an antisense molecule inhibiting bcl-2 expression is described in U.S. Pat. No. 5,734,033 (Reed).

The epitopes of a targetable construct are called "carrier eptiopes" herein. As used herein, the term "epitope" (also known as "immunogenic recognition moiety") encompasses any molecule or moiety that is specifically bound by a recognition moiety or molecule. Non-limiting examples of recognition moieties and molecules include antibodies, antibody derivatives, antigen-binding regions and minimal recognition units of antibodies, and receptor-specific ligands.

Non-limiting examples of recognizable haptens include, but are not limited to, chelators, such as diethylenetriaminepentaacetic acid (DIM), histamine-succinyl glycine (HSG), fluorescein isothiocyanate (FITC), vitamin B-12 and other moieties to which specific antibodies can be raised, with scFv being preferred. Antibodies raised to the HSG or DTPA hapten are known and the scFv portion of the antibody can be used as a carrier epitope binding arm of a bi-specific antibody. Binding of the carrier eptiopes is highly specific for each scFv component.

The targetable construct is multivalent, with bivalent peptides being the preferred peptide. The targetable construct may, but need not, be linked or conjugated to a variety of agents useful for treatment. Alternatively, the targetably construct may be administered in combination with such agents. Examples of such agents include, but are not limited to, metal chelate complexes, folate moieties, drugs, toxins and other effector molecules, such as cytokines, lymphokines, chemokines, immunomodulators, enzymes, radiosensitizers, asparaginase, RNAse, DNAse, carboranes, receptor targeting agents and radioactive halogens. Additionally, enzymes useful for activating a prodrug or increasing the target-specific toxicity of a drug can be conjugated to the carrier. Thus, the use of a bi-specific antibody which have at least one arm that specifically binds a targetable construct allows a variety of applications to be performed without raising new bsAb for each application.

The term "antibody fragment" (also known as "antibody derivative") encompasses any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("scFv proteins"), and minimal recognition units consisting of the amino acid residues that mimic the hypervariable region. Antibodies and antibody fragments are described in more detail below.

I. Biological Activity of Targetable Constructs and Complexes

A targetable construct may be biologically active due to the activity of the molecular scaffold, or the construct may optionally comprise a biologically active moiety. A targetable complex may be biologically active due to the activity of the targetable construct, or the complex may optionally comprise a biologically active moiety or molecule.

I.A. Definitions

The term "biologically active" (synonymous with "bioactive") indicates that a composition or compound itself has a biological effect, or that it modifies, causes, promotes, enhances, blocks, reduces, limits the production or activity of, or reacts with or binds to an endogenous molecule that has a biological effect. A "biological effect" may be but is not limited to one that stimulates or causes an immunreactive response; one that impacts a biological process in an animal; one that impacts a biological process in a pathogen or parasite; one that generates or causes to be generated a detectable signal; and the like. Biologically active compositions, complexes or compounds may be used in therapeutic, prophylactic and diagnostic methods and compositions. Biologically active compositions, complexes or compounds act to cause or stimulate a desired effect upon an animal. Non-limiting examples of desired effects include, for example, preventing, treating or curing a disease or condition in an animal suffering therefrom; limiting the growth of or killing a pathogen in an animal infected thereby; augmenting or altering the phenotype or genotype of an animal; and stimulating a prophylactic immunoreactive response in an animal.

In the context of therapeutic applications of the invention, the term "biologically active" indicates that the composition, complex or compound has an activity that impacts an animal suffering from a disease or disorder in a positive sense and/or impacts a pathogen or parasite in a negative sense. Thus, a biologically active composition, complex or compound may cause or promote a biological or biochemical activity within an animal that is detrimental to the growth and/or maintenance of a pathogen or parasite; or of cells, tissues or organs of an animal that have abnormal growth or biochemical characteristics, such as cancer cells, or cells affected by autoimmune or inflammatory disorders.

In the context of prophylactic applications of the invention, the term "biologically active" indicates that the composition or compound induces or stimulates an immunoreactive response. In some preferred embodiments, the immunoreactive response is designed to be prophylactic, i.e., prevents infection by a pathogen. In other preferred embodiments, the immunoreactive response is designed to cause the immune system of an animal to react to the detriment of cells of an animal, such as cancer cells, that have abnormal growth or biochemical characteristics. In this application of the invention, compositions, complexes or compounds comprising antigens are formulated as a vaccine.

It will be understood by those skilled in the art that a given composition, complex or compound may be biologically active in therapeutic, diagnostic and prophylactic applications. A composition, complex or compound that is described as being "biologically active in a cell" is one that has biological activity in vitro (i.e., in a cell culture) or in vivo (i.e., in the cells of an animal). A "biologically active portion" of a compound or complex is a portion thereof that is biologically active once it is liberated from the compound or complex. It should be noted, however, that such a component may also be biologically active in the context of the compound or complex.

In order to achieve a biological effect, invention constructs may comprise an additional moiety to facilitate internalization and/or uptake by a target cell. For aspects of the present invention that involve an internalization moiety, internalization can be accomplished in various ways. In particular embodiments, the internalization moiety binds to a recycling receptor, such as a folate receptor. For binding to a folate receptor, the internalization moiety can, for example, include folate or methotrexate, or a folate analog binding to a folate receptor. In other embodiments, the internalization moiety includes a peptide that enhances non-receptor mediated internalization.

Likewise, a number of internalization mechanisms can be utilized in place of the folate receptor with folate or methotrexate. For example, hormone or hormone analog/hormone receptor pairs such as steroid hormones; specific peptide/peptide receptor; and non-receptor mediated peptide internalization.

A variety of different species that enhance internalization are known and can be utilized. Examples include folic acid (folate) or methotrexate with internalization via folate receptor; steroid hormones and their respective receptors; receptor-recognized peptides, e.g., somatostatin, LHRH bombesin/CCKB, substance P, VIP. In addition, antibodies that cross-link the targetable construct to a rapidly internalizing membrane protein can also be used to enhance internalization.

I.B. Therapy of Tissues and Organs

I.B.1. Cardiovascular Lesions, Atherosclerotic Plaques and Vascular Clots

When there is an insult to vascular endothelium, circulating blood cells, particularly leukocytes, accumulate. Granulocytes tend to concentrate in the largest numbers, but monocytes and lymphocytes also accumulate to a lesser degree. These cells wander through the vascular endothelium to congregate in the areas of injury. The granulocytes survive in the extravascular space for up to about three days, after which the mononuclear cells, monocytes and lymphocytes, become the dominant population.

Two phases are associated with a vascular insult. The first phase involves a brief early increase in vascular permeability. The more prolonged second phase involves increased permeability, attachment of leukocytes, mainly granulocytes, to the vessel wall, diapedesis of predominately leukocytes through the vessel wall, accumulation of leukocytes in the injured area, leukocyte phagocytosis, leakage of fibrinogen and platelets from the vessel, fibrin deposition in the injured area, intravascular clotting with vessel destruction, macrophage engulfment of necrotic debris, migration of fibroblasts and formation of connective tissue, and the neovascularization by ingrowth of capillaries. Infiltration by leukocytes, particularly granulocytes, is a relatively early and significant event in the response to vascular insult.

The well-developed atherosclerotic plaque is a result of the interplay of inflammatory and repair events, resulting in a lesion consisting of extracellular calcium salts, cholesterol crystals, glycosaminoglycans, and blood cells and plasma components. Endothelial permeability of arterial walls is induced in early stages of atherosclerosis, allowing the afflux of circulating macromolecules and blood cells, particularly leukocytes (and mainly granulocytes). Secondary changes may involve reduction in permeability of the arterial intima, and the later deposition of platelets and/or fibrin, proliferative, degenerative, necrotic, and repair processes that result in atheromatous lesions. Here again, an early component is the concentration and extravasation of leukocytes in the injured area.

With regard to clots, when vessels are injured, plugging may occur by the formation of fibrin, the aggregation of platelets, and combinations of both. During these events, leukocyte sticking and aggregation, independent of platelet aggregation, occurs. Very early, even before fibrin formation, extravasation of leukocytes takes place.

Deep vein thrombosis (DVT) and pulmonary embolism are very common in the general population, affecting 30% to 60% of otherwise healthy men and women, and up to 80% in high-risk patients. It has been estimated that as much as 20% of all hospital patients are affected with thromboembolic events. In the U.S. alone, it has been estimated that 2.5 million cases occur each year (Sherry, *Sem. Nucl. Med.* 7: 205-211, 1977).

The majority of commonly used nuclear medicine tests for deep vein thrombosis (DVT) involve nonspecific radiopharmaceuticals employed for radionuclide venography. There is thus an ongoing need for a thrombosis-specific radiopharmaceutical for specific, sensitive, and rapid disclosure of thrombi by non-invasive external scintigraphy. Contrast venography, a common radiological method, has been the "gold standard" for DVT, but it has a high incidence of side effects which limit its repeated use (Rabinov and Paulin, *Arch. Surg.* 104:134-144, 1972). Compression B-mode ultrasound is also of use for diagnosing the presence of thrombi in the legs, but this is region-limited and, again, not lesion-specific (Lensing et al., *N. Engl. J. Med.* 320:342-345, 1989). Hence, radiopharmaceuticals are being sought to achieve simplicity, rapidity, and specificity for the detection and diagnosis of DVT.

Where the aforementioned imaging agents may be useful for DVT, they may fail to disclose pulmonary emboli, which are life-threatening lesions. Different thrombi may require different agents. Venous thrombi consist primarily of polymers of fibrin with entrapped cells, alternating with layers of platelets, whereas arterial thrombi are made up primarily of aggregated platelets with less fibrin (Freiman, in: Coleman et al., eds, *Hemostasis and Thrombosis—Basic Principles and Clinical Practice*. New York, N.Y., Lippincott, 56: 766-780, 1982).

For the most part, the agents available appear to be restricted to either fibrin-directed or platelet-directed pharmaceuticals, as reviewed by Knight, *Sem. Nucl. Med.* 20:52-67, 1990. Fibrin-specific radiopharmaceuticals include radiolabeled fibrinogen, soluble fibrin, antifibrin antibodies and antibody fragments, fragment $E_1$ (a 60 kDa fragment of human fibrin made by controlled plasmin digestion of crosslinked fibrin), plasmin (an enzyme in the blood responsible for dissolution of fresh thrombi), plasminogen activators (e.g., urokinase, streptokinase and tissue plasminogen activator), heparin, and fibronectin (an adhesive plasma glycoprotein of 450 kDa).

Platelet-directed pharmaceuticals include radiolabeled platelets, antiplatelet antibodies and antibody fragments, anti-activated-platelets, and anti-activated-platelet factors, which have been reviewed by Knight (Id.), as well as by Koblik et al., *Sem. Nucl. Med.* 19:221-237 1989, all of which are included herein by reference. Platelet imaging is most useful during the acute phase of thrombosis, when active platelet aggregation occurs, so that these platelet-based imaging methods have difficulty in disclosing clots that are older than about 24 to about 48 hours (Oster et al., *Proc. Natl. Acad. Sci. USA* 82:3465-3468, 1985). Another concern is that platelet imaging may be inhibited by concurrent heparin administration in the treatment of these patients (Seabold et al., *J. Nucl. Med.* 29:1169-1180, 1988). Heparinization can also reduce the total number of lesions found with anti-fibrin antibodies (Alavi et al., *J. Nucl. Med.* 29:825, 1988). In comparison to antifibrin antibodies, fragment $E_1$ that is radiolabeled appears to demonstrate clots earlier (Koblik et al., supra). However, the fragment $E_1$ is difficult to isolate and prepare, and its binding to blood clots is transient (Knight et al, *Radiology* 156:509-514, 1985).

Inadequate blood and oxygen supply to the myocardium, inducing symptoms of myocardial ischemia or ischemic heart disease, are the usual events resulting from stenotic coronary atherosclerosis. Acute and total coronary artery occlusion results in severe ischemia and, consequently, myocardial infarction. Chronologically, in the first hour, subcellular changes of ischemic heart muscle manifest as mitochondrial granules, reduction of glycogen and respiratory enzymes. Thereafter, from about 1 to about 6 hours, margination and clumping of nuclear chromatin, loss of nuclear and myofilament architecture, and infiltration with granulocytes, are observed. In the next phase, from about 6 to 12 hours, typical ischemic necrosis is seen. After 24 hours, severe histological changes are easily seen, leading to focal hemorrhage of different size and dilated capillaries by days 2-4.

Accordingly, the present invention provides compositions and methods for the detection and/or treatment of cardiovascular disorders, including fibrin clots, deep vein thrombosis, emboli, ischemia, and atherosclerotic plaques.

I.B.2. Anatomically Displaced or Ectopic Tissues and Organs

The invention provides compositions and methods for treating a mammal having a hypoplastic, absent, anatomically displaced or ectopic tissue or organ. Where normal organs or tissues are developed abnormally or are displaced in the body, or are insufficiently removed during ablative surgery, the tissue/organ-associated antibodies may be used as tissue-targeted vehicles for delivering therapeutic agents to the tissues in order to induce their involution or chemical and/or isotopic ablation. The antibodies or their fragments, or recognition moities, can be conjugated to or administered in combination with therapeutic modalities including, but not limited to, isotopes, drugs, toxins, photodynamic therapy agents, cytokines, hormones, autocrines, etc., which are used as cytotoxic or modulating agents, and which have hitherto been employed principally as toxic conjugates to cancer-targeting antibodies, as described in reviews by Waldmann, *Science* 252:1657, 1991; Koppel, *Bioconjug. Chem.* 1:13, 1990; Oeltmann and Frankel, *FASEB J.* 5:2334, 1991; and van den Bergh, Chemistry in Britain, May 1986, 430-439, each of which is incorporated by reference herein in its entirety.

The method comprises the steps of (a) parenterally injecting a mammalian subject, at a locus and by a route providing access to the tissue or organ, with an amount of a scintigraphic imaging agent or magnetic resonance image enhancing agent sufficient to permit a scintigraphic image or an enhanced magnetic resonance image of the structure to be effected; and (b) obtaining a scintigraphic image or an enhanced magnetic resonance image of the structure, at a time after injection of the agent sufficient for the agent to accrete in the structure. The targetable complex comprises an antibody or antibody fragment that specifically binds to the organ or tissue, and further comprises a bioactive (therapeutic) agent. In the case of naked antibodies, the complex itself may be biologically active and induce processes such as apoptosis.

Tissues, organs, and conditions of interest include but are not limited to:

(1) hypoplastic or absent tissue or organs, in conditions such as, juvenile diabetes, wherein the islet cells of the pancreas can be atrophic or significantly reduced; thymic aplasia or agenesis; DiGeorge's Syndrome wherein there is a hypoplasia or absence of parathyroid and the thymus;

(2) ectopic tissue and organs, such as, implants of endometrial glands and stroma;

(3) retained tissue, such as, retained placental tissue after pregnancy, and organ remnants after surgical removal of the organ;

(4) the condition of organs adjacent to a surgically removed organ; and (5) ablation of certain normal organs and tissues for other therapeutic purposes, such as the spleen in patients with immune disease or lymphomas, the bone marrow in patients requiring bone marrow transplantation, or normal cell types involved in pathological processes, such as certain T-lymphocytes in particular immune diseases.

The above methods of the invention include the use of a growth factor receptor antibody or a hormone receptor antibody to target to end-organs bearing such receptor(s), the functions of which can be blocked with said antibodies. An isotopic or drug conjugate of these antibodies can also be used to deliver a therapeutic agent to said tissues and organs, in order to affect diseases of tissues which bear such receptors. For example, in endometriosis, involving ectopic endometrial tissue, the current standard drug therapy involves administration of a synthetic steroid derived from ethisterone (DANO-CRINE brand of danazol), which is chemically a 17-alpha-Pregna-2,3-dien-20-yno[2,3,3-d]-isoxazol-17-ol. This probably acts, at least in part, on sex steroid metabolism and with sex hormone receptors, particularly follicle-stimulating hormone (FSH) and luteinizing hormone (LH) at the target organ. It is now possible to use an antibody against these gonadal steroid receptors, alone or as an immunoconjugate with isotopes, drugs, toxins, hormone antagonists, cytokines, autocrines, etc., to inactivate and make the ectopic endometrium atrophic.

The above methods of the invention include providing an immunological method of affecting ovarian and other hormone end-organ function, such as to induce amenorrhea or sterility. By use of an ovarian-targeting antibody or an antibody to an ovarian-related hormone receptor, such as FSH receptor, either as unconjugated antibodies or as antibodies conjugated with a therapeutic principle, a relatively convenient and safe method of blocking ovarian function and inducing atrophy at the end-organ can be achieved.

Many hormone and growth factor receptors are known, and frequently show sufficient organ and tissue proclivity to allow these to serve as targets for antibodies which, when bound to said receptors, affect the function of the tissues and result in an immunological or, by the use of conjugates with drugs, a chemical ablation, or a radiation ablation when used as a conjugate with therapeutic isotopes.

Another application is in the treatment of fibrocystic breast disease. An antibody to FSH receptor or to estrogen receptor can be given alone or as an immunoconjugate with a therapeutic principle to decrease the fibrocystic disease and to control its symptoms.

Still another indication is in benign prostatic hyperplasia or prostatic cancer, where the use of an antibody against an androgen receptor can alone, or as a conjugate with a therapeutic principle (hormone end-organ antagonist, cytotoxic drug, toxin, or isotope), can decrease the prostatic tissue proliferation.

Another therapeutic application for such organ- and tissue-targeting antibodies conjugated with a toxic agent is for the ablation of certain normal cells and tissues as part of another therapeutic strategy, such as in bone marrow ablation with antibodies against bone marrow cells of particular stages of development and differentiation, and in the cytotoxic ablation of the spleen in patients with lymphoma or certain immune diseases, such as immune thrombocytopenic purpura, etc.

Another therapeutic application for such organ- and tissue-targeting antibodies or fragments is to link them to a cytoprotective agent to form therapeutic conjugates. The conjugate is administered to a patient undergoing chemotherapy or radiation therapy so that the targeted normal organs and tissues are protected during the therapy.

I.B.3. Cancer

The present invention further provides compositions and methods for treating a disease state selected from the group consisting of a carcinoma, a melanoma, a sarcoma, a neuroblastoma, a leukemia, a glioma, a lymphoma and a myeloma. Specific tumor-associated antigens may be associated with a type of cancer selected from the group consisting of acute lymphoblastic leukemia, acute myelogenous leukemia, biliary, breast, cervical, chronic lymphocytic leukemia, chronic myelogenous leukemia, colorectal, endometrial, esophageal, gastric, head and neck, Hodgkin's lymphoma, lung, medullary thyroid, non-Hodgkin's lymphoma, ovarian, pancreatic, glioma, melanoma, liver cancer, prostate, and urinary bladder. A tumor-associated antigen may be selected from the group consisting of A3, the antigen specific for the A33 antibody, BrE3, CD1, CD1a, CD3, CD5, CD15, CD19, CD20, CD21, CD22, CD23, CD25, CD30, CD33, CD45, CD74, CD79a, CD80, NCA90, NCA 95, HLA-DR, CEA, CSAp, EGER, EGP-1, EGP-2, Ep-CAM, Ba 733, HER2/neu, KC4, KS-1, KS1-4, Le-Y, 5100, MAGE, MUC1, MUC2, MUC3, MUC4, PAM-4, PSA, PSMA, AFP, HCG and ist subunits, RS5, TAG-72, tenascin, IL-6, insulin growth factor-1 (IGF-1), Tn antigen, Thomson-Friedenreich antigens, tumor necrosis antigens, VEGF, 17-1A, an angiogenesis marker, a cytokine, an immunomodulator, an oncogene marker (e.g., p53), and an oncogene product.

Tumor-associated markers have been categorized by Herberman (see, e.g., Immunodiagnosis of Cancer, in THE CLINICAL BIOCHEMISTRY OF CANCER, Fleisher ed., American Association of Clinical Chemists, 1979) in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361,644 and 4,444,744. Markers of tumor vasculature (e.g., VEGF), of tumor necrosis, of membrane receptors (e.g., folate receptor, EGFR), of transmembrane antigens (e.g., PSMA), and of oncogene products can also serve as suitable tumor-associated targets for antibodies or antibody fragments. Markers of normal cell constituents which are over-expressed on tumor cells, such as B-cell complex antigens, as well as cytokines expressed by certain tumor cells (e.g., IL-2 receptor in T-cell malignancies) are also suitable targets for the antibodies and antibody fragments of this invention.

The BrE3 antibody is described in Couto et al., *Cancer Res.* 55:5973s-5977s, 1995. The EGP-1 antibody is described in U.S. Provisional Application Ser. No. 60/360,229, some of the EGP-2 antibodies are cited in Staib et al., *Int. J. Cancer* 92:79-87, 2001; and Schwartzberg et al., *Crit. Rev. Oncol. Hematol.* 40:17-24, 2001. The KS-1 antibody is cited in Koda et al., *Anticancer Res.* 21:621-627, 2001; the A33 antibody is cited in Ritter et al., *Cancer Res.* 61:6854-6859, 2001; Le(y) antibody B3 is described in Di Carlo et al., *Oncol. Rep.* 8:387-392, 2001; and the A3 antibody is described in Tordsson et al., *Int. J. Cancer* 87:559-568, 2000.

Also of use are antibodies against markers or products of oncogenes, or antibodies against angiogenesis factors, such as VEGF. VEGF antibodies are described in U.S. Pat. Nos. 6,342,221, 5,965,132 and 6,004,554, and are incorporated by reference in their entirety. Antibodies against certain immune response modulators, such as antibodies to CD40, are described in Todryk et al., *J. Immunol. Meth.* 248:139-147, 2001 and Turner et al., *J. Immunol.* 166:89-94, 2001. Other antibodies suitable for combination therapy include anti-necrosis antibodies as described in Epstein et al., see e.g., U.S. Pat. Nos. 5,019,368; 5,882,626; and 6,017,514.

I.B.4. Autoimmune Diseases

The present invention further provides compositions and methods for treating an autoimmune disease or disorder. Immunothereapy of autoimmune disorders using antibodies which target B-cells is described in PCT Application Publication No. WO 00/74718, which claims priority to U.S. Provisional Application Ser. No. 60/138,284, the contents of each of which is incorporated herein in its entirety. Exemplary autoimmune diseases are acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

I.C. Therapeutic Applications

I.C.1. Photodynamic Diagnosis or Therapy (PDT)

The present mutant bsAb can be used in a method of photodynamic therapy (PDT) as discussed in U.S. Pat. Nos. 6,096,289; 4,331,647; 4,818,709; 4,348,376; 4,361,544; 4,444,744; 5,851,527.

In PDT, a photosensitizer, e.g., a hematoporphyrin derivative such as dihematoporphyrin ether, is administered to a subject. Anti-tumor activity is initiated by the use of light, e.g., 630 nm. Alternate photosensitizers can be utilized, including those useful at longer wavelengths, where skin is less photosensitized by the sun. Examples of such photosensitizers include, but are not limited to, dihematoporphyrin, benzoporphyrin monoacid ring A (BPD-MA), tin etiopurpurin (SnET2), sulfonated aluminum phthalocyanine (AlSPc) and lutetium texaphyrin (Lutex).

Radionuclides useful in therapeutic agents, which substantially decay by beta-particle emission include, but are not limited to: P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Tb-161, Ho-166, Er-169, Lu-177, Re-186, Re-188, Re-189, Ir-194, Au-198, Au-199, Pb-211, Pb-212, and Bi-213. Maximum decay energies of useful beta-particle-emitting nuclides are preferably 20-5,000 keV, more preferably 100-4,000 keV, and most preferably 500-2,500 keV.

Radionuclides useful in therapeutic agents which substantially decay with Auger-emitting particles include, but are not limited to: Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV.

Radionuclides useful in therapeutics and which substantially decay with generation of alpha-particles include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-9,000 keV, more preferably 3,000-8,000 keV, and most preferably 4,000-7,000 keV.

Metals useful, as complexes, as part of a photodynamic therapy procedure include, but are not limited to zinc, aluminum, gallium, lutetium and palladium.

Therapeutically useful immunoconjugates can be obtained by conjugating photoactive agents or dyes to an antibody composite. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al., eds., *Photodynamic Therapy of Tumors and Other Diseases* (Libreria Progetto 1985); van den Bergh, *Chem. Britain* 22:430, 1986). Moreover, monoclonal antibodies have been coupled with photoactivated dyes for achieving phototherapy. Mew et al., *J. Immunol.* 130:1473, 1983; idem., *Cancer Res.* 45:4380, 1985; Oseroff et al., *Proc. Natl. Acad. Sci. USA* 83:8744, 1986; idem., *Photochem. Photobiol.* 46:83, 1987; Hasan et al., *Prog. Clin. Biol. Res.* 288:471, 1989; Tatsuta et al., *Lasers Surg. Med.* 9:422, 1989; Pelegrin et al., *Cancer* 67:2529, 1991. However, these earlier studies did not include use of endoscopic therapy applications, especially with the use of antibody fragments or subfragments. Thus, the present invention contemplates the therapeutic use of immunoconjugates comprising photoactive agents or dyes.

I.C.2. Boron Neutron Capture Therapy (BNCT)

BNCT is a binary system designed to deliver ionizing radiation to tumor cells by neutron irradiation of tumor-localized boron-10 atoms. BNCT is based on the nuclear reaction which occurs when a stable isotope, isotopically enriched B-10 (present in 19.8% natural abundance), is irradiated with thermal neutrons to produce an alpha particle and a Li-7 nucleus. These particles have a path length of about one cell diameter, resulting in high linear energy transfer. Just a few of the short-range 1.7 MeV alpha particles produced in this nuclear reaction are sufficient to target the cell nucleus and destroy it. Barth et al., *Cancer* 70:2995-3007, 1992.

Historically, BNCT was first employed for the treatment of glioblastoma (a fatal form of brain tumor) and other brain tumors at a time when tumor specific substances were almost unknown. Hatanaka et al., in *Boron Neutron Capture Therapy for Tumors*, pp. 349-78 (Nishimura Co., 1986). One of the first boronated compounds employed, a sulfhydryl-containing boron substance called sodium borocaptate or BSH ($Na_2B_{12}H_{11}SH$), crosses the blood-brain barrier to localize in brain, and this has been the anatomical basis for neutron capture therapy of brain tumors. Clinical trials have been carried out, or are scheduled, for the treatment of gliomas in Japan, the US and Europe. Barth et al., *Cancer*, supra. Problems with previous inorganic boron therapy methods was that the boron reached both targeted and non-target areas. Accordingly, when the boron was irradiated, healthy cells as well as cancerous cells were destroyed.

The BNCT concept has been extended to other cancers, spurred on by the discovery of a number of tumor-localizing substances, including tumor-targeting monoclonal antibodies. For instance, boronated amino acids such as p-boronophenylalanine accumulated in melanoma cells. The potential of using boronated monoclonal antibodies directed against cell surface antigens, such as CEA, for BNCT of cancers has been demonstrated. Ichihashi et al., *J. Invest. Dermatol.* 78:215-18, 1982; Goldenberg et al., *Proc. Natl. Acad. Sci. USA* 81:560-63, 1984; Mizusawa et al., *Proc. Natl. Acad. Sci. USA* 79:3011-14, 1982; Barth et al., *Hybridoma* 5(supp. 1):543-5540, 1986; Ranadive et al., *Nucl. Med. Biol.* 20: 663-68, 1993.

Success with BNCT of cancer requires methods for localizing a high concentration of boron-10 at tumor sites, while leaving non-target organs essentially boron-free. Compositions and methods for treating tumors in patients using pre-targeting bsAb for BNCT are described in U.S. application Ser. No. 09/205,243 and can easily be modified in accordance with the present invention. Additionally, other elements are suitable for neutron capture reactions. Nuclides useful in therapies based on neutron capture procedures include, but are not limited to: B-10, Gd-157 and U-235. Uranium, in large amounts, can be bound by naturally occurring chelating agents such as ferritin.

II. Pre-Formed Targetable Complexes

In therapeutic embodiments of the present invention, the bi-specific antibodies may be adminstered at some time prior to administration of the targetable construct. However, it is also possible to mix targetable constructs and bi-specific antibodies prior to administration, and thus to form "pre-formed" targetable complexes that are then administered to a subject. Targetable complexes are also useful in ex vivo and in vitro modalities.

II.A. Pre-Targeting Applications

In an exemplary method that does not involve pre-targeting, the targetable construct comprises a bioactive moiety. In this case, the targetable construct is administered following administration of the bsAb. The bioactive agent is targeted to the target site because the targetable construct is recognized by and binds to the bsAb, which is itself bound to a targeted tissue.

In an alternative method, a targetable construct comprising a bioactive agent is mixed with its cognate bsAb prior to administration to the patient, thus forming a targetable complex comprising a bioactive agent. A targetable complex formed in this fashion is administered and binds its targeted tissue, thereby effecting direct delivery of the bioactive agent as a part of the targetable complex comprising the agent.

The latter or pre-targeting modality has several potential advantages over methods in which the targetable constructs and bsAb are separately administered. The total amount of targetable construct and bsAb that needs to be administered in order to be effective may be less than in non-pre-targeting modalities, particularly if the targetable complex is relatively stable under physiological conditions. In addition, a targetable complex according to the invention may have a higher affinity for the targeted tissue that the targetable construct per se, thereby providing compositions and methods for more effective delivery of the bioactive agent to the targeted tissue.

Pre-formed targetable complexes may be used in any of the compositions and methods of the invention. One skilled in the art will be able to determine what site of complex formation (i.e., in vitro or in situ) is appropriate for any given application.

II.B. Immunoaffinity-Based Applications

II.B.1. Immunoaffinity

Immunoaffinity is known in the art and generally involves the immobilization of antibodies to a solid support, often in the form of beads, that are then packed into a column. A sample containing an antigen recognized by the antibody is passed through the column, wherein the antigen is bound and retained by the immobilized antibodies. The antigen is then washed off the column using any of a variety of methods known in the art. Depending on the particular circumstances, the antigen may be a substance that is being purified, or the antigen can be a contaminant that is being removed. For further details and reviews, see Springer, Section 10.11, Immunoaffinity Chromatography, Chapter 10 in: *Short Protocols in Molecular Biology*, 2nd Ed., Ausubel et al., eds., John Wiley and Sons, New York, 1992, pages 10-43 to 10-45); *Affinity Chromatography: A Practical Approach*, edited by Dean P. D. G., Johnson, W. S., Middle, F. A., IRL Press, 1985; Immunoaffinity Purification: Basic Principles and Operational Considerations, Yarmush et al., *Biotech Adv.* 10:412-446, 1992.

Immunoaffinity comprises three general steps: adsorption, washing and elution. In the first step, absorption, a substance of interest is bound by an antibody. Absorption is accomplished by, e.g., contacting a sample containing the substance of interest with an antibody bound to a solid support matrix in a suitable medium within a column. The next step is a washing step wherein impurities present in the fluid volume of the column, as well as those bound nonspecifically to the antibody, solid support or column walls, are removed. Washing is accomplished by passing a volume of a wash solution, e.g., buffer, such as phosphate buffered saline (PBS) through the column. The volume of wash solution used in the washing step should not be so great as to result in loss of the substance of interest but not so limited so as not to remove impurities. In the elution step, the target molecule is removed from the column by, e.g., addition of a solvent or other solution, or change in conditions such as temperature or pressure, that reduces the affinity of the substance of interest to the antibody or the affinity of the complex formed between an antibody and molecules of the substance of interest to the solid support. Elution of an antibody coupled to the substance of interest may be accomplished by either a salt gradient, to change the pH; buffered step-gradient, to change the ionic strength; or other methods known in the art.

Elution of the target molecule may be accomplished by a number of methods. There are no covalent bonds involved in the interaction between antibody and the substance of interest. Thus, the conditions of the buffer may be changed such that the affinity of the antibody:substance complex falls sufficiently to reduce the amount of effective binding to each other or to the solid support. This may be achieved by altering the pH or the ionic strength of the buffer, or both, or by chaotropic ions, e.g., cyanates. Increased separation may be obtained by gradient elution. In the case of immunosorption, the binding of a substance of interest to its antibody may be so strong that more harsh elution conditions are necessary, such as the use of buffers which are very strongly acidic or basic. Other methods of elution include use of chaotropic agents such as KSCN; organic solvents, e.g., ethylene glycol, DMSO, or acetonitrile; denaturing agents, e.g., 8 M urea or 6 M guanine; electrophoretic elution; pressure induced elution and metal ion elution. Preferably, the elution conditions allows for complete or mostly complete elution of the product after one or two column volumes have passed through the column.

Various impurities can be present and may have an unpredictable and adverse affect on the composition as it is used in the pharmaceutical industry. In the case of biological samples, typical impurities are blood clots, tissue debris, hair, foreign particles, activated coagulation factors, denatured proteins, plasma-free hemoglobin (e.g., irrigation fluid) added into a wound site, human viruses, antigens and antibiotics.

By way of non-limiting example, a sample may be passed through an immunoaffinity column having an immobilized antibody directed against the substance of interest. The immobilized antibodies react with and bind molecules of the substance of interest in the sample, thereby absorbing them and removing them from the solution. Although the substance of interest is retained on the column, impurities pass through the column. The column can then be washed with a buffer solution to remove any impurities remaining on the column, e.g., impurities retained by non-specific binding. The column is washed free of impurities and any substance bound to the column is eluted with a solvent. This process is known as positive immunoabsorption. In negative immunoabsorption, in contrast, the substances of interest present in the crude preparation pass freely through the column while the antigenic impurities bind with antibodies and are held by the column.

II.B.2. Immobilization of Antibodies

A solid support or matrix is used to immobilize antibodies. The matrix may possess desirable characteristics including, macroporosity, mechanical stability, ease of activation, hydrophilicity, and inertness, i.e., low nonspecific adsorption. Matrices commonly used by those skilled in the art include cross-linked dextran, agarose, polyacrylamide, cellulose, silica and poly(hydroxyethylmethacrylate). For immuno-adsorbents, beaded agarose is a preferred solid support by those skilled in the art due to its high adsorptive capacity for proteins, high porosity, hydrophilicity, chemical stability, lack of charge and relative inertness toward nonspecific adsorption.

Antibodies may be physically adsorbed to matrices or covalently attached to polymeric matrices containing hydroxylic or amino groups by means of bifunctional reagents, such as those disclosed herein. Attachment typically requires two steps, activation of the matrix and coupling of the ligand to the activated matrix. Activated matrices are available commercially. The selection method for coupling the ligand to the matrix is dictated in part by the choice of matrix and, in part, by the choice of antibody. Most methods commonly used to immobilize peptide or polypeptide ligands, such as antibodies, are based on coupling of amino groups. The polypeptide ligand must be coupled in a manner that will not interfere with its ability to be recognized by the target molecule. Methods for activation and coupling are commonly used by those skilled in the art.

For successful use of affinity chromatography, the polymer-bound ligand must be sufficiently distant from the polymer surface to minimize steric interference. This is accomplished by inserting an interconnecting link or spacer between the antibody and the matrix. The spacer may be bound directly to the matrix so that the antibody can be attached directly to these spacers. Types of spacers commonly used by those skilled in the art include but are not limited to cystamine, p-aminobenzoic acid, tyramine and p-hydroxy-mercuribenzoate.

II.B.3. Beads

In embodiments wherein the solid support is a bead, the bead may be any of a variety of types, depending upon the application. For immunopurification, porous beads are often used. The beads may be prepared from commercially available beads that are derivatized with amino or carboxyl groups that are available for linkage to a protein or other capture moiety using, for example, glutaraldehyde, carbodiimide, diazoto compounds, or any other suitable crosslinking reagent.

II.B.3.a. Magnetic Beads

Targetable complexes may be attached to magnetic particles via functional groups that coat the particles. In a purification application, a sample containing an antigen comprising a target epitope binds to the attached targetable complex, and the conjugated magnetic particle is removed from suspension by the application of a magnetic field.

Magnetic beads or particles, such as magnetic latex beads and iron oxide particles, to which the targetable complexes of the invention may be attached, are known in the art. For example, magnetic particles are described in U.S. Pat. No. 4,672,040. Coupling of capture moieties to magnetic beads can be accomplished using known methods. For example, beads are commercially available that are derivatized with amino or carboxyl groups that are available for linkage to a protein or other capture moiety using, for example, glutaraldehyde, carbodiimide, diazoto compounds, or other suitable crosslinking reagent. Silanization of magnetically responsive particles provides one method of obtaining reactive groups on the surface of the particles (see, e.g., U.S. Pat. No. 4,672,040 for a description of silanization and silane coupling chemistry). Linking bonds can include, for example, amide, ester, ether, sulfonalmide, disulfide, azo, and others known to those of skill in the art.

Superparamagnetic particles, which can be made from a number of substances such as polystyrene or iron oxide and polysaccharides, are magnetic when placed in a magnetic field, but retain no residual magnetism when removed from the magnetic field. This lack of residual magnetism ensures that the particles can be repeatedly separated and resuspended without magnetically induced aggregation.

II.B.3.b. Beads for Immunoaffinity Purification

Beads may be coated with the targetable complexes of the invention for use in immunoaffinity purification. Generally, such beads are of a size, composition and structure suitable for use in flow-through columns. Porous beads may be used. By way of non-limiting example, such beads can be made of SEPHADEX®, SEPHAROSE®, agarose, glass, and polystyrene.

II.B.4. Preparation of an Immunoaffinity Column

In column immunoaffinity, a column comprising a solid support onto which the construct or complex is immobilized is prepared. The preparation of the column depends on the type of solid support used, the chemical or physical nature of the samples to be processed through the column, reagents, e.g., washing and elution solutions, and the like.

It may be desirable to equilibrate the column before application of a sample. The buffering conditions used for equilibrating the affinity column in preparation for sample application will reflect the specific properties of the interacting system being used. The nature of the buffer used, including its pH and ionic strength, are adjusted for the particular antibody and substance of interest. The sample comprising the substance of interest that is applied to the column typically contained in the same buffer used to equilibrate the column. After sample application and absorption, the column is washed with the starting buffer to remove any unbound sample and any impurities. It may also be preferable in some instances to wash the column with buffers different from the starting buffer in order to remove nonspecifically adsorbed substances.

II.C. Manufacturing Embodiments

In addition to being useful for purifying compounds of interest from mixtures of compounds, immunoaffinity can be used to remove undesirable substances from mixtures in manufacturing and other applications. Exemplary undesirable substances include, but are not limited to, contaminants, undesirable reaction products and/or catalysts including but not limited to enzymes, that are used during manufacturing processes.

The immunoaffinity aspects of the invention may also be applied to manufacturing processes. A manufacturing process can be a "continuous process," in which the substance of interest is continually produced and harvested from an ongoing manufacturing or production process. In contrast, in a "batch" approach in manufacturing, multiple reparations are combined and then harvested. Regardless of the type of manufacturing process, the compositions of the invention can be used at any of a variety of steps in the process.

A sample or manufacturing preparation may be "clarified" prior to further preparation in order to remove contaminants (including without limitation, in chemical syntheses, reaction byproducts and unreacted compounds) produce a sample containing only, or enriched for, the substance of interest. Additionally or alternatively, a substance of interest may be partially purified, substantially purified or purified. A substance is said to be "partially purified" when it comprises $\geq 50\%$ w/w of a composition; "substantially purified" when it comprises $\geq 75\%$ of a composition, and "purified" when it comprises $\geq 90\%$, preferably $\geq 95\%$, more preferably $\geq 99\%$ and most preferably $\geq 99.9\%$ of a composition. Generally, clarification of a sample removes a limited number of undesirable compounds from a preparation without changing the concentration of the substance. In contrast, the purification of a substance generally refers to a process by which the substance is preferentially removed from a sample, leaving behind a variety of contaminants; the separated substance may be moved to a new solution in which its concentration is higher.

Impurities can be removed from a preparation of a substance of interest by negative or positive immunoabsorption techniques. A preparation so treated is said to be enriched for the substance of interest, and the substance of interest in the preparation is said to be partially purified, substantially purified or purified. The substance purified in this manner may be an antibody that specifically binds the carrier eptitope of the targetable construct, or a [target epitope]:[bi-specific antibody] complex.

When the latter type of complex is prepared, the target epitope may be further purified by treatment with agents or conditions that reduce the affinity of the bi-specific antibody for the target epitope. In instances where a targetable construct comprising a carrier epitope is attached to a solid support, and a bi-specific antibody is bound to the carrier epitope, the [target epitope]:[bi-specific antibody] complex can be separated from the bound targetable construct by addition of an excess amount of the carrier epitope. By way of non-limiting example, in the case of IMP 246 bound to a solid support, a complex comprising a bispecific antibody that is bound thereto may be removed from the bound IMP 246 by the addition of an excess amount of the chelator corresponding to the chelator moiety present on IMP 246, i.e., DTPA.

For example, a sample may be passed through an immunoaffinity column having an immobilized antibody directed against the substance of interest. The immobilized antibodies react with and bind molecules of the substance of interest in the sample, thereby absorbing them and removing them from the solution. Although the substance of interest is retained on the column, impurities pass through the column. The column can then be washed with a buffer solution to remove any impurities remaining on the column, e.g., impurities retained by non-specific binding. The column is washed free of impurities and any substance bound to the column is eluted with a solvent. This process is known as positive immunoabsorption. In negative immunoabsorption, in contrast, the substances of interest present in the crude preparation pass freely through the column while the antigenic impurities bind with antibodies and are held by the column.

II.D. Immunoassays and Other In Vitro Immunochemical Methods

The targetable complexes of the present invention may be used as reagents in a variety of in vitro immunochemical methods. Immunochemical methods include, but are not limited to, Western blotting, immunoaffinity purification, immunoprecipitation, ELISA, dot or slot blotting, radioimmunoassay (RIA), immunohistochemical staining, immunocytochemical staining, and flow cytometry.

Such methods may, but need not in every instance, involve the attachment of a targetable complexes to a solid support. The term "solid support" refers to a material having a solid surface to which a targetable complex is immobilized. By "immobilized" it is meant bound covalently, or bound by noncovalent means such as hydrophobic adsorption. By way of non-limiting example, a solid support may be the surface of a multiwell (microtiter) plate well, a bead, a membrane or a dipstick. Methods and means for covalently or noncovalently binding proteins to solid supports are known in the art.

Suitable solid supports include, by way of illustration and not limitation, latex, glass particles, including porous glass particles; polyacrylamide particles; agarose; SEPHADEX® (Pharmacia Fine Chemicals, Inc.); SEPHAROSE®; bibulous materials such as glass or cellulose paper; plastics and polymers (e.g., in sheets, beads or microtiter wells) such as polystyrene, polyvinyl chloride, polystyrene latex, or polyvinylidine fluoride (known as IMMULON®); nylon; polymethacrylate; etc.; silicons; metals such as gold and indium; nitrocellulose (e.g., in membrane or microtiter well form); activated beads; Protein A beads; diazotized paper; and the like.

The nature of the solid surface varies depending upon the intended use or method. For assays carried out in microtiter wells, e.g., in multiwell (microtiter) plates, the solid surface is the wall of the well or cup. For assays using beads, the solid surface is the surface of the bead. In assays using a dipstick (i.e., a solid body made from a porous or fibrous material such as fabric or paper) the surface is the surface of the material from which the dipstick is made. In agglutination assays the solid surface may be the surface of latex or gelatin particles. When individual antigens are bound to a solid surface they may be distributed homogeneously on the surface or distributed thereon in a pattern, such as bands so that a pattern of antigen binding may be discerned.

II.D.1. Immunoassays

The design of immunoassays is subject to a great deal of variation, and many formats are known in the art. *Immunochemical Protocols*, Humana Press, Totowa, N.J., 1998; *Current Protocols in Immunology*, Greene Pub. Associates and Wiley-Interscience, New York, N.Y., 1997. Protocols may, for example, use solid supports, or immunoprecipitation. Most assays involve the use of labeled targetable complex or antigen. As used in this section, an "antigen" is a substance that is or comprises a targetable epitope. The labels may be, for example, enzymatic, fluorescent, chemiluminescent, radioactive, or dye molecules. Assays which amplify the signals are known; examples of which are assays which utilize biotin and avidin, enzyme-labeled and mediated immunoassays, such as ELISA, RIA, immunofluorescence, chemiluminescence and nephelometry.

Typically, standard ELISA techniques are employed using labelled antibody or antigen. The label can be an enzyme, fluorophore, chemiluminescent material, radioisotope, or coenzyme. Generally enzyme labels such as alkaline phophatase, or beta galactosidase are employed together with their appropriate substrates. The enzyme/substrate reaction can be detected by any suitable means such as spectrophotometry.

The immunoassay may be, without limitation, in a heterogenous or in a homogeneous format, and of a standard or competitive type. In a heterogeneous format, the targetable construct or complex is typically bound to a solid support to facilitate separation of the sample therefrom after incubation. The solid support containing the targetable construct or complex is typically washed after separating it from the test sample, and prior to detection of bound antigens. In a homogeneous format, the test sample is incubated with the combination of targetable constructs or complexes in solution. For example, it may be under conditions that will precipitate any targetable complex/antigen assemblages that are formed. Both standard and competitive formats for these assays are known in the art.

In a standard format, the amount of antigen bond to the immobilized targetable construct or complex is directly monitored. This may be accomplished, for example, by detecting labeled anti-xenogenic (e.g., anti-human) antibodies that recognize an epitope on the bsAbs or targetable construct. In a competitive format, the amount of antigens in a sample is deduced by monitoring the competitive effect on the binding of a known amount of labeled antigen (or other competing ligand) added to the sample before or during the assay.

Targetable constructs or complexes may be immobilized to the inner surface of microtiter wells and the test sample and prelabeled target epitopes added to the wells. After a select period, the wells are washed and the color developed on the floor of the wells from the antibody-antigen reaction examined. By use of an automatic reader, the results of numerous tests can be determined in a few minutes.

II.D.2. Immunoassay Kits

The targetable complexes may be packaged in the form of a kit for use in immunoassays. The kit contain in separate containers the separate combination of targetable constructs, targetable complexes and bsAbs (either already bound to a solid matrix or separate with reagents for binding them to the matrix), control antibody formulations (positive and/or negative), labeled antibody when the assay format requires same and signal generating reagents (e.g., enzyme substrate) if the label does not generate a signal directly. Instructions (in any of a number of formats, e.g., written, tape, VCR, CD-ROM, etc.) for carrying out the assay may be included in the kit.

Test kits according to the invention for comprising a solid support that is an immunoassay contain, for example, a suitable container, coated with a targetable construct or targetable complex of the invention, optionally freeze-dried or concentrated solutions of a targeted epitope and/or a labelled derivative thereof, standard solutions of this protein, buffer solutions and, optionally, polypeptides and detergents for preventing non-specific adsorption and aggregate formation, pipettes, reaction vessels, calibration curves, instruction manuals and the like.

II.D.3. Dipsticks

The targetable constructs and complexes may be used in a "dipstick" or sheet which is capable of being inserted into and withdrawn from a sample. The dipstick is dipped into a well mixed urine sample, and after a time period of thirty seconds to two minutes, the various reagent bands are visually or optically examined for color changes. The bands can be visually compared to a preprinted color chart in order to determine the amount of each of the constituents or parameters being measured.

In a typical dipstick based analytical assay, a ligand, which specifically binds to the analyte of interest, is bound to a solid support on the dipstick. The dipstick is contacted with a sample in which the presence of the analyte of interest is to be determined. Frequently, steps are employed to aid in the removal of non-specifically bound material from the dipstick. Finally, the dipstick is processed to determine the presence of the analyte. The dipstick generally comprises a solid material, which is planar or columnar in geometry.

II.E. Ex Vivo Therapeutic Modalities

The compositions and devices of the invention, and methods of use thereof, may be used in ex vivo modalities. An "ex vivo modality" is one in which a biological sample, such as a body fluid, is temporarily removed from an animal, altered through in vitro manipulation designed to remove or inactivate one or more undesirable substances, and then returned to the body. One way in which undesirable substances may be removed from the sample is by contacting the sample with an agent that binds the undesirable substance. In an ex vivo modality of the invention, a sample that has been temporarily removed from a patient is contacted with a solid support comprising a targetable complex of the invention. In this embodiment, the undesirable substance is or comprises a target epitope that is recognized by the targetable complex of the solid support. The undesirable substance is, or is part of, e.g., a toxin, a hyperproliferative cell, an infected cell or a pathogen. For example, for the treatment of viremia, a virus that comprises a target epitope is cleared from blood by contacting the blood with a solid support comprising a targetable complex of the invention. The targetable complex recognizes and binds the virus, which is retained in the dialysis system but not in the blood that is returned to the patient.

An exemplary ex vivo modality of the invention is a hemodialysis system, which comprises a dialysis machine. A "dialysis machine" is a device in which a fluid such as blood of an animal is temporarily removed therefrom and processed through one or more physical, chemical, biochemical or other types of processes designed to remove or inactivate undesirable substances. Bodily waste produbts, toxins, venoms, overexpressed or overactive endogenous agents, molecules derived from any of the preceding, and pathogens comprising any of the preceding, are non-limiting examples of undesirable substances. In an exemplary mode, a human is treated by a dialysis machine that augments or substitutes for the natural kidney functions of a human body. Blood is removed from the body, passed through the dialysis machine, which separates the wastes from the blood extracorporeally. The separated wastes are discharged and disposed of, whereas the treated blood is returned to the body.

The transfer of blood between the patient and the dialyzer occurs within a blood tubing set that is usually disposable. The blood tubing set and the dialyzer represent a closed extracorporeal path through which a patient's blood travels. The blood tubing set includes an arterial line connected to an arterial reservoir for drawing blood from a patient, a venous line connected to a venous reservoir for returning blood to the patient, and a number of other lines for connecting a pump and the dialyzer between the arterial and venous reservoirs. Before the blood tubing set and the dialyzer can be used in a dialysis treatment, both must be primed with a sterile saline solution to remove air from the extracorporeal circuit. Once primed, the saline solution is recirculated through the blood tubing set and the dialyzer to produce a stabilized flow and remove additional trapped air from within the extracorporeal circuit. The priming and recirculating process also serves to clean the dialyzer and flush the dialyzer membrane of any debris or chemicals remaining from a prior use.

A commonly used method of creating blood access for hemodialysis is by means of an arteriovenous fistula. For each dialysis session, the fistula must be punctured with large bore needles to deliver blood into, and return blood from, the artificial kidney (dialyzer). Even with the use of anesthetics, the punctures with these large bore needles are painful. Patients undergoing dialysis thus benefit if the punctures can be done as infrequently as possible. Moreover, frequent punctures may be detrimental to the longevity of the fistula.

Existing hemodialysis systems consist fundamentally of two halves; one comprising the extracorporeal blood circuit (the blood flow path) and the other comprising the dialysate circuit or flow path. Typically, the entire blood circuit is disposable and comprises: (1) an arterial and venous fistula needle, (2) an arterial (inflow) and venous (outflow) blood line, (3) a hemodialyzer, (4) one or more physiologic priming solutions (e.g., saline), and (5) one or more anticoagulants (e.g., heparin or citrate).

The arterial fistula needle accesses blood from the patient's fistula and is connected to the arterial blood tubing set, which conveys blood to the dialyzer. The arterial line comprises a pumping segment with interfaces to a blood pump (which may be, e.g., a rotary or peristaltic pump) on the dialysis machine, pressure or flow monitoring chambers including tubing which interfaces to pressure or flow transducers on the machine to monitor the pressure and flow pre-pump and/or post pump, inlet ports for saline and anticoagulant, and one or more injection sites for, e.g., drawing blood or injecting drugs.

The hemodialyzer typically comprises a case which encloses a bundle of hollow fiber semi-permeable membranes, which are usually made from cellulose or synthetic polymers. The blood is circulated on one side of a semipermeable membrane, and the dialysis solution is circulated on the other side, so that the two never come into direct contact. Waste products (uremic toxins) diffuse out of the blood, across the semipermeable membranes, and into the dialysis solution owing to the concentration gradient. Excess water in the patent's blood enters the dialysate as a result of a pressure gradient.

The venous blood line and venous fistula needle carry the newly dialyzed blood away from the dialyzer and back into the patient's circulatory system via a puncture site slightly closer to the heart than the arterial needle site. The venous set is comprised of a pressure monitoring chamber with tubing leading to another pressure transducer in the machine, injection sites, and a segment of tubing which interfaces to an air detection assembly in the machine in order to prevent air emboli during treatment.

A dialysis machine has several systems and components. In an extracorporeal flow path, which conducts blood from the patient to the dialyzer and then back to the patient, at least one arterial blood pump and sometimes a venous blood pump that move the blood and assist in performing certain types of dialysis treatment such as ultrafiltration. A hydraulics flow path, which conducts the dialysate through the dialyzer, includes numerous components to monitor and control the conditions in that flow path. Flow and pressure meters may be included, typically at the inlet and outlet of the dialyzer. A first dialysate pump moves dialysate into the dialyzer, and a second dialysate pump removes the dialysate from the dialyzer. A heater may be included to heat the dialysate to body temperature to avoid undesirable heat transfer to or from the patient, and/or to heat a disinfecting solution to temperatures adequate to kill microorganisms. Other components may be included in dialysis machines designed for specific applications. For example, in ultrafiltration dialysis treatments, an ultrafiltration pump is used to control the delivery of desirable components to the blood.

Proportioning pumps for one or more dialysis solutions may be included. Dialysis solution is typically prepared continuously on-line in present-day machines by combining water which has first been purified by a separate water treatment system, and liquid concentrates of electrolytes. Dialysate concentrates have evolved, from a single formulation which contained acetate as the physiologic buffering agent for the correction of circulatory acidosis, to two container systems where bicarbonate replaces acetate as the buffering agent, and must be kept separate due to its chemical incompatibility with calcium and magnesium. Two proportioning pumps are therefore required, the first to mix the bicarbonate concentrate with water and the second to proportion this mixture with the concentrated electrolytes to achieve the final, physiologically compatible dialysis solution.

The dialysis machine continuously monitors the pressure at the blood inlet and outlet sides of the dialyzer (by way of the pressure transducers connected to the blood sets) as well as in the dialysate circuit. Via microprocessors, the system calculates the transmembrane pressure (TMP) which determines the amount of water transmission through the membranes. Dialysis machines may also comprise a device for measuring the amount of dialysis solution entering and dialysate leaving the dialyzer, which allows the calculation of net water removal from the patient. By electronically comparing the amount of water entering or leaving the blood with the TMP, the system is able to control actively the water removed from the patient to a desired target previously programmed into the system. When low-water-transmission cellulosic membranes are employed, negative pressure is generated on the dialysate side of the membrane by the machine in order to accomplish sufficient water removal. Because suction may be applied to the dialysate as it transits the dialyzer, it is first be placed under a greater vacuum in a degassing chamber so that air bubbles are not generated within the dialyzer that would cause errors in the calculation of ultrafiltration by the flow sensors and also reduce the efficiency of the dialyzer. In contrast, when high-water-transmission, synthetic membranes are used, it is frequently necessary to apply positive pressure on the dialysate side to control the rate of ultrafiltration.

Another non-limiting example of ex vivo therapeutic applications of the invention is the use of the compositions of the invention in devices for the intraoperative and post-surgical salvaging of blood. In this embodiment, a patient's own blood lost during intraoperative and/or post-surgical procedures, is washed and filtered and then reinfused into the patient. For a non-limiting examplary device of this type, see U.S. Pat. No. 5,876,611.

III Molecular Scaffolds and Targetable Constructs

III.A. Structure of Molecular Scaffolds and Targetable Constructs

The targetable construct(s) present in a targetable complex comprises a molecular scaffold which comprises or bears at least two pairs of carrier epitopes recognized by the arm of an antibody or antibody fragment in the complex.

The targetable construct can be of diverse structure, but is selected not only to elicit sufficient immune responses, but also for rapid in vivo clearance when used within the bsAb targeting method. Exemplary targetable constructs for use in the present application are described in U.S. application Ser. No. 09/337,756 filed Jun. 22, 1999, and in U.S. application Ser. No. 09/823,746, filed Apr. 3, 2001, the entire contents of which are incorporated herein by reference.

Hydrophobic agents are best at eliciting strong immune responses, whereas hydrophilic agents are preferred for rapid in vivo clearance, thus, a balance between hydrophobic and hydrophilic needs to be established. This may be accomplished in a preferred approach, in part, by relying on the use of hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may be used. Additionally, the targetable construct can comprise PEG (poly[ethylene] glycol) derivatives to increase its circulation time in a patient.

Peptides having as few as one amine residue may be used, preferably two to ten amino acid residues, if also coupled to other moieties such as chelating agents. Examples include modified amino acids, such as bis-DTPA-lysine, and bis-DTPA-diamine. These agents can be linked covalently to molecules which are to be targeted. The hapten moiety of the carrier portion should be a low molecular weight conjugate, preferably having a molecular weight of 100,000 daltons or less, and advantageously less than about 20,000 daltons, 10,000 daltons or 5,000 daltons, including the metal ions in the chelates. For instance, the known peptide di-indium-DTPA-Tyr-Lys(DTPA)-OH has been used to generate antibodies against the indium-DIVA portion of the molecule. However, by use of the non-indium-containing molecule, and appropriate screening steps, new Abs against the tyrosyl-lysine dipeptide can be made. More usually, the antigenic peptide will have four or more residues, such as the peptide Ac-Phe-Lys(DTPA)-Tyr-Lys(DTPA)-NH$_2$ (SEQ ID NO:1). Again, the non-metal-containing peptide is used as an immunogen, with resultant Abs screened for reactivity against the Phe-Lys-Tyr-Lys (SEQ ID NO:2) backbone. Another non-limiting example of an antigenic peptide having four or more residues is the peptide DOTA-Phe-Lys(HSG)-Tyr-Lys(HSG)-NH$_2$ (SEQ ID NO:3), wherein DOTA is 1,4,7,10-tetraazacyclododecanetetraacetic acid and HSG is the histamine succinyl glycyl group of the formula:

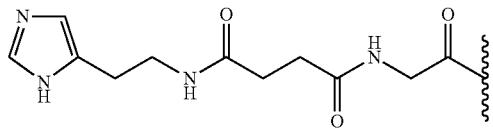

The non-metal-containing peptide may be used as an immunogen, with resultant Abs screened for reactivity against the Phe-Lys-Tyr-Lys (SEQ ID NO:2) backbone.

In one embodiment, unnatural amino acids, e.g., D-amino acids, are incorporated into the backbone structure to ensure that, when used with the final bsAb/linker system, the scFv component which recognizes the linker moiety is completely specific. The invention further contemplates other backbone structures such as those constructed from non-natural amino acids, peptoids, peptidomimetics, aptamers, peptide nucleic acids (PNAs), and the like.

According to one embodiment of the invention, the targetable construct can encompass a carbohydrate. Suitable such carbohydrates include carbohydrate chains of two to six sugar units long. The targetable construct also can comprise a polymeric carbohydrate, such as dextran.

In another embodiment of the invention, the haptens of the targetable construct comprise a known immunogenic recognition moiety, for example, a known hapten. Using a known hapten, for example, fluorescein isothiocyanate (FITC), higher specificity of the targetable construct for the antibody is exhibited. This occurs because antibodies raised to the hapten are known and can be incorporated into the inventive antibody. Thus, binding of the targetable construct with the attached chelator or metal-chelate complex would be highly specific for the inventive antibody or antibody fragment. Another example of a hapten to be substituted onto the targetable construct includes vitamin B12. The use of vitamin B12 is advantageous since anti-B12 Mabs are known and no free serum B12 exists, therefore, great specificity for the antibody may be exhibited. The chelator or its chelate with a metal cation also can function as the hapten to which an antibody is raised. Another example of a hapten to be conjugated to a targetable construct includes biotin.

III.B. Preparation of Molecular Scaffolds and Targetable Constructs

Peptides, including but not limited to, peptides to be used as molecular scaffolds or immunogens are synthesized conveniently on an automated peptide synthesizer using a solid-phase support and standard techniques of repetitive orthogonal deprotection and coupling.

Free amino groups in the peptide that are to be used later for chelate conjugation are advantageously blocked with standard protecting groups such as an Aloc group. Such protecting groups will be known to the skilled artisan. See Greene and Wuts, *Protective Groups in Organic Synthesis*, John Wiley and Sons, New York (1999) and Kates S A, Albericio F. *Solid-Phase Synthesis: A Practical Guide*. Marcel Dekker, New York (2000). Methods of synthesizing amino acid-based polymers and glycosylated peptides are described in, respectively, Sanda and Endo, Syntheses and Functions of Polymers Based on Amino Acids, *Macromol. Chem. Phys.* 200:2651-2661, 1999; and Sears and Wong, Toward automated synthesis of oligosaccharides and glycoproteins, *Science* 291:2344-2350, 2001.

III.C. Chemical Conjugation

Molecular scaffolds may be prepared as a single molecule, or may be generated by first preparing subunits that are then covalently attached to each other. The term "conjugation" is used to indicate the covalent attachment of two or more molecules.

Peptides are conjugated (i.e., linked, or covalently attached), to one another using various methods. By way of non-limiting example, amino acid residues present in the natural sequence of a first peptide can be directly covalently linked to amino acid residues in the natural amino acid sequence of a second peptide as in, e.g., a disulfide bridge; or a cross-linking reagent (also known as "cross-linker"), typically a bifunctional (two-armed) chemical linker that forms covalent linkages between two or more peptides, can be used to covalently link peptides to each other. Such bifunctional linkers can be homobifunctional (wherein both "arms" of the linker are the same chemical moiety) or heterobifunctional (wherein each of the two "arms" is a different chemical moiety than the other).

Hermanson (*Bioconjugate Techniques*, Academic Press, 1996), herein incorporated by reference, summarizes many of the chemical methods used to link proteins and other molecules together using various reactive functional groups present on various cross-linking or derivatizing reagents. Cross-linking agents are based on reactive functional groups that modify and couple to amino acid side chains of proteins and peptides, as well as to other macromolecules. Cross-linking reagents incorporate two or more functional reactive groups. The functional reactive groups in a cross-linking reagent may be the same or different. Many different cross-linkers are available to cross-link various proteins, peptides, and macromolecules. Table 1 lists some of the cross-linkers that are easily available through commercial sources according to their class of chemical reactivity. Table 2 lists some of the properties of chemical cross-linkers and the types of functional groups with which they react.

TABLE 1

CLASSES OF CHEMICAL REACTIVITY OF CROSS-LINKERS AND EXAMPLES OF CROSS-LINKERS

| Chemical reactivity | Abbreviation | Compound |
| --- | --- | --- |
| homobifunctional imidoesters | DMA | Dimethyl adipimidate•2 HCl |
|  | DMP | Dimethyl pimelimidate•2 HCl |
|  | DMS | Dimethyl suberimidate•2 HCl |
|  | DTBP | Dimethyl 3,3'-dithiobispropionimidate•2 HCl |
| homobifunctional N-hydroxysuccinimide esters (NHS-esters) | DSG | Disuccinimidyl glutarate |
|  | DMSC | Dimethyl succmimidate•2 HCl |
|  | DSS | Disuccinimidyl suberate |
|  | BS |  |
|  | DSP | Dithiobis(succinimidylpropionate) |
|  | DTSSP | Dithiobis(sulfosuccinimidylpropionate) |
|  | DTME | Dithio-bis-maleimidoethane |
|  | EGS | Ethylene glycolbis(succinimidylsuccinate) |
|  | Sulfo-EGS | Ethylene glycolbis(sulfosuccinimidylsuccinate) |
|  | DST | Disuccinimidyl tartrate |
|  | Sulfo-DST | Disulfosuccinimidyl tartrate |
|  | BSOCOES | Bis[2-(succinimidooxycarbonyloxy)ethyl]sulfone |
|  | Sulfo-BSCOCOES | Bis[2-(sulfosuccinimidooxycarbonyloxy)ethyl]sulfone |
| heterobifunctional NHS-esters | BS3 | BIS-(sulfosuccinimidyl) suberate |
|  | DMM | dimethyl malonimidate•2 HCl |
|  | EMCS | N-[ε-maleimidocaproyloxy]succinimide ester |
|  | Sulfo-EMCS | N-[ε-maleimidocaproyloxy]sulfosuccinimide ester |
|  | SMCC | succinimidyl 4-(N-maleimidomethyl)cyclohexane-1-carboxylate |
|  | LC-SMCC | succiminidyl-4-(N-maleimidomethyl)cyclohexane-1-carboxy-(6-amido-caproate) |
|  | Sulfo-MBS | m-maleimidobenzoyl-N-hydoxysulfosuccinimide ester |
|  | Sulfo-SMCC | sulfosuccinimidyl 4-(N-maleimidomethyl)cyclohexane-1-carboxylate |
|  | MBS | m-maleimidobenzoyl-N-hydoxysuccinimide ester |
|  | SMPB | succinimidyl 4-[P-Maleimidophenyl] butyrate |
|  | Sulfo-SMPB | sulfosuccinimidyl 4-[p-maleimidophenyl]butyrate |
|  | BMH | bismaleimidohexane |
|  | GMBS | N-[γ-Maleimidobutyryloxy] succinimide ester |
|  | Sulfo-GMBS | N-[γ-Maleimidobutyryloxy] sulfosuccinimide ester |
| heterobifunctional haloacetyl NHS-esters | SIAB | N-succinimidyl(4-iodoacetyl)aminobenzoate |
|  | Sulfo-SIAB | Sulfo-SIAB sulfosuccinimidyl(4-iodoacetyl)aminobenzoate |
| homobifunctional pyridyldithiols | DPDPB | 1,4-Di-[3'-(2'-pyridyldithio)propionamido]butane |
| heterobifunctional pyridyldithiols | SMPT | 4-succinimidyloxycarbonyl-methyl-(2-pyridyldithio)-toluene |
|  | Sulfo-LC-SMPT | sulfosuccinimidyl 6-[a-methyl-a-(2-pyridyl-dithio)toluamido]hexanoate |
|  | SPDP | N-succinimidyl 3-(2-pyridyldithio)propionate |
|  | LC-SPDP | N-succinimidyl 6-[3'-(2-pyridyldithio)propionamido]hexanoate |
|  | Sulfo-LC-SPDP | sulfosuccinimidyl6-[3'-(2-pyridyldithio)-propionamido] hexanoate |
| carboxyl reactive carbonyl reactive | PDPH | 3-(2-Pyridyldithio) propionyl hydrazide |
|  | EDC | 1-ethyl-3-(3-dimethylaminopropyl)-carbodiimide |
|  | M2C2H | 4-(N-Maleimidomethyl)cyclohexane-1-carboxyl hydrazide |
|  | DCC | N,N-dicyclohexylcarbodimide |
|  | MPBH | 4-(4-N-Maleimidophenyl)butyric acid hydrazide hydrochloride |

TABLE 1-continued

CLASSES OF CHEMICAL REACTIVITY OF CROSS-LINKERS AND EXAMPLES OF CROSS-LINKERS

| Chemical reactivity | Abbreviation | Compound |
|---|---|---|
| Photoreactive | ABH | Azidobenzoyl hydrazide |
| | ANB-NOS | N-5-azido-2-nitrobenzoyloxysuccinimide |
| | APDP | N-[4-(p-azidosalicylamido)butyl]-3'(2'-pyridyldithio)propionamide |
| | APG | p-Azidophenylglyoxal monhydrate |
| | ASBA | 4-(p-Azidosalicylamido)butylamine |
| | ASIB | 1-(p-Azidosalicylamido)-4-(iodoaceamido)butane |
| | BASED | Bis-[B-4-azidosalicylamido)ethyl]disulfide |
| | HSAB | N-Hydroxysuccinimidyl-4-azidobenzoate |
| | Sulfo-HSAB | N-Hydroxysulfo-succinimdyl-4-azidobenzoate |
| | NHS-ASA | N-Hydroxysuccinimidyl-4-azidosalicylic acid |
| | Sulfo-NHS-ASA | N-Hydroxysulfo-succinimidly-4-azidosalicylic acid |
| | Sulfo-NHS-LC-ASA | Sulfosuccinimidly-[4-azidosalicylamido)-hexanoate |
| | PNP-DTP | p-Nitropheyno-2-diazo-3,3,3-trifluoropropionate |
| | DTP | 2-Diazo-3,33-trifluoropropionylchloride |
| | SADP | N-succinimidyl-(4-azidopheynyl 1,3' dithiopropionate |
| | Sulfo-SADP | Sulfosuccinimidyl-(4-azidophynyldithio)propionate |
| | SAED | Sulfosuccinimidyl 2(7-azido-4-methylcoumarin-3-acetamide)ethyl-1,3-dithiopropionate |
| | Sulfo-SAMCA | Sulfosuccinimidyl 7-azido-4-methycoumarin-3-acetate |
| | SAND | Sulfosuccinimidyl 2-(m-azido-o-nitrobenzamdio)-ethyl-1,3-dithiopropionate |
| | SANPH | N-succinimidyl-6-(4'-azido-2'-nitrophenylamino)hexanoate |
| | Sulfo-SANPH | Sulfosuccinimidyl 6-(4'-azido-2'-nitrophenylamino)hexanoate |
| | SASD | Sulfosuccinimidyl 2-(p-azdiosalicylamido)ethyl-1,3'-dithiopropionate |
| | Sulfo-SAPB | Sulfosuccinimidyl 4-(p-azidophenyl)-butyrate |
| Heterobifunctional amine reactive | SDBP | N-Hydroxysuccinimidyl 2,3-dibromopropionate |
| Bifunctional aryl halide | DFDNB | 1,5-Difluoro-2.4-dinitrobenzene |
| heterobifunctional nitrophenylsulfonic acid ester | mal-sac-HNSA | maleimido-6-aminocaproyl-ester of 1-hydroxy-2-nitrobenzene-4-sulfonic acid |

TABLE 2

CHEMICAL CROSS-LINKERS AND SOME OF THEIR PROPERTIES

| Acronym | Pierce Product Number | Spacer Arm Length (angstroms) | Links | Cleavable By | Water Soluble | Membrane Permeable |
|---|---|---|---|---|---|---|
| Sulfo-LC-SMPT | 21568 | 20.0 | Amines To Sulfhydryls | Thiols | Yes | No |
| SMPT | 21558 | 20.0 | Amines To Sulfhydryls | Thiols | Yes | No |
| Sulfo-KMUS | 21111 | 19.0 | Amines To Sulfhydryls | non | Yes | No |
| LC-SMCC | 22362 | 16.1 | Amines To Sulfhydryls | non | Yes | No |
| KMUA | 22211 | 15.7 | Amines To Sulfhydryls | non | Yes | No |
| LC-SPDP | 21651 | 15.6 | Amines To Sulfhydryls | non | No | nd |
| Sulfo-LC-SPDP | 21650 | 15.6 | Amines To Sulfhydryls | Thiols | Yes | No |
| SMPB | 22416 | 14.5 | Amines To Sulfhydryls | non | No | Yes |
| Sulfo-SMPB | 22317 | 14.5 | Amines To Sulfhydryls | non | Yes | No |
| SMPH | 22363 | 14.3 | Amines To Sulfhydryls | non | No | nd |
| SMCC | 22360 | 11.6 | Amines to Sulfhydryls | non | No | Yes |
| Sulfo-SMCC | 22322 | 11.6 | Amines to Sulfhydryls | non | Yes | No |

TABLE 2-continued

CHEMICAL CROSS-LINKERS AND SOME OF THEIR PROPERTIES

| Acronym | Pierce Product Number | Spacer Arm Length (angstroms) | Links | Cleavable By | Water Soluble | Membrane Permeable |
|---|---|---|---|---|---|---|
| SIAB | 22329 | 10.6 | Amines to Sulfhydryls | non | No | Yes |
| Sulfo-SIAB | 22327 | 10.6 | Amines To Sulfhydryls | non | Yes | No |
| Sulfo-GMBS | 22324 | 10.2 | Amines To Sulfhydryls | non | Yes | No |
| GMBS | 22309 | 10.2 | Amines To Sulfhydryls | non | No | Yes |
| MBS | 22311 | 9.9 | Amines To Sulfhydryls | non | No | Yes |
| Sulfo-MBS | 22312 | 9.9 | Amines To Sulfhydryls | non | Yes | No |
| Sulfo-EMCS | 22307 | 9.4 | Amines To Sulfhydryls | non | Yes | No |
| EMCA | 22306 | 9.4 | Amines To Sulfhydryls | non | Yes | No |
| EMCS | 22308 | 9.4 | Amines To Sulfhydryls | non | No | Yes |
| SVSB | 22358 | 8.3 | Amines To Sulfhydryls | non | No | Yes |
| BMPS | 22298 | 6.9 | Amines To Sulfhydryls | non | No | nd |
| SPDP | 21857 | 6.8 | Amines To Sulfhydryls | Thiols | No | Yes |
| SBAP | 22339 | 6.2 | Amines To Sulfhydryls | non | No | Yes |
| BMPA | 22296 | 5.9 | Amines To Sulfhydryls | non | Yes | No |
| AMAS | 22295 | 4.4 | Amines To Sulfhydryls | non | No | nd |
| SATP | 26100 | 4.1 | Amines To Sulfhydryls | non | No | Yes |
| SIA | 22349 | 1.5 | Amines To Sulfhydryls | non | No | nd |
| Sulfo-LC-SMPT | 21568 | 20.0 | Sulfhydryls to Amines | Thiols | Yes | No |
| SMPT | 21558 | 20.0 | Sulfhydryls to Amines | Thiols | No | Yes |
| AEDP | 22101 | 9.5 | Carboxyls to Amines | Thiols | Yes | No |
| EDC | 22980 | 0.0 | Carboxyls to Amines | non | Yes | No |

Bifunctional cross-linking reagents may be classified according to their functional groups, chemical specificity, length of the cross bridge that they establish, the presence of similar functional groups or dissimilar functional groups, chemical or photochemical reactivity, ability to be cleaved internally by reduction or other means, and the ability of the reagent to be further modified by radiolabelling (i.e. radioiodination) or addition of detectable tags or labels. The selective groups on the cross-linking reagent can be present in a homo-bifunctional arrangement in which the selective groups are identical, or can be present in a heterobifunctional arrangement in which the selective groups are dissimilar.

The chemical modification may be done using cross-linking reagents containing selective groups that react with primary amines, sulfhydryl (thiol) groups, carbonyl, carboxyl groups, hydroxyl, or carbohydrates and other groups placed on a protein or peptide, especially by posttranslational modifications within the cell. The selective groups include, but are not limited to, imidoester, N-hydroxysuccinimide ester or sulfosuccinimidyl ester, ester of 1-hydroxy-2-nitrobenzene-4-sulfonic, maleimide, pyridyl disulfide, carbodiimide, and haloacetyl groups.

Sulfhydryl reactive functional groups include maleimides, alkyl and aryl halides, haloacyls, haloacetyls and pyridyl disulfides. Maleimides, alkyl and aryl halides, haloacetyls and haloacyls react with thiols to form stable thioether bonds that are not reduced by reagents such as 2-mercaptoethanol and dithiothreitol. Pyridyl disulfides form mixed disulfides with thiol groups, mixed disulfides may be used as an intermediate for cross-linking two or more macromolecules. Cross-linkers that first react with a carboxyl group to form an activated intermediate and then reacts with an amino group, such as an amino group of lysine or an amino group of an amino terminal amino acid, may be used.

A spacer arm or "cross-bridge" region, consisting of a spacer group or a functional group, such as a disulfide bond or hindered disulfide bond, connects the two selective or functional groups. The length of the spacer arm may be varied. The distance between the functional groups establishes the length of the spacer arm. Longer spacer arms may be required to diminish or eliminate steric hindrance between two molecules that are cross-linked together. Intermolecular cross-linking is more efficient with longer spacer arms. Short spacer arms favor intramolecular cross-linking, which is to be avoided in the present invention.

Spacer arms may have reactive bonds within them that enable further modifications. For example, internal cleavable bonds may be placed within the spacer, such as disulfides or hindered disulfides, one or more ester bonds, or vicinal hydroxyl groups. Cleavage of internal disulfide bonds may be achieved using reduction with thiol containing reagents such as 2-mercaptoethanol and dithiothreitol. One or more metabolizable bonds may be inserted internally in the cross-linking reagent to provide the ability for the coupled entities to separate after the bond(s) is broken after the conjugate is transported into the cell and into the body.

Homobifunctional cross-linkers contain at least two identical functional groups. Heterobifunctional cross-linkers contain two or more functional reactive groups that react with different specificity. Because heterobifunctional cross-linkers contain different reactive groups, each end can be individually directed towards different functional groups on proteins, peptides, and macromolecules. This feature results in linking, for example, amino groups on one molecular entity to carboxyl groups on another entity, or amino groups on one entity to sulfhydryl groups on another entity.

Functional groups include reactive portions on proteins, peptides, and macromolecules that are capable of undergoing chemical reaction. Functional groups include amino and carboxyl groups, hydroxyl groups, phenolate hydroxyl groups, carbonyl groups, guanidinyl groups, and carbon-carbon double bonds. In addition, photoactive reagents that become reactive when exposed to light may be used. For example, arylazides may be activated to form activated intermediates, such as an aryl nitrene or a dehydroazepine intermediate, that non-selectively inserts into carbon-hydrogen bonds (i.e. by aryl nitrenes) or reacts with amines (dehydroazepines). Other examples include fluorinated aryl azides, benzophenones, certain diazo compounds, and diazrine derivatives.

If the desired sulfhydryl groups are not present on the protein, peptide or macromolecule, a sulfhydryl may be introduced by chemical modification. As a nonlimiting example, the sFv or a therapeutic macromolecule can be modified so as to introduce a thiol by chemical modification. A cysteine amino acid can be placed in a peptide during peptide synthesis. Sulfhydryl groups can be added by chemical modification using 2-iminothiolane (IT), also known as Traut's reagent.

Sulfhydryl groups can also be added by using a modification reagent that contains a disulfide bond in addition to a group that selectively reacts with primary amines. For example, the heterobifunctional cross-linker sulfosuccinimidyl 6-[3'-(2-pyridyldithio)-propionamido]hexanoate (sulfo-LC-SPDP, Pierce Chemical Co.) will thiolate peptides when used according to the manufacturer's directions. Other, non-soluble, forms such as N-succinimidyl 3-(2-pyridyldithio) propionate (SPDP, Pierce Chemical Co.) or N-succinimidyl 6-[3'-(2-pyridyldithio)propionamido]hexanoate (LC-SPDP, Pierce Chemical Co.) can be used in these reactions by dissolving in a suitable organic solvent to a concentration of 20 mM, and adding 25-1 to 1 ml of 10 mg/ml peptide. Reducing the SPDP-derivatized peptide under mild conditions will release pyridine-2-thione, leaving an aliphatic thiol. An example of a mild reducing condition is to add 1/100th volume of 1M dithiothreitol (DTT) to the above SPDP-derivatized target peptide and incubating for 30 minutes at room temperature, or incubate the SPDP-derivatized target peptide with 50 mM 2-meraptoethylamine in PBS-EDTA for 90 minutes at 37° C. The excess SPDP, LC-SPDP or sulfo-LC-SPDP, and the pyridine-2-thione can then be removed by HPLC purification.

These modification reagents may also contain groups near the added thiol such that they form a hindered disulfide when oxidized. These reagents, such as 4-succinimidyloxycarbonyl-methyl-(2-pyridyldithio)-toluene (SMPT), may result in a conjugate that exhibits increased stability in vivo (Thorpe et al. *Cancer Res.* 47:5924-5931, 1987). Other cross-linking reagents can be used for protein thiolation and are known to those well versed in the art. Many of these reagents are described in the Pierce Chemical Co. catalog, or by Ji, *Meth. Enzymol.* 91:580-609, 1983; and Hermanson, *Bioconjugate Techniques*, Academic Press, Inc., San Diego, 1-785, 1996.

Most commonly, carrier molecule scaffold portions will have either sulfhydryl or primary amines as the targets of the cross-linking reagents, and both sulfhydryl and primary amines can either exist naturally or be the result of chemical modification as described above. When both carrier molecular scaffold portions have a reduced sulfhydryl, a homobifunctional cross-linker that contains maleimide, pyridyl disulfide, or haloacetyl groups can be used for cross-linking. Examples of such cross-linking reagents include, but are not limited to, bismaleimidohexane (BMH) or 1,4-Di-[3'-(2'-pyridyldithio)propionamido]butane (DPDPB). Alternatively, a heterobifunctional cross-linker that contains a combination of maleimide, pyridyl disulfide, or haloacetyl groups can be used for cross-linking. Less preferably, the cross-linking reagent can contain thiophthalimide derivatives or disulfide dioxide derivatives. Also, extrinsic sulfhydryl groups can be introduced into the carrier molecular scaffold portions and oxidized to cross-link by disulfide formation.

When primary amines are selected as the target both on sFv and therapeutic macromolecule, then a homobifunctional cross-linker that contains succinimide ester, imidoester, acylazide, or isocyanate groups can be used for cross-linking. Examples of such cross-linking reagents include, but are not limited to, Disuccinimidyl glutarate (DSG), Dithiobis(succinimidylpropionate) (DSP), Bis[2-(succinimidooxycarbonyloxy)ethyl]sulfone (BSOCOES), Bis[2-(sulfosuccinimidooxycarbonyloxy)ethyl]sulfone (sulfo-BSCOCOES), Disuccinimidyl suberate (DSS), Bis-(Sulfosuccinimidyl) Suberate (BS3), Disuccinimidyl tartrate (DST), Disulfosuccinimidyl tartrate (sulfo-DST), Dithio-bis-maleimidoethane (DTME), Ethylene glycolbis(succinimidylsuccinate) (EGS), Dithiobis(sulfosuccinimidylpropionate) (DTSSP), Ethylene glycolbis(sulfosuccinimidylsuccinate) (sulfo-EGS), Dimethyl malonimidate.2HCl (DMM), Dimethyl succinimidate.2HCl (DMSC), Dimethyl adipimidate.2HCl (DMA), Dimethyl pimelimidate.2HCl (DMP), Dimethyl suberimidate.2HCl (DMS), and Dimethyl 3,3'-dithiobispropionimidate.2HCl (DTBP). Heterobifunctional cross-linkers that contains a combination of imidoester or succinimide ester groups can also be used for cross-linking Heterobifunctional cross-linking reagents that combine selective groups against different targets are generally preferred because these allow reactions to be performed selectively and sequentially, minimizing self-association or polymerization. Also, heterobifunctional reagents allow selection of chemistry appropriate for the individual molecules to be joined. Examples of such cross-linking reagents include, but are not limited to, N-succinimidyl 3-(2-pyridyldithio)propionate (SPDP), N-succinimidyl 6-[3'-(2-pyridyldithio)propionamido]hexanoate (LC-SPDP), sulfosuccinimidyl 6-[3'-(2-pyridyldithio)-propionamido]hexanoate (sulfo-LC-SPDP), m-maleimidobenzoyl-N-hydroxysuccinimide ester (MBS), m-maleimidobenzoyl-N-hydroxysulfosuccinimide ester (sulfo-MBS), succinimidyl 4-[P-maleimidophenyl]butyrate (SMPB), sulfosuccinimidyl 4-[p-maleimidophenyl]butyrate (sulfo-SMPB), N-[Maleimidobutyryloxy]succinimide ester (GMBS), N-[maleimidobutyryloxy]sulfosuccinimide ester (sulfo-GMBS), N-[maleimidocaproyloxy]succinimide ester (EMCS), N-[maleimidocaproyloxy]sulfosuccinimide ester (sulfo-EMCS), N-succinimidyl(4-iodoacetyl)aminobenzoate (SIAB), sulfosuccinimidyl(4-iodoacetyl)aminobenzoate (sulfo-SIAB), succinimidyl 4-(N-maleimidomethyl) cyclohexane-1-carboxylate (SMCC), sulfosuccinimidyl 4-(N-maleimidomethyl)cyclohexane-1-carboxylate (sulfo-SMCC), succiminidyl-4-(N-maleimidomethyl)cyclohexane-1-carboxy-(6-amido-caproate) (LC-SMCC), 4-succinimidyloxycarbonyl-methyl-(2-pyridyldithio) toluene (SMPT), and sulfo-LC-SMPT.

IV. Chelate Moieties

The presence of hydrophilic chelate moieties on the targetable construct helps to ensure rapid in vivo clearance. In addition to hydrophilicity, chelates are chosen for their metal-binding properties, and are changed at will since, at least for those targetable constructs whose bsAb epitope is part of the peptide or is a non-chelated hapten, recognition of the metal-chelate complex is no longer an issue.

The nature of the invention is such that several chelate moities may be used in a targetable construct or complex. For example, if two types of bsAbs are to be used in a complex, each of which has a different binding specificity for a carrier epitope (i.e., each of which binds a different type of chelate moiety), then the targetable construct comprises both types of chelate moieties. Those skilled in the art will be able to choose appropriate chelate moieties depending on the nature and structure of the targetable construct and bsAbs to be used, and the intended application of the targetable constructs and complexes. If need be, scFvs having specificities for novel carrier epitopes can be generated and incorporated into a bsAb.

Particularly useful metal-chelate combinations include 2-benzyl-DTPA and its monomethyl and cyclohexyl analogs, used with $^{47}$Sc, $^{52}$Fe, $^{55}$Co, $^{67}$Ga, $^{68}$Ga, $^{111}$In, $^{89}$Zr, $^{90}$Y, $^{161}$Tb, $^{177}$Lu, $^{212}$Bi, $^{213}$Bi, and $^{225}$Ac for radio-imaging and RAIT. The same chelators, when complexed with non-radioactive metals, such as manganese, iron and gadolinium can be used for MRI, when used along with the bsAbs of the invention. Macrocyclic chelators such as NOTA, DOTA, and TETA are of use with a variety of metals and radiometals, most particularly with radionuclides of gallium, ytrrium and copper, respectively.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers, which are of interest for stably binding nuclides such as $^{223}$Ra for RAIT are encompassed by the invention. Porphyrin chelators may be used with numerous radiometals, and are also useful as certain non-radioactive metal complexes for bsAb-directed immuno-phototherapy. More than one type of chelator may be conjugated to a carrier to bind multiple metal ions, e.g., non-radioactive ions and/or radionuclides. One example is a bis-$^{111}$In-DTPA conjugate that also bears a DOTA-$^{90}$Y chelate. Particularly useful therapeutic radionuclides include, but are not limited to $^{32}$P, $^{33}$P, $^{47}$Sc, $^{64}$Cu, $^{67}$Cu, $^{67}$Ga, $^{90}$Y, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac.

Examplary radioactive metal chelate complexes have been described that use radionuclides such as cobalt-57 (Goodwin et al., U.S. Pat. No. 4,863,713), $^{111}$In (Barbet et al., U.S. Pat. Nos. 5,256,395 and 5,274,076; Goodwin et al., *J. Nucl. Med.*, 33:1366-1372, 1992; Kranenborg et al., *Cancer Res.* (suppl.), 55:5864s-5867s, 1995, and *Cancer* (suppl.) 80:2390-2397, 1997) and $^{68}$Ga (Boden et al., *Bioconjugate Chem.* 6:373-379, 1995; and Schuhmacher et al., *Cancer Res.* 55:115-123, 1995) for radioimmuno-imaging.

Because the Abs were raised against the chelators and metal chelate complexes, they have remarkable specificity for the complex against which they were originally raised. Indeed, the bsAbs of Boden et al. have specificity for single enantiomers of enantiomeric mixtures of chelators and metal-chelate complexes.

Chelators such as those disclosed in U.S. Pat. No. 5,753,206, especially thiosemicarbazonylglyoxylcysteine (TscG-Cys) and thiosemicarbazinyl-acetylcysteine (TscA-Cys) chelators are advantageously used to bind soft acid cations of Tc, Re, Bi and other transition metals, lanthanides and actinides that are tightly bound to soft base ligands, especially sulfur- or phosphorus-containing ligands. It can be useful to link more than one type of chelator to a peptide, e.g., a DTPA or similar chelator for, say In(III) cations, and a thiol-containing chelator, e.g., TscG-Cys, for Tc cations. Because antibodies to a di-DTPA hapten are known (Barbet, U.S. Pat. No. 5,256,395) and are readily coupled to a targeting antibody to form a bsAb, it is possible to use a peptide hapten with non-radioactive diDTPA chelates and another chelate for binding a radioisotope, in a pretargeting protocol, for targeting the radioisotope. One example of such a peptide is Ac-Lys (DTPA)-Tyr-Lys(DTPA)-Lys(TscG-Cys-)-NH$_2$ (SEQ ID NO:4). This peptide can be preloaded with In(III) and then labeled with 99-m-Tc cations, the In(III) ions being preferentially chelated by the DTPA and the Tc cations binding preferentially to the thiol-containing TscG-CysC. Other hard acid chelators such as NOTA, DOTA, TETA and the like can be substituted for the DTPA groups, and Mabs specific to them can be produced using analogous techniques to those used to generate the anti-di-DTPA Mab.

It will be appreciated that two different hard acid or soft acid chelators can be incorporated into the targetable construct, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be radioactive or useful for MRI enhancement, to be incorporated into a targetable construct for eventual capture by a pre-targeted bsAb.

Chelators are coupled to the carrier portion of a targetable construct using standard chemistries. For instance, excess 2-(p-isothiocyanato)benzyl-DTPA is reacted with peptide NH$_2$ groups to form thiourea bonds between the p-isothiocyanate of the chelator and the free 1-α and 6-ε-amino groups of the peptide, when a peptide is the targetable construct. Alternatively, the bis-anhydride of DIVA can be coupled directly to a free amine group on the peptide. The desired chelator-peptide is purified chromatographically and is ready for use as a metal binding agent. Similarly, DOTA is mono-activated at one carboxyl group using a carbodiimide, and two DOTA units are coupled to the peptide's free amino-groups or DOTA tri-t-butyl ester is activated with a carbodiimide and the DOTA units are coupled to the free amines on the peptide. (The protecting groups are removed on cleavage from the resin.) Chelators bearing groups specifically reactive with thiols are used for reaction with peptides such as Ac-Cys-D-Tyr-D-Trp-Gly-D-Cys-Gly-D-Tyr-D-Trp-NH$_2$. Such a chelator is exemplified by 2-(p-bromoacetamido)benzyl-DTPA, which may be used to alkylate the peptide's free thiol groups under mild, neutral conditions.

Chelator-peptide conjugates may be stored for long periods as solids. They may be metered into unit doses for metal-binding reactions, and stored as unit doses either as solids, aqueous or semi-aqueous solutions, frozen solutions or lyophilized preparations. They may be labeled by well-known procedures. Typically, a hard acid cation is introduced as a solution of a convenient salt, and is taken up by the hard acid chelator and possibly by the soft acid chelator. However, later addition of soft acid cations leads to binding thereof by the soft acid chelator, displacing any hard acid cations which may be chelated therein. For example, even in the presence of an excess of non-radioactive $InCl_3$, labeling with $^{99m}Tc(V)$ glucoheptonate or with Tc cations generated in situ with stannous chloride and $Na99m-TcO_4$ proceeds quantitatively on the soft acid chelator. Other soft acid cations such as $^{186}Re$, $^{188}Re$, $^{213}Bi$ and divalent or trivalent cations of Mn, Co, Ni, Pb, Cu, Cd, Au, Fe, Ag (monovalent), Zn and Hg, especially $^{64}Cu$ and $^{67}Cu$, and the like, some of which are useful for radioimmunodiagnosis or radioimmunotherapy, can be loaded onto the carrier peptide by analogous methods. Re cations also can be generated in situ from perrhenate and stannous ions or a prereduced rhenium glucoheptonate or other transchelator can be used. Because reduction of perrhenate requires more stannous ion (typically above 200 μg/mL final concentration) than is needed for the reduction of technetium, extra care needs to be taken to ensure that the higher levels of stannous ion do not reduce sensitive disulfide bonds such as those present in disulfide-cyclized peptides. A convenient way to prepare ReO metal complexes of the TscG-Cys-ligands is by reacting the peptide with $ReOCl_3(P(Ph_3)_2$ but it is also possible to use other reduced species such as $ReO(ethylenediamine)_2$.

Preferred chelators include NOTA, DOTA and Tscg and combinations thereof. These chelators have been incorporated into a chelator-peptide conjugate motif as exemplified in the following constructs:

The chelator-peptide conjugates (d) and (e), above, have been shown to bind $^{68}Ga$ and is thus useful in positron emission tomography (PET) applications.

Chelators are coupled to the linker moieties using standard chemistries which are discussed more fully in the working Examples below. Briefly, the synthesis of the peptide Ac-Lys (HSG)D-Tyr-Lys(HSG)-Lys(Tscg-Cys-)-NH₂ was accomplished by first attaching Aloc-Lys(Fmoc)-OH to a Rink amide resin on the peptide synthesizer. The protecting group abbreviations "Aloc" and "Fmoc" used herein refer to the groups allyloxycarbonyl and fluorenylmethyloxy carbonyl. The Fmoc-Cys(Trt)-OH and TscG were then added to the side chain of the lysine using standard Fmoc automated synthesis protocols to form the following peptide: Aloc-Lys(Tscg-Cys (Trt)-rink resin. The Aloc group was then removed. The peptide synthesis was then continued on the synthesizer to make the following peptide: (Lys(Aloc)-D-Tyr-Lys(Aloc)-Lys (Tscg-Cys(Trt)-)-rink resin. Following N-terminus acylation, and removal of the side chain Aloc protecting groups. The resulting peptide was then treated with activated N-trityl-HSG-OH until the resin gave a negative test for amines using the Kaiser test (Karacay et al., Bioconjugate Chem. 11:842-854, 2000). The synthesis of Ac-Lys(HSG)D-Tyr-Lys(HSG)-Lys(Tscg-Cys-)-NH₂, as well as the syntheses of DOTA-Phe-Lys(HSG)-D-Tyr-Lys(HSG)-NH₂; and DOTA-Phe-Lys (HSG)-Tyr-Lys(HSG)-NH₂ (SEQ ID NO:3) are described in greater detail below.

Chelator-peptide conjugates may be stored for long periods as solids. They may be metered into unit doses for metal-binding reactions, and stored as unit doses either as solids, aqueous or semi-aqueous solutions, frozen solutions or lyophilized preparations. They may be labeled by well-known procedures. Typically, a hard acid cation is introduced as a (a)
```
DOTA-Phe-Lys(HSG)-D-Tyr-Lys(HSG)-NH₂
```

(b)
```
DOTA-Phe-Lys(HSG)-Tyr-Lys(HSG)-NH₂  (SEQ ID NO: 3)
```

(c)
```
Ac-Lys(HSG)D-Tyr-Lys(HSG)-Lys(Tscg-Cys)-NH₂
```

(d)
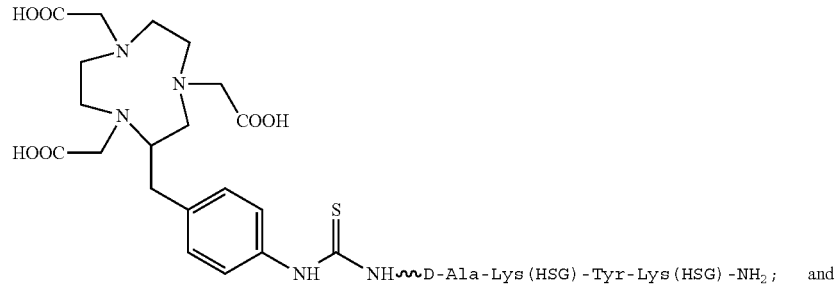

and (e)
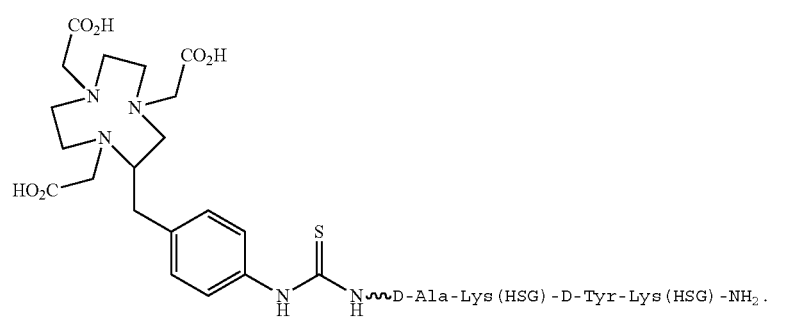

solution of a convenient salt, and is taken up by the hard acid chelator and possibly by the soft acid chelator. However, later addition of soft acid cations leads to binding thereof by the soft acid chelator, displacing any hard acid cations which may be chelated therein. For example, even in the presence of an excess of cold $^{111}$InCl$_3$, labeling with 99m-Tc(V) glucoheptonate or with Tc cations generated in situ with stannous chloride and Na99m-TcO$_4$ proceeds quantitatively on the soft acid chelator. Other soft acid cations such as $^{186}$Re, $^{188}$Re, $^{213}$Bi and divalent or trivalent cations of Mn, Co, Ni, Pb, Cu, Cd, Au, Fe, Ag (monovalent), Zn and Hg, especially $^{64}$Cu and $^{67}$Cu, and the like, some of which are useful for radioimmunodiagnosis or radioimmunotherapy, can be loaded onto the linker peptide by analogous methods. Re cations also can be generated in situ from perrhenate and stannous ions or a prereduced rhenium glucoheptonate or other transchelator can be used. Because reduction of perrhenate requires more stannous ion (typically above 200 μg/mL final concentration) than is needed for the reduction of Tc, extra care needs to be taken to ensure that the higher levels of stannous ion do not reduce sensitive disulfide bonds such as those present in disulfide-cyclized peptides. During radiolabeling with rhenium, similar procedures are used as are used with the Tc-99m. A preferred method for the preparation of ReO metal complexes of the Tscg-Cys-ligands is by reacting the peptide with ReOCl$_3$(P(Ph$_3$))$_2$ but it is also possible to use other reduced species such as ReO(ethylenediamine)$_2$.

V. Biologically Active Moieties

The targetable construct can be conjugated to or complexed with one or more biologically active agents or moieties. The following are non-limiting examples of biologically active moieties and agents.

One type of biologically active agent or moiety is an enzyme capable of activating a prodrug at the target site or improving the efficacy of a normal therapeutic by controlling the body's detoxification pathways. Suitable enzyme includes malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

Following administration of the bsAb, an enzyme conjugated to the carrier is administered. After the enzyme is pre-targeted to the target site, a cytotoxic drug is injected, which is known to act at the target site, or a prodrug form thereof which is converted to the drug in situ by the pre-targeted enzyme. The drug is one which is detoxified to form an intermediate of lower toxicity, most commonly a glucuronide, using the mammal's ordinary detoxification processes. The detoxified intermediate, e.g., the glucuronide, is reconverted to its more toxic form by the pre-targeted enzyme and thus has enhanced cytotoxicity at the target site. This results in a recycling of the drug. Similarly, an administered prodrug can be converted to an active drug through normal biological processes. The pre-targeted enzyme improves the efficacy of the treatment by recycling the detoxified drug. This approach can be adopted for use with any enzyme-drug pair. Similar pre-targeting strategies have been described in U.S. Application Ser. No. 60/101,039. Those methodologies are easily adaptable to the present invention and are hereby incorporated in their entirety by reference.

The enzyme-carrier conjugate can be mixed with the targeting bsAb prior to administration to the patient. After a sufficient time has passed for the enzyme-carrier-bsAb conjugate to localize to the target site and for unbound conjugate to clear from circulation, a prodrug is administered. As discussed above, the prodrug is then converted to the drug in situ by the pre-targeted enzyme.

Certain cytotoxic drugs that are useful for anticancer therapy are relatively insoluble in serum. Some are also quite toxic in an unconjugated form, and their toxicity is considerably reduced by conversion to prodrugs. Conversion of a poorly soluble drug to a more soluble conjugate, e.g., a glucuronide, an ester of a hydrophilic acid or an amide of a hydrophilic amine, will improve its solubility in the aqueous phase of serum and its ability to pass through venous, arterial or capillary cell walls and to reach the interstitial fluid bathing the tumor. Cleavage of the prodrug deposits the less soluble drug at the target site. Many examples of such prodrug-to-drug conversions are disclosed in U.S. application Ser. No. 08/445,110.

Conversion of certain toxic substances such as aromatic or alicyclic alcohols, thiols, phenols and amines to glucuronides in the liver is the body's method of detoxifying them and making them more easily excreted in the urine. One type of anti-tumor drug that can be converted to such a substrate is epirubicin, a 4-epimer of doxorubicin (Adriamycin), which is an anthracycline glycoside and has been shown to be a substrate for human beta-D-glucuronidase. See, e.g., Arcamone, *Cancer Res.* 45:5995, 1985. Other analogues with fewer polar groups are expected to be more lipophilic and show greater promise for such an approach. Other drugs or toxins with aromatic or alicyclic alcohol, thiol or amine groups are candidates for such conjugate formation. These drugs, or other prodrug forms thereof, are suitable candidates for the site-specific enhancement methods of the present invention.

The prodrug CPT-11 (irinotecan) is converted in vivo by carboxylesterase to the active metabolite SN-38. SN-38 is a highly effective anti-tumor agent; however, therapeutic doses can not be administered to patients due to its toxicity. One application of the invention, therefore, is to target such therapies to the tumor site using a bsAb specific for a tumor-associated antigen and a hapten (e.g. di-DTPA) followed by injection of a di-DTPA-carboxylesterase conjugate. Once a suitable tumor-to-background localization ratio has been achieved, the CPT-11 is given and the tumor-localized carboxylesterase serves to convert CPT-11 to SN-38 at the tumor. Due to its poor solubility, the active SN-38 will remain in the vicinity of the tumor and, consequently, will exert an effect on adjacent tumor cells that are negative for the antigen being targeted. This is a further advantage of the method. Modified forms of carboxylesterases have been described and are within the scope of the invention. See, e.g., Potter et al., *Cancer Res.* 58:2646-2651 and 3627-3632, 1998.

Etoposide is a widely used cancer drug that is detoxified to a major extent by formation of its glucuronide and is within the scope of the invention. See, e.g., Hande et al., *Cancer Res.* 48:1829-1834, 1988. Glucuronide conjugates can be prepared from cytotoxic drugs and can be injected as therapeutics for tumors pre-targeted with mAb-glucuronidase conjugates. See, e.g., Wang et al., *Cancer Res.* 52:4484-4491, 1992. Accordingly, such conjugates also can be used with the pre-targeting approach described here. Similarly, designed prodrugs based on derivatives of daunomycin and doxorubicin have been described for use with carboxylesterases and glucuronidases. See, e.g., Bakina et al., *J. Med Chem.* 40:4013-4018, 1997. Other examples of prodrug/enzyme pairs that can be used within the present invention include, but are not limited to, glucuronide prodrugs of hydroxy derivatives of phenol mustards and beta-glucuronidase; phenol mustards or CPT-11 and carboxypeptidase; methotrexate-substituted alpha-amino acids and carboxypeptidase A; penicillin or cephalosporin conjugates of drugs such as 6-mercaptopurine and doxorubicin and beta-lactamase; etoposide phosphate and alkaline phosphatase.

The enzyme capable of activating a prodrug at the target site or improving the efficacy of a normal therapeutic by controlling the body's detoxification pathways may be conjugated to the hapten. The enzyme-hapten conjugate is administered to the patient following administration of the pre-targeting bsAb and is directed to the target site. After the enzyme is localized at the target site, a cytotoxic drug is injected, which is known to act at the target site, or a prodrug form thereof which is converted to the drug in situ by the pre-targeted enzyme. As discussed above, the drug is one which is detoxified to form an intermediate of lower toxicity, most commonly a glucuronide, using the mammal's ordinary detoxification processes. The detoxified intermediate, e.g., the glucuronide, is reconverted to its more toxic form by the pre-targeted enzyme and thus has enhanced cytotoxicity at the target site. This results in a recycling of the drug. Similarly, an administered prodrug can be converted to an active drug through normal biological processes. The pre-targeted enzyme improves the efficacy of the treatment by recycling the detoxified drug. This approach can be adopted for use with any enzyme-drug pair. In an alternative embodiment, the enzyme-hapten conjugate can be mixed with the targeting bsAb prior to administration to the patient. After a sufficient time has passed for the enzyme-hapten-bsAb conjugate to localize to the target site and for unbound conjugate to clear from circulation, a prodrug is administered. As discussed above, the prodrug is then converted to the drug in situ by the pre-targeted enzyme.

One type of biologically active agent or moiety is a prodrug. The pre-targeting bsAb is administered to the patient and allowed to localize to the target and substantially clear circulation. At an appropriate later time, a targetable construct comprising a prodrug, for example poly-glutamic acid (SN-38-ester)$_{10}$, is given, thereby localizing the prodrug specifically at the tumor target. It is known that tumors have increased amounts of enzymes released from intracellular sources due to the high rate of lysis of cells within and around tumors. A practitioner can capitalize on this fact by appropriately selecting prodrugs capable of being activated by these enzymes. For example, carboxylesterase activates the prodrug poly-glutamic acid (SN-38-ester)$_{10}$ by cleaving the ester bond of the poly-glutamic acid (SN-38-ester)$_{10}$ releasing large concentrations of free SN-38 at the tumor. Alternatively, the appropriate enzyme also can be targeted to the tumor site.

After cleavage from the targetable construct, the drug is internalized by the tumor cells. Alternatively, the drug can be internalized as part of an intact complex by virtue of cross-linking at the target. The targetable construct can induce internalization of tumor-bound bsAb and thereby improve the efficacy of the treatment by causing higher levels of the drug to be internalized.

A variety of carriers are well-suited for conjugation to prodrugs, including polyamino acids, such as polylysine, polyglutamic (E) and aspartic acids (D), including D-amino acid analogs of the same, co-polymers, such as poly(Lys-Glu) {poly[KE]}, advantageously from 1:10 to 10:1. Copolymers based on amino acid mixtures such as poly(Lys-Ala-Glu-Tyr) (KAEY; 5:6:2:1) can also be employed. Smaller polymeric carriers of defined molecular weight can be produced by solid-phase peptide synthesis techniques, readily producing polypeptides of from 2-50 residues in chain length. A second advantage of this type of reagent, other than precise structural definition, is the ability to place single or any desired number of chemical handles at certain points in the chain. These can be used later for attachment of recognition and therapeutic haptens at chosen levels of each moiety.

Poly(ethylene) glycol [PEG] has desirable in vivo properties for a bi-specific antibody prodrug approach. Ester linkages between the hydroxyl group of SN-38 and both ends of a standard di-hydroxyl PEG can be introduced by insertion of diacids such as succinic acid between the SN-38 and PEG hydroxyl groups, to generate species such as SN-38-O—CO(CH$_2$)$_2$CO—O-PEG-0-CO(CH$_2$)$_2$CO—OSN-38. The di-SN-38-PEG produced can be considered as the shortest member of the class of SN-38-polymer prodrugs. The desirable in vivo properties of PEG derivatives and the limited loading capacity due to their dimeric functionality led to the preparation of PEG co-polymers having greater hapten-bearing capacity such as those described by Poiani et al. See, e.g., Poiani et al., *Bioconjugate Chem.* 5:621-630, 1994. PEG derivatives are activated at both ends as their bis(succinimidyl)carbonate derivatives and co-polymerized with multi-functional diamines such as lysine. The product of such co-polymerization, containing (-Lys(COOH)—PEG-Lys(COOH)—PEG-), repeat units wherein the lysyl carboxyl group is not involved in the polymerization process, can be used for attachment of SN-38 residues. The SN-38 residues are reacted with the free carboxyl groups to produce SN-38 esters of the (-Lys-(COOH)—PEG-Lys(COOH)—PEG-)$_n$ chain.

Other synthetic polymers that can be used to carry recognition haptens and prodrugs include N-(2-hydroxypropyl) methacrylamide (HMPA) copolymers, poly(styrene-co-maleic acid/anhydride (SMA), poly(divinylether maleic anhydride) (DIVEMA), polyethyleneimine, ethoxylated polyethylene-imine, starburst dendrimers and poly(N-vinylpyrrolidone) (PVP). As an example, DIVEMA polymer comprised of multiple anhydride units is reacted with a limited amount of SN-38 to produce a desired substitution ratio of drug on the polymer backbone. Remaining anhydride groups are opened under aqueous conditions to produce free carboxylate groups. A limited number of the free carboxylate groups are activated using standard water-soluble peptide coupling agents, e.g. 1-ethyl-3-(3-dimethylaminopropyl)carbodiimide hydrochloride (EDC), and coupled to a recognition moiety bearing a free amino group. An example of the latter is histamine, to which antibodies have been raised in the past.

A variety of prodrugs can be conjugated to the carrier portion of the targetable construct. The above exemplifications of polymer use are concerned with SN-38, the active metabolite of the prodrug CPT-11 (irinotecan). SN-38 has an aromatic hydroxyl group that was used in the above descriptions to produce aryl esters susceptible to esterase-type enzymes. Similarly the camptothecin analog topotecan, widely used in chemotherapy, has an available aromatic hydroxyl residue that can be used in a similar manner as described for SN-38, producing esterase-susceptible polymer-prodrugs.

Doxorubicin also contains aromatic hydroxyl groups that can be coupled to carboxylate-containing polymeric carriers using acid-catalyzed reactions similar to those described for the camptothecin family. Similarly, doxorubicin analogs like daunomycin, epirubicin and idarubicin can be coupled in the same manner. Doxorubicin and other drugs with amino 'chemical handles' active enough for chemical coupling to polymeric carriers can be effectively coupled to carrier molecules via these free amino groups in a number of ways. Polymers bearing free carboxylate groups can be activated in situ (EDC) and the activated polymers mixed with doxorubicin to directly attach the drug to the side-chains of the polymer via amide bonds. Amino-containing drugs can also be coupled to amino-pendant polymers by mixing commercially available and cleavable cross-linking agents, such as ethylene glycobis(succinimidylsuccinate) (EGS, Pierce Chemical Co., Rockford, Ill.) or bis[2-(succinimido-oxycarbonyloxy) ethyl]sulfone (BSOCOES, Molecular Biosciences, Huntsville, Ala.), to cross-link the two amines as two amides after reaction with the bis(succinimidyl) ester groups. This is advantageous as these groups remain susceptible to enzymatic cleavage. For example, (doxorubicin-EGS)$_n$-polylysine remains susceptible to enzymatic cleavage of the diester groups in the EGS linking chain by enzymes such as esterases. Doxorubicin also can be conjugated to a variety of peptides, for example, HyBnK(DTPA)YK(DTPA)-NH$_2$, using established procedures (HyBn=p-H$_2$NNHC$_6$H$_4$-CO$_2$H). See Kaneko et al., *J. Bioconjug. Chem.* 2:133-141, 1991.

The therapeutic conjugate may comprise doxorubicin coupled to a carrier comprising amine residues and a chelating agent, such as DTPA, to form a DTPA-peptide-doxorubicin conjugate, wherein the DTPA forms the recognition moiety for a pretargeted bsMAb. Preferably, the carrier comprises a tyrosyl-lysine dipeptide, e.g., Tyr-Lys(DTPA)-NH$_2$, and more preferably still it comprises Lys(DTPA)-Tyr-Lys (DTPA)-NH$_2$. Doxorubicin phenyl hydrazone conjugates to bis-DPTA containing peptides are particularly desirable in a therapeutic context.

Methotrexate also has an available amino group for coupling to activated carboxylate-containing polymers, in a similar manner to that described for doxorubicin. It also has two glutamyl carboxyl groups (alpha and gamma) that can be activated for coupling to amino-group containing polymers. The free carboxylate groups of methotrexate can be activated in situ (EDC) and the activated drug mixed with an amino-containing polymer to directly attach the drug to the sidechains of the polymer via amide bonds. Excess unreacted or cross-reacted drug is separated readily from the polymer-drug conjugate using size-exclusion or ion-exchange chromatography.

Maytansinoids and calicheamicins (such as esperamycin) contain mixed di- and tri-sulfide bonds that can be cleaved to generate species with a single thiol useful for chemical manipulation. The thiomaytensinoid or thioespera-mycin is first reacted with a cross-linking agent such as a maleimido-peptide that is susceptible to cleavage by peptidases. The C-terminus of the peptide is then activated and coupled to an amino-containing polymer such as polylysine.

An immunomodulator, such as a cytokine, may also be conjugated to, or form an alternative or additional biologically active moiety. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18 and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor", and erythropoietin and thrombopoietin. Examples of suitable immunomodulator moieties include IL-2, IL-6, IL-10, IL-12, IL-18, interferon-γ, TNF-α, and the like. Alternatively, subjects can receive invention compositions and a separately administered cytokine, which can be administered before, concurrently or after administration of the invention compositions. The invention compositions may also be conjugated to the immunomodulator.

VI. Combination Therapy

The bi-specific antibody-directed delivery of therapeutics or prodrug polymers to in vivo targets can be combined with bi-specific antibody delivery of radionuclides, such that combination chemotherapy and radioimmunotherapy is achieved. Each therapy can be conjugated to the targetable construct and administered simultaneously, or the nuclide can be given as part of a first targetable construct and the drug given in a later step as part of a second targetable construct. In one simple embodiment, a peptide containing a single prodrug and a single nuclide is constructed. For example, the tripeptide Ac-Glu-Gly-Lys-NH$_2$ can be used as a carrier portion of a targetable construct, whereby SN-38 is attached to the gamma glutamyl carboxyl group as an aryl ester, while the chelate DOTA is attached to the epsilon amino group as an amide, to produce the complex Ac-Glu(SN-38)-Gly-Lys (DOTA)-NH$_2$. The DOTA chelate can then be radiolabeled with various metals for imaging and therapy purposes including In-111, Y-90, Sm-153, Lu-177 and Zr-89. As the metal-DOTA complex may represent the recognizable hapten on the targetable construct, the only requirement for the metal used as part of the DOTA complex is that the secondary recognition antibody also used recognizes that particular metal-DOTA complex at a sufficiently high affinity. Generally, this affinity (log K$_a$) is between 6-11. Polymeric peptides such as poly[Glu(SN-38)$_{10}$-Lys(Y-90-DOTA)$_2$] can be given as readily as the more chemically defined lower MW reagent above, and are indeed preferred. Also, triply substituted polymers can be used, such as poly[Glu(Sn-38)$_{10}$-Lys(Y-90-DOTA)$_n$(histamine-succinate)$_m$, where n and m are integers, such that the recognition agent is independent of the radioimmunotherapy agent. The prodrug is activated by carboxylesterases present at the tumor site or by carboxylesterases targeted to the site using a second targetable construct.

Alternatively, a combination therapy can be achieved by administering the chemotherapy and radioimmunotherapy agents in separate steps. For example, a patient expressing CEA-tumors is first administered bsAb with at least one arm which specifically binds CEA and at least one other arm which specifically binds the targetable construct whose hapten is a conjugate of yttrium-DOTA. Later the patient is treated with a targetable construct comprising a conjugate of yttrium-DOTA-beta-glucuronidase. After sufficient time for bsAb and enzyme localization and clearance, a second targetable construct, comprising Ac-Glu(SN-38)-Gly-Lys(Y-90-DOTA)-NH$_2$, is given. The second targetable construct localizes to the tumor by virtue of bsAb at the tumor that are not already bound to a first targetable construct. First targetable constructs which are localized to the target site act on the Ac-Glu(SN-38)-Gly-Lys(Y-90-DOTA)-NH$_2$ to liberate the free SN-38 drug. Localization of both the prodrug and its respective enzyme to the target site enhances the production of active drug by ensuring that the enzyme is not substrate limited. This embodiment constitutes a marked improvement of current prodrug methodologies currently practiced in the art.

Another advantage of administering the prodrug-polymer in a later step, after the nuclide has been delivered as part of a previously given targetable construct, is that the synergistic effects of radiation and drug therapy can be manipulated and, therefore, maximized. It is hypothesized that tumors become more 'leaky' after RAIT due to radiation damage. This can allow a polymer-prodrug to enter a tumor more completely and deeply. This results in improved chemotherapy.

Alternatively, the RAIT therapy agent can be attached to bsAb rather the targetable construct. For example, an anti-CEA x anti-DTPA bsAb conjugated to Y-90-DOTA is administered first to a patient with CEA-expressing tumors. In this instance, advantage is taken of the selectivity of certain anti-chelate mabs in that an anti-indium-DTPA antibody do not bind to a yttrium-DOTA chelate. After the Y-90-DOTA-anti-CEA x anti-indium-DIVA has maximized at the tumor and substantially cleared non-target tissue, a conjugate of indium-DTPA-glucuronidase is injected and localized specifically to the CEA tumor sites. The patient is then injected with a polymer-prodrug such as poly(Glu)(SN-38)$_{10}$. The latter is cleaved selectively at the tumor to active monomeric SN-38, successfully combining chemotherapy with the previously administered RAIT.

It should also be noted that a bi-specific antibody or antibody fragment can be used in the present method, with at least one binding site specific to an antigen at a target site and at least one other binding site specific to an enzyme. Such an antibody can bind the enzyme prior to injection, thereby obviating the need to covalently conjugate the enzyme to the antibody, or it can be injected and localized at the target site and, after non-targeted antibody has substantially cleared from the circulatory system of the mammal, enzyme can be injected in an amount and by a route which enables a sufficient amount of the enzyme to reach the pre-targeted bsAb and bind to it to form an antibody-enzyme conjugate in situ.

VII. Kits

In accordance with yet another aspect of the present invention, the present invention provides a kit suitable for treating or identifying diseased tissues in a patient, comprising a bi-specific antibody or antibody fragment having at least one arm that specifically binds a targeted tissue and at least one other arm that specifically binds a targetable construct, a first targetable construct which comprises a carrier portion which comprises or bears at least one epitope recognizable by the at least one other arm of the bi-specific antibody or antibody fragment, and one or more conjugated therapeutic agents, or enzymes, and, optionally, a clearing composition useful for clearing non-localized antibodies and antibody fragments.

A "clearing agent" is an agent that clears unbound targetable construct from circulation, thereby facilitating circulating moiety from a patient's body, removal from blood circulation, or inactivation thereof in circulation. Preferably, the clearing agent has physical properties, such as size, charge, configuration or combinations thereof, that limit clearing agent access to the population of target cells recognized by a targetable construct used in the same treatment protocol as the clearing agent. This enhancement may be further improved by the administration of an anti-idiotypic clearing agent, such as an anti-idiotypic monoclonal antibody specific for the determinant of the targeting conjugate, which binds to the tumor site. The clearance effect may be further enhanced by using a galactosylated clearing agent, because a galactosylated clearing agent is rapidly cleared through the liver.

When the first targetable construct comprises an enzyme, the kit may optionally contain a prodrug, when the enzyme is capable of converting the prodrug to a drug at the target site, a drug which is capable of being detoxified in the patient to form an intermediate of lower toxicity, when the enzyme is capable of reconverting the detoxified intermediate to a toxic form, and, therefore, of increasing the toxicity of the drug at the target site, or a prodrug which is activated in the patient through natural processes and is subject to detoxification by conversion to an intermediate of lower toxicity, when the enzyme is capable of reconverting the detoxified intermediate to a toxic form, and, therefore, of increasing the toxicity of the drug at the target site, or a second targetable construct which comprises a carrier portion which comprises or bears at least one epitope recognizable by the at least one other arm of the bi-specific antibody or antibody fragment, and a prodrug, when the enzyme is capable of converting the prodrug to a drug at the target site. Instruments which facilitate identifying or treating diseased tissue also can be included in the kit. Examples include, but are not limited to application devices, such as syringes.

A therapeutic kit of the invention comprises any of the following reagents and/or components in any combination.

1. One or more therapeutic agents.
2. If the therapeutic agent(s) are not formulated for delivery via the alimentary canal, which includes but is not limited to sublingual delivery, a device capable of delivering the therapeutic agent through some other routes. One type of device for parenteral delivery is a syringe that is used to inject the therapeutic agent into the body of an animal in need of the therapeutic agent. Inhalation devices may also be used.
3. Separate containers, each of which comprises one or more reagents of the kit. In a preferred embodiment, the containers are vials contain sterile, lyophilized formulations of a therapeutic composition that are suitable for reconstitution. Other containers include, but are not limited to, a pouch, tray, box, tube, or the like. Kit components may be packaged and maintained sterilely within the containers.
4. Instructions to a person using a kit for its use. The instructions can be present on one or more of the kit components, the kit packaging and/or a kit package insert. Such instructions include, by way of non-limiting example, instructions for use of the kit and its reagents, for reconstituting lyophilized reagents or otherwise preparing reagents.

A preferred kit of the present invention comprises the elements useful for performing an immunoassay. A kit of the present invention can comprise one or more experimental samples (i.e., formulations of the present invention) and one or more control samples bound to at least one pre-packed dipstick or ELISA plate, and the necessary means for detecting immunocomplex formation (e.g., labelled secondary antibodies or other binding compounds and any necessary solutions needed to resolve such labels, as described in detail above) between antibodies contained in the bodily fluid of the animal being tested and the proteins bound to the dipstick or ELISA plate. It is within the scope of the invention that the kit can comprise simply a formulation of the present invention and that the detecting means can be provided in another way.

VIII. Characterization of Targetable Constructs and Complexes

Any of the following methodologies, as well as others known in the art and/or described in the Examples herein, can be used to examine one or more attributes of a targetable construct or complex.

VIII.A. Affinity for Epitopes

Affinity can be either absolute or relative. By absolute affinity, it is meant that the assay for affinity gives defined numerical determinations of the affinity of one compound for another. Comparison of the affinity of the complex being tested to that of a reference compound whose binding affinity is known allows for the determination of relative binding affinity of the test ligand.

Whether absolute or relative, affinity of one molecule for another can be measured by any method known in the art. By way of non-limiting example, such methods include competition assays, surface plasmon resonance, half-maximal binding assays, competition assays, Scatchard analysis, direct force techniques (Wong et al., Direct force measurements of the streptavidin-biotin interaction, *Biomol. Eng.* 16:45-55, 1999), and mass spectrometry (Downard, Contributions of mass spectrometry to structural'immunology, *J. Mass Spectrom.* 35:493-503, 2000).

VIII.A.1. Absolute Affinity

As regards absolute affinity, "low affinity" refers to binding wherein the association constant (Ka) between two molecules is about $10^5$ M to $10^7$ M. "Moderate affinity" refers to binding wherein the association constant (Ka) between two molecules is at least about $10^7$ M to $10^8$ M. "High affinity" refers to a binding wherein the association constant between the two molecules is at least about $10^8$ M to about $10^{14}$ M, and preferably about $10^9$ M to about $10^{14}$ M, more preferably about $10^{10}$ M to about $10^{14}$ M, and most preferably greater than about $10^{14}$ M.

The dissociation constant, Kd, is an equilibrium constant for the dissociation of one species into two, e.g., the dissociation of a complex of two or more molecules into its components, for example, dissociation of a substrate from an enzyme. Exemplary Kd values for compositions of the present invention are from about $10^{-7}$ M (100 nM) to about $10^{-12}$ M (0.001 nM). The stability constant is an equilibrium constant that expresses the propensity of a species to form from its component parts. The larger the stability constant, the more stable is the species. The stability constant (formation constant) is the reciprocal of the instability constant (dissociation constant).

The affinity of the complexes of the invention for a target epitope, or the affinity of a bi-specific antibody for a carrier epitope, is driven by non-covalent interactions. There are four main non-covalent attractive forces between molecules: (i) electrostatic forces, which occur between between oppositely charged molecules such as amino groups and carboxylic groups; (ii) hydrogen bonds, which are formed when hydrogen atoms are shared between electronegative atoms such as nitrogen and oxygen; (iii) Van der Waals forces, which are generated between electron clouds around molecules oppositely polarized by neighboring atoms; and (iv) hydrophobic interactions, which are formed when water is excluded from the interface allowing hydrophobic molecules to interact in a waterless environment.

Non-covalent interactions can, but rarely do, have the strength of a covalent linkage (i.e., a chemical bond). In some instances, the affinity of the complexes of the invention for a target epitope, although driven by non-covalent interactions, is so high as to approach the strength of a covalent bond. This provides for complexes that are very stable relative to other complexes.

Preferably, the affinity of a targetable complex for its cognate target epitope, and/or the affinity of a bsAb for the carrier epitopes of a targetable construct, is a Kd of about 100 nM to about 0.01 nM; more preferably, greater than about 100 nM, or greater than about 10 nM; most preferably, greater than about 1 nM, or greater than about 0.1 nM. Typical Kd for target epitopes are from about 0.1 nM to 100 nM, preferably from about 0.1 nM to 10 nM, more preferably from about 0.5 nM to 5 nM, or about 1 nM.

In the invention, when multiple copies of a carrier epitope are present on the targetable construct, the affinity of an antibody for its cognate carrier epitope may be greater than the affinity of an antibody for a free carrier epitope or for a monovalent tragetable construct comprising the carrier epitope. Additionally or alternatively, a multivalent targetable construct having x carrier epitopes has a greater affinity for its target epitope than would x number of constructs. Put another way, the compositions of the invention provide for synergistic, rather than merely additive, binding effects.

VIII.A.2. Surface Plasmon Resonance

Binding parameters such as Kd may be measured using surface plasmon resonance on a chip, for example, with a BIACORE® chip coated with immobilized binding components. Surface plasmon resonance is used to characterize the microscopic association and dissociation constants of reaction between an antibody or antibody fragment and its ligand. Such methods are generally described in the following references which are incorporated herein by reference. (Vely et al., BIACORE® analysis to test phosphopeptide-SH2 domain interactions, Meth. Mol. Biol. 121:313-21, 2000; Liparoto et al., Biosensor analysis of the interleukin-2 receptor complex, J. Mol. Recog. 12:316-21, 1999; Lipschultz et al., Experimental design for analysis of complex kinetics using surface plasmon resonance, Methods 20:310-8, 2000; Malmqvist., BIACORE®: an affinity biosensor system for characterization of biomolecular interactions, Biochem. Soc. Transactions 27:335-40, 1999; Alfthan, Surface plasmon resonance biosensors as a tool in antibody engineering, Biosensors & Bioelectronics 13:653-63, 1998; Fivash et al., BIACORE® for macromolecular interaction, Curr. Opin. Biotech. 9:97-101, 1998; Price et al., Summary report on the ISOBM TD-4 Workshop: analysis of 56 monoclonal antibodies against the MUC1 mucin, Tumour Biol. 19 Suppl 1:1-20, 1998; Malmqvist et al., Biomolecular interaction analysis: affinity biosensor technologies for functional analysis of proteins, Curr. Opin. Chem. Biol. 1:378-83, 1997; O'Shannessy et al., Interpretation of deviations from pseudo-first-order kinetic behavior in the characterization of ligand binding by biosensor technology, Anal. Biochem. 236:275-83, 1996; Malmborg et al., BIACORE ® as a tool in antibody engineering, J. Immunol. Meth. 183:7-13, 1995; Van Regenmortel, Use of biosensors to characterize recombinant proteins, Dev. Biol.Standardization 83:143-51, 1994; O'Shannessy, Determination of kinetic rate and equilibrium binding constants for macromolecular interactions: a critique of the surface plasmon resonance literature, Curr. Opin. Biotechnol. 5:65-71, 1994). Models using BIACORE® to examine the binding of fixed ligands to multivalent compounds have been described (Muller et al., Model and simulation of multivalent binding to fixed ligands, Anal. Biochem. 261:149-158, 1998).

BIAcore® uses the optical properties of surface plasmon resonance (SPR) to detect alterations in protein concentration bound within to a dextran matrix lying on the surface of a gold/glass sensor chip interface, a dextran biosensor matrix. In brief, proteins are covalently bound to the dextran matrix at a known concentration and a ligand for the protein (e.g., antibody) is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g., by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

Additional details may be found in Jonsson et al., Introducing a biosensor based technology for real-time biospecific interaction analysis, *Ann. Biol. Clin.* 51:19-26, 1993; Jonsson et al., Real-time biospecific interaction analysis using surface plasmon resonance and a sensor chip technology, *Biotechniques* 11:620-627, 1991; Johnsson et al., Comparison of methods for immobilization to carboxymethyl dextran sensor surfaces by analysis of the specific activity of monoclonal antibodies, *J. Mol. Recog.* 8:125-131, 1995; and Johnsson, Immobilization of proteins to a carboxymethyldextran-modified gold surface for biospecific interaction analysis in surface plasmon resonance sensors, *Anal. Biochem.* 198:268-277, 1991; Karlsson et al., Kinetic analysis of monoclonal antibody-antigen interactions with a new biosensor based analytical system, *J. Immunol. Meth.* 145:229, 1991; Weinberger et al., Recent trends in protein biochip technology, *Pharmacogenomics* 1:395-416, 2000; Lipschultz et al., Experimental design for analysis of complex kinetics using surface plasmon resonance, *Methods* 20:310-8, 2000.

VIII.A.3. Relative Affinity

Affinity may also be defined in relative terms, e.g., by $IC_{50}$. In the context of affinity, the $IC_{50}$ of a compound is the concentration of that compound at which 50% of a reference ligand is displaced from a target epitope in vitro or targeted tissue in vivo. When the target epitope is CEA, the reference ligand can be a complex comprising the hMN-14IgG-(734scFv)$_2$ or hMN-14IgG$^{(I253A)}$-(734scFv)$_2$ bi-specific antibody. Typically, $IC_{50}$ is determined by competitive ELISA.

VIII.B. Biodistribution and Clearing Characteristics

Methods of evaluating biodistribution patterns of targetable complexes are described in U.S. provisional Application Ser. No. 60/361,037, which was filed Mar. 1, 2002 and is entitled "Bispecific antibody point mutations for enhancing rate of clearance." This application is hereby incorporated in its entirety by reference.

Methods of evaluating clearing characteristics of targetable complexes are described in U.S. Provisional Application Ser. No. 60/361,037, which was filed Mar. 1, 2002 and is entitled "Bispecific antibody point mutations for enhancing rate of clearance." This application is hereby incorporated in its entirety by reference.

VIII.C. Formation of Defined Species of Multimers

It is often the case that mixing several compounds that are capable of binding to each other results in a variety of multimers. For example, mixing binding compounds A and B can result in species of complexes such as AB, (AB)$_2$, (AB)$_3$, (AB)$_4$, etc. A desirable attribute of some of the complexes of the invention is that the components thereof, when mixed together, predominately form a single type of multimer. In the case of some of the complexes of the invention, for example, dimeric complexes are predominately formed with little or no other species of multimers being present.

For example, mixing a targetable construct and one type bi-specific antibodies at relative concentrations ranging anywhere from about $10^{-9}$, $10^{-8}$, $10^{-7}$, $10^{-6}$, $10^{-5}$, $10^{-4}$, $10^{-3}$, $10^{-2}$, $10^{-1}$, 1, $10^1$, $10^2$, $10^3$, $10^4$, $10^5$, $10^6$, $10^7$, $10^8$, $10^9$ to about $10^{10}$ preferably results in a mixture in which greater than about 50% of the multimeric complexes have a defined stoichiometry of two molecules of the bi-specific antibody, and one molecule of the targetable construct. Preferably ≧75% to about ≧85%, more preferably ≧95%, and most preferably ≧99% of the multimeric complexes so formed have a defined stoichiometry of two molecules of the bi-specific antibody, and one molecule of the targetable construct.

VIII.D. Stability

VIII.D.1. Types of Stability

In general, two types of stability are of interest: chemical stability and conformational stability. Both types contribute to functional stability: an agent may be chemically stable (i.e., resistant to degradation) but may not be biologically active if it does not have the proper conformation. The term "functional stability" refers to the amount of functional (biologically active) agent that is retained over time.

Chemical stability is measured as is known in the art, e.g., by preparing a mixture of labeled agent, incubating the mixture under a given set of conditions (temperature, pH, etc.), and determining the amount of labeled agent remaining in samples taken at one or more time points. In addition to physiological conditions (see below), conditions of interest may be those that influence the shelf-life of an agent and/or ease of manipulation thereof. The stability of an agent as regards a specific degradative molecule, e.g., in the case of proteins, proteases, can be determined in vitro using similar methodologies.

Conformational stability can be measured using a variety of techniques known in the art including, by way of non-limiting example, circular dichroism (CD), fluorescence, fluorescent energy transfer (FRET), fluorescent energy transfer confocal microscopy, nuclear magnetic resonance (NMR) spectroscopy, neutron scattering, synchrotron radiolysis, mass spectrometry, and electrospray ionization mass spectrometry. See, for example, van Mierlo and Steensma, Protein folding and stability investigated by fluorescence, circular dichroism (CD), and nuclear magnetic resonance (NMR) spectroscopy: the flavodoxin story, *J. Biotechnol.* 79:281-98, 2000; Tehei et al., Fast dynamics of halophilic malate dehydrogenase and BSA measured by neutron scattering under various solvent conditions influencing protein stability, *Proc. Natl. Acad. Sci. USA.* 98:14356-61, 2001; Maleknia and Downard, Unfolding of apomyoglobin helices by synchrotron radiolysis and mass spectrometry, *Eur. J. Biochem.* 268:5578-88, 2001; Kim et al., Site-specific amide hydrogen/deuterium exchange in *E. coli* thioredoxins measured by electrospray ionization mass spectrometry, *J. Am. Chem. Soc.* 123:9860-6, 2001; Doig et al., Structure, stability and folding of the alpha-helix, *Biochem. Soc. Symp.* 68:95-110, 2001; Kolakowski and Konermann, From small-molecule reactions to protein folding: studying biochemical kinetics by stopped-flow electrospray mass spectrometry, *Anal. Biochem.* 292:107-14, 2001; Helfrich and Jones, High-throughput flow-injection technique for stability sensing characterization of biomolecules in solution, *Am. Laboratory* 33:24-29, 2001; Hammarstrom et al., Protein compactness measured by fluorescence resonance energy transfer: Human carbonic anhydrase ii is considerably expanded by the interaction of GroEL, *J. Biol. Chem.* 276:21765-75, 2001; Talaga et al., Dynamics and folding of single two-stranded coiled-coil peptides studied by fluorescent energy transfer confocal microscopy, *Proc. Natl. Acad. Sci. USA* 97:13021-6, 2000; and Kumar and Nussinov, Review: How do thermophilic proteins deal with heat? *Cell. Mol. Life. Sci.* 58:1216-1233, 2001.

In addition to the conformational stability of individual components of the targetable complexes (e.g., targetable constructs and bsAbs), the stability of the targetable complexes per se is also a factor. Preferably, the targetable complexes of the invention are stable in vitro and in vivo. That is, once the targetable constructs and bsAbs are combined and form targetable complexes, the constructs and bsAbs have little tendency to dissociate from the complexes.

VIII.D.2. Stability Under Physiological Conditions

Another desirable attribute of a compound intended for in vivo use is stability particularly under physiological conditions. As those in the art will appreciate, what constitutes "physiological conditions" will vary, for example, depending on whether an in vivo or ex vivo state is under consideration, the type of organism and its age, weight, health, sex, level of activity, metabolic state, etc. Parameters that vary in various physiological conditions include, but are not limited to, the type of solvent, pH, buffering capacity, the concentrations and types of salts and ions, temperature, and the like. In any event, it is well within the skill of the ordinary artisan to define and determine what particular conditions exist for a given physiological state.

The stability of a compound can be expressed as the compound's half-life in a body fluid such as, by way of non-limiting example, serum, blood, urine, lymph, plasma, interstitial fluid, bile, gastric juices and the like. By way of non-limiting example, stability can be measured and expressed as the in vivo or in vitro half-life of a compound in serum or blood.

For example, serum half-life is a time point at which half of the administered amount of targeting protein or conjugate thereof remains in the serum. Serum determinations over a series of time points can generate a curve which is useful for determining whole body exposure to an agent.

IX. Biosensors

IX.A. Biosensors in General

The present invention is directed to a device that comprises a sensor adapted to detect one or more specific health and/or nutrition markers in a subject or in the environment. The device may also signal the caretaker, the subject, or an actuator of the occurrence. The sensor comprises a biosensor. As used herein, the term "biosensor" is defined as a component comprising one or more binding moities being adapted to detect a ligand found in one or more target pathogenic microorganisms or related biomolecules.

Generally, biosensors function by providing a means of specifically binding, and therefore detecting, a target biologically active analyte. In this way, the biosensor is highly selective, even when presented with a mixture of many chemical and biological entities. Often the target biological analyte is a minor component of a complex mixture comprising a multiplicity of biological and other components. Thus, in many biosensor applications, detection of target analytes occurs in the parts-per-billion, parts-per-trillion, or even lower ranges levels.

IX.B. Biosensor Design

The biosensor of the present invention may comprise a bio-recognition element, or molecular recognition element, that provides the highly specific binding or detection selectivity for a particular analyte. The bio-recognition element or system is often an antibody. In a biosensor of the invention, the bio-recognition element, or system, is a targetable complex comprising bsAbs. The bio-recognition element is responsible for the selective recognition of the analyte and the physico-chemical signal that provides the basis for the output signal.

Biocatalytic and bioaffinity biosensor systems are described in more detail in *J. Chromatography* 510:347-354, 1990, and in the *Kirk-Othmer Encyclopedia of Chemical Technology*, 4.sup.th ed. (1992), John Wiley & Sons, NY, each of which is incorporated by reference herein.

The biosensors of the present invention may detect biologically active analytes related to impending (i.e., future presentation of symptoms is likely) or current human systemic disease states, including, but not limited to, pathogenic bacteria, parasites (e.g., any stage of the life cycle, including eggs or portions thereof, cysts, or mature organisms), viruses, fungi, antibodies to pathogens, and/or microbially produced toxins. Additionally, the biosensor may target biologically active analytes related to impending or current localized health issues, such as stress proteins (e.g., cytokines) and interleukin 1-alpha that may precede the clinical presentation of skin irritation or inflammation. In some embodiments, the biosensor functions as a proactive sensor, detecting and signaling the subject, a caretaker or medical personnel of the impending condition prior to the presentation of clinical symptoms. This allows time to administer prophylactic or remedial treatments to the subject which can significantly reduce, if not prevent, the severity and duration of the symptoms. Further, the sensor, by detecting the presence of a target biological analyte in a sample from the subject, may detect residual contamination on a surface, such as skin or environmental surface, in contact with the biosensor, and provide and appropriate signal.

The physico-chemical signal generated by the bio-recognition element or elements may be communicated visually to the caretaker or medical personnel (i.e., via a color change visible to the human eye). Other embodiments may produce optical signals, which may require other instrumentation to enhance the signal. These include flourescence, bioluminesence, total internal reflectance resonance, surface plasmon resonance, Raman methods and other laser-based methods, such as LED or laser diode sensors. Exemplary surface plasmon resonance biosensors are available as IBIS I and IBIS II from XanTec Analysensysteme of Muenster, Germany, which may comprise bioconjugate surfaces as bio-recognition elements. Alternatively, the signal may be processed via an associated transducer which, for example, may produce an electrical signal (e.g., current, potential, inductance, or impedance) that may be displayed (e.g., on a readout such as an LED or LCD display) or which triggers an audible or tactile (e.g., vibration) signal or which may trigger an actuator, as described herein. The signal may be qualitative (e.g., indicating the presence of the target biological analyte) or quantitative (i.e., a measurement of the amount or concentration of the target biological analyte). In such embodiments, the transducer may optionally produce an optical, thermal or acoustic signal. In any event, the signal may also be durable (i.e., stable and readable over a length of time typically at least of the same magnitude as the usage life of the device) or transient (i.e., registering a real-time measurement). Additionally, the signal may be transmitted to a remote indicator site (e.g., via a wire, or transmitter, such as an infrared or rf transmitter) including other locations within or on the device or remote devices. Further, the sensor, or any of its components, may be adapted to detect and/or signal only concentrations of the target biological analyte above a predefined threshold level (e.g., in cases wherein the target biological analyte is normally present in the bodily waste or when the concentration of the analyte is below a known "danger" level).

The target analytes that the biosensors of the present invention are adapted to detect may also be viruses. An exemplary biosensor adapted to detect HIV is described in U.S. Pat. Nos. 5,830,341 and 5,795,453, referenced above. The disclosure of each of these patents is incorporated by reference herein. Biosensors are adopted to use in different tissues; see, e.g., U.S. Pat. No. 6,342,037; and using different binding molecules, see, e.g., U.S. Pat. No. 6,329,160.

When the targetable complexes of the invention are incorporated into a biosensor, they may be immobilized in the biosensor by techniques known in the art such as entrapment, adsorption, crosslinking, encapsulation, covalent attachment, any combination thereof, or the like. Further, the immobilization can be carried out on many different substrates such as known the art. In certain preferred embodiments, the immobilization substrate may be selected from the group of polymer-based materials, hydrogels, tissues, nonwoven materials or woven materials.

In certain embodiments, biosensor embodiments, may comprise, be disposed on, or be operatively associated with a microchip, such as a silicon chip, MEMs (i.e., micro electromechanical system) device, or an integrated circuit. Microchip-based biosensors may be known as "biochips." Regardless of the type of sensor, the microchip may comprise a multiplicity of sensor components having similar or different sensitivities, kinetics, and/or target analytes (i.e., markers) in an array adapted to detect differing levels or combinations of the analyte(s). Further, each sensor in such an array may provide a different type of signal, including those types disclosed herein, and may be associated with different actuators and/or controllers. Also, each sensor in an array may operate independently or in association with (e.g., in parallel, combination, or series) any number of other sensors in the array.

A biosensor of the invention may comprise a detectable compound that produces a signal once analytes are bound. See, by way of non-limiting example, Billinton et al., Development of a green fluorescent protein reporter for a yeast genotoxicity biosensor, *Biosensors & Bioelectronics* 13:831-838, 1998. A biosensor according to the invention may use microbalance sensor systems (Hengerer et al., Determination of phage antibody affinities to antigen by a microbalance sensor system, *BioTechniques* 26:956-964, 1999).

X. Target Antigens and Epitopes

A target epitope is comprised within, displayed by and/or released from targeted tissues of a subject, samples or cell cultures thereof. A sample may be a bodily tissue or fluid tissue and may be within a subject, or biopsied or removed from a subject, or a whole or any portion of a bodily organ. Additionally, the tissue may be "sample" in that the tissue is recently removed from a subject without any preservation steps between the excision and the methods of the current invention. The tissue may also have been preserved by such standard tissue preparation techniques including, but not limited to, freezing, quick freezing, paraffin embedding and tissue fixation, prior to application of the methods of the current invention.

As used herein, the term "subject" refers to any animal (i.e., vertebrates and invertebrates) including, but not limited to humans and other primates, rodents (e.g., mice, rats, and guinea pigs), lagamorphs (e.g., rabbits), bovines (e.g., cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term. However, the preferred species for use of this technology is *Homo sapiens*, and the next preferred use is in domestic pets, such as horses, dogs, and cats.

By "displayed" it is meant that a portion of the membrane protein is present on the surface of a cell, tissue and/or organ, and is thus in contact with the external environment of the cell, tissue or organ. A target epitope may be associated with a disease including but not limited to cancers and pathogenic infections.

X.A. Antigens and Epitopes Associated with Hyperproliferative Diseases

The mutant bispecific antibodies used in the present invention are specific to a variety of cell surface or intracellular antigens associated with hyperproliferative diseases. Normal tissue homeostasis is achieved by an intricate balance between the rate of cell proliferation and cell death. Disruption of this balance either by increasing the rate of cell proliferation or decreasing the rate of cell death can result in the abnormal growth of cells and is thought to be a major event in the development of cancer and other hyperproliferative diseases. A "hyperproliferative disease" is one in which cells have an abnormally high rate of cell division and/or an abnormally low rate of necrosis and/or apoptosis. Non-limiting examples include tumorigenesis; tumor progression; cancers, such as leukemia, solid tumors and metastases; psoriasis; benign hyperproliferative diseases, such as benign prostatic hypertrophy, benign hyperplasia of the skin, and hemangiomas; chronic inflammatory proliferative diseases, such as psoriasis and rheumatoid arthritis; proliferative ocular disorders, such as diabetic retinopathy and macular degeneration; and proliferative cardiovascular diseases, such as restenosis. Restenosis, characterized by the regrowth of smooth muscle cells into the lumen of blood vessels following angioplasty or other arterial damage, is a frequent and recurring problem in the long term success of angioplasty, and also occurs after arterial reconstructions, atherectomy, stent implantation, and laser angioplasty.

These antigens may be substances produced by, e.g., the tumor or may be substances which accumulate at a tumor site, on tumor cell surfaces or within tumor cells, whether in the cytoplasm, the nucleus or in various organelles or subcellular structures, including cell-surface or intracellular receptors. Among such tumor-associated markers are those disclosed, but not intended to be limiting, by Herberman, Immunodiagnosis of Cancer, in Fleisher ed., *The Clinical Biochemistry of Cancer*, page 347 (American Association of Clinical Chemists, 1979) and in U.S. Pat. Nos. 4,150,149; 4,361,544; and 4,444,744.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcino embryonic antigen (CEA), which stimulate the production of antibodies having a greatly reduced cross-reactivity to non-tumor substances as disclosed in U.S. Pat. Nos. 4,361,644 and 4,444,744.

Examples, which are non-limiting, of suitable tumor-associated markers or receptors, include the B-cell complex structures (e.g., CD19, CD20, CD21, CD22, CD23, CD80), other receptors expressed on hematopoietic and certain solid tumors (e.g., CD15, CD33, CD45, NCA90, NCA95, CD74, HLA-DR), and tumor-associated markers expressed on diverse cancers (e.g., carcinoembryonic antigen, Le(y), MUC-1, MUC-2, MUC-3, MUC-4, Tag-72 [B72.3 and CC49 constituting the antibodies against Tag-72], EGP-1, EGP-2, the antigen specific for A33 antibody, PSA, PSMA, EGFR, HER2/neu, PAM-4, AFP, HCG and its subunits, melanoma-associated antigens (e.g., S100), glioma-associated antigens, ovarian cancer-associated antigens, etc.), as well as target molecules expressed by the vasculature of the tumors (tumor angiogenesis markers, usually produced by the vascular endothelium), such as VEGF and tenascin (the latter in brain tumors, for example), and also to oncogene-associated markers, such as p53. Other tumor-associated antigens include, but are not limited to A3, BrE3, CD1, CD1a, CD3, CD5, CD15, CD25, CD30, CD33, CD45, CD79a, CSAp, EGP-1, EGP-2, Ep-CAM, Ba 733, KC4, KS-1, KS1-4, MAGE, RS5, IL-6, insulin growth factor-1 (IGF-1), Tn antigen, Thomson-Friedenreich antigens, tumor necrosis antigens, 17-1A, an angiogenesis marker, a cytokine, an immunomodulator, an oncogene marker (e.g., p53), and an oncogene product. In addition to the exemplary antibodies to such antigens disclosed herein, antibodies to these antigens are known in the art (see, for example, Kim et al., Expression and Characterization of a Recombinant Fab Fragment Derived from an Anti-Human alpha-Fetoprotein Monoclonal Antibody, *Mol. Cells* 11:158-163, 2001; and Haisma et al., Construction and characterization of a fusion protein of single-chain anti-CD40 antibody and human β-glucuronidase for antibody-directed enzyme prodrug therapy, *Blood* 92:184-190, 1998.

Another marker of interest is transmembrane activator and CAML-interactor (TACI). See Yu et al., *Nat. Immunol.* 1:252-256, 2000. Briefly, TACI is a marker for B-cell malignancies (e.g., lymphoma). Further it is known that TACI and B cell maturation antigen (BCMA) are bound by the tumor necrosis factor homolog a proliferation-inducing ligand (APRIL). APRIL stimulates in vivo proliferation of primary B and T cells and increases spleen weight due to accumulation of B cells in vivo. APRIL also competes with TALL-I (also called BLyS or BAFF) for receptor binding. Soluble BCMA and TACI specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

Tumor-specific antigens (TSAs), tumor-associated differentiation antigens (TADAs) and other antigens associated with cancers and other hyperproliferative diseases also include, but are not limited to, C1 IAC, a human cancer associated protein (U.S. Pat. No. 4,132,769); the CA125 antigen, an antigen associated with cystadenocarcinoma of the ovary, (Hanisch et al., *Carbohydr. Res.* 178:29-47, 1988; U.S. Pat. No. 4,921,790); CEA (carcinembryonic antigen), an antigen present on many adenocarcinomas; CORA (carcinoma or orosomucoid-related antigen) described by Toth et al. (U.S. Pat. No. 4,914,021); DF3 antigen from human breast carcinoma (U.S. Pat. Nos. 4,963,484 and 5,053,489); DU-PAN-2, a pancreatic carcinoma antigen (Lan et al., *Cancer Res.* 45:305-310, 1985); HCA, a human carcinoma antigen (U.S. Pat. No. 5,693,763); Her2, a breast cancer antigen (Fendly et al., The Extracellular Domain of HER2/neu Is a Potential Immunogen for Active Specific Immunotherapy of Breast Cancer, *J. Biol. Resp. Modifiers* 9:449-455, 1990); MSA, a breast carcinoma glycoprotein (Tjandra et al., *Br. J. Surg.* 75:811-817, 1988); MFGM, a breast carcinoma antigen (Ishida et al., *Tumor Biol.* 10:12-22, 1989); PSA, prostrate specific antigen (Nadji et al., Prostatic-specific-antigen, *Cancer* 48:1229-1232, 1981); STEAP (six transmembrane epithelial antigens of the prostate) proteins (U.S. Pat. No. 6,329,503); TAG-72, a breast carcinoma glycoprotein (Kjeldsen et al., *Cancer Res.* 48:2214-2220, 1988); YH206, a lung carcinoma antigen (Hinoda et al., *Cancer J.* 42:653-658, 1988); the p97 antigen of human melanoma (Estin et al., Recombinant Vaccinia Virus Vaccine Against the Human Melanoma Antigen p97 for Use in Immunotherapy, *Proc. Natl. Acad. Sci. USA* 85:1052-1056, 1988); and the melanoma specific antigen described in U.S. Pat. No. 6,025,191).

X.B. Antigens from Pathogens

X.B.1. Viruses

By way of non-limiting example, pathogens include viruses including, but not limited to, hepatitis type A, hepatitis type B, hepatitis type C, influenza, varicella, adenovirus, herpes simplex type I (HSV-I), herpes simplex type II (HSV-II), rinderpest, rhinovirous, echovirus, rabies virus, Ebola virus, rotavirus, respiratory syncytial virus, papilloma virus, papova virus, cytomegalovirus (CMV), echinovirus, arbovirus, huntavirus, coxsackie virus, mumps virus, measles virus, rubella virus, polio virus, human immunodeficiency virus type I (HIV-I) and human immunodeficiency virus type II (HIV-II), Sendai virus, feline leukemia virus, Reovirus, poliovirus, human serum parvo-like virus, simian virus 40 (SV40), respiratory syncytial virus (RSV), mouse mammary tumor virus (MMTV), Varicella-Zoster virus, Dengue virus, rubella virus, measles virus, adenovirus, human T-cell leukemia viruses, Epstein-Barr virus, murine leukemia virus, vesicular stomatitis virus (VSV), smallpox (Variola virus), Sindbis virus, lymphocytic choriomeningitis virus, Rinderpest virus, wart virus and blue tongue virus.

X.B.2. Intracellular Pathogens

By way of non-limiting example, pathogens include intracellular obligates, including but not limited to *Chlamydia* sp., *Rickettsia* sp., intracellular protozoa, including but not limited to, species of *Leishmania, Kokzidioa,* and *Trypanosoma,* including without limitation intracellular spirochetes, including but not limited to, *Borrelia burgdorfei,* the causative agent of Lyme disease; and species of *Plasmodia,* sporozoan obligate intracellular parasites of liver and red blood cells, including but not limited to *P. falciparum,* the causative agent of malaria, *Trypanosoma brucei,* a hemoflagellate causing sleeping sickness, and *Trypanosoma cruzi,* the cause of Chagas disease. For reviews of the immunology of such pathogens, see Blackman, Proteases involved in erythrocyte invasion by the malaria parasite: function and potential as chemotherapeutic targets, *Curr Drug Targets* 1:59-83, 2000; Kosma, Chlamydial lipopolysaccharide, *Biochim. Biophys. Acta.* 1455:387-402, 1999; Casadevall, Antibody-mediated protection against intracellular pathogens, *Trends Microbiol.* 6:102-7, 1998; Hoffman and Franke, Inducing protective immune responses against the sporozoite and liver stages of *Plasmodium, Immunol. Lett.* 41:89-94, 1994; Keusch, Immune responses in parasitic diseases. Part A: general concepts, *Rev. Infect. Dis.* 4:751-5, 1982; and Colli and Alves, Relevant glycoproteins on the surface of *Trypanosoma cruzi.*

X.B.3. Bacteria

Bacterial pathogens include, but are not limited to, *Streptococcus agalactiae, Legionella pneumophilia, Streptococcus pyogenes, Escherichia coli, Salmonella typhimurium, Neisseria gonorrhoeae, Neisseria meningitidis, Pneumococcus* sp., *Hemophilis influenzae* B, *Yersina pestis, Mycobacteria* sp. including by way of non-limiting example *Mycobacterium leprae* and *Mycobacterium tuberculosis, Treponema pallidum, Pseudomonas aeruginosa, Francisella tularensis, Brucella* sp. including *Brucella abortus, Bacillus anthracis* including Anthrax spores, *Clostridium botulinum* including Botulism toxin, and *Clostridium tetani* including Tetanus toxin). See U.S. Pat. No. 5,332,567.

X.B.4. Pathogenic Fungi

Fungal pathogens include, but are not limited to, *Candida* sp., *Aspergillus* sp., *Mucor* sp., *Rhizopus* sp., *Fusarium* sp., *Penicillium marneffei* and *Microsporum. Trichophyton mentagrophytes, Candida albicans, Histoplasma capsulatum, Blastomyces dermatitidis,* and *Coccidioides immitis* are fungal pathogens of particular interest.

XI. Antibodies

The Fvs of the invention constructs are derived from an antibody and specifically bind a targeted tissue. Exemplary Fvs are derived from anti-CD20 antibodies, such as those described in U.S. Provisional Application Ser. No. 60/356,132, entitled "Anti-CD20 Antibodies And Fusion Proteins Thereof And Methods Of Use", filed Feb. 14, 2002 (the contents of which are incorporated by reference herein in their entirety) and hMN-14 antibodies, such as those disclosed in U.S. Pat. No. 5,874,540 (the contents of which are incorporated by reference herein in their entirety), which is a Class III anti-carcinoembryonic antigen antibody (anti-CEA antibody).

The Fvs can be from murine antibodies, cdr-grafted (humanized) antibodies, or human antibodies. The Fvs can be derived from human monoclonal antibodies, transgenic mice with human Fv-libraries, or phage/ribosome human IgG libraries.

When the Fvs are derived from CDR-grafted antibodies, appropriate variable region framework sequences may be used having regard to the class or type of the donor antibody from which the antigen binding regions are derived. Preferably, the type of human framework used is of the same or similar class or type as the donor antibody. Advantageously, the framework is chosen to maximize or optimize homology with the donor antibody sequence, particularly at positions spatially close to or adjacent the CDRs. Examples of human frameworks which may be used to construct CDR-grafted antibodies are LAY, POM, TUR, TEI, KOL, NEWM, REI and EU. KOL and NEWM and are suitable for heavy chain construction. REI is suitable for light chain construction and EU is suitable for both heavy chain and light chain construction.

The light or heavy chain variable regions of the CDR-grafted antibodies may be fused to human light or heavy chain constant domains as appropriate, (the term "heavy chain constant domains" as used herein is to be understood to include hinge regions unless specified otherwise). The human constant domains of the CDR-grafted antibodies, where present, may be selected having regard to the proposed function of the antibody, in particular, the effector functions which may be required. For example, IgG1 and IgG3 isotype domains may be used when the CDR-grafted antibody is intended for therapeutic purposes and antibody effector functions are required. Alternatively, IgG2 and IgG4 isotype domains may be used when the CDR-grafted antibody is intended for purposes for which antibody effector functions are not required, e.g. for imaging, diagnostic or cytotoxic targeting purposes. Light chain human constant domains which may be fused to the light chain variable region include human Lambda or, especially, human Kappa chains.

Antibodies may further contain desirable mutations, e.g., mutations facilitating clearance of antibody constructs. A mutation may encompass, for example, a "conservative" change, wherein a substituted amino has similar structural or chemical properties, such as charge or size (e.g., replacement of leucine with isoleucine). A mutation also encompasses, for example, a "non-conservative" change (e.g., replacement of a glycine with a tryptophan).

The scFv component of the bi-specific mutant antibody specifically binds a targetable construct. The use of any scFv component is contemplated by the present invention. Preferred scFv components are 679 scFv (derived from a murine anti-HSG) and 734scFv (derived from a murine anti-diDTPA). The scFv can be murine, cdr-grafted (humanized) or human.

The light or heavy chain variable regions of the CDR-grafted antibodies may be fused to human light or heavy chain constant domains as appropriate, (the term "heavy chain constant domains" as used herein are to be understood to include hinge regions unless specified otherwise). The human constant domains of the CDR-grafted antibodies, where present, may be selected having regard to the proposed function of the antibody, in particular the effector functions which may be required. For example, IgG1 and IgG3 isotype domains may be used when the CDR-grafted antibody is intended for therapeutic purposes and antibody effector functions are required. Alternatively, IgG2 and IgG4 isotype domains may be used when the CDR-grafted antibody is intended for purposes for which antibody effector functions are not required, e.g. for imaging, diagnostic or cytotoxic targeting purposes. Light chain human constant domains which may be fused to the light chain variable region include human Lambda or, especially, human Kappa chains.

The murine monoclonal antibody designated 679 (an IgG1, K) binds with high affinity to molecules containing the tri-peptide moiety histamine succinyl glycyl (HSG) (Morel et al., Mol. Immunol. 27:995-1000, 1990). The nucleotide sequence pertaining to the variable domains ($V_H$ and $V_K$) of 679 has been determined (Qu et al, unpublished results). $V_K$ is one of two isotypes of the antibody light chains, $V_L$. The function of the two isotypes is identical. 679 can be humanized or fully human to help avoid an adverse response to the murine antibody.

hMN-14 is a humanized monoclonal antibody that binds specifically to CEA (Shevitz et al., J. Nucl. Med. 34, 217P, 1993; U.S. Pat. No. 6,254,868). While the original Mabs were murine, humanized antibody reagents are now utilized to reduce the human anti-mouse antibody response. A preferred mutant hMN-14 is hMN-14IgG$^{I253A}$, wherein amino acid residue 253 is changed from isoleucine to alanine.

734 is a murine monoclonal antibody designated that binds with high affinity to the metal-chelate complex indium-DTPA (diethylenetriamine-pentaacetic acid).

Single light chain and two heavy chain variable region sequences encoding the humanized anti-hCD20 (hA20) antibody were designed and constructed, as in U.S. Provisional Application Ser. No. 60/356,132, entitled "Anti-CD20 Antibodies And Fusion Proteins Thereof And Methods Of Use", filed Feb. 14, 2002, and U.S. application Ser. No. 10/366,709, filed Feb. 14, 2003 (the contents of each of which are incorporated by reference herein in their entirety). ha20 contains the $V_H$ and $V_K$ genes of A20, an anti-CD20 antibody, obtained by RT-PCR using the primer pairs VH1BACK/VH1FOR and VK1BACK/VK1FOR, respectively Orlandi et al., Proc. Natl. Acad. Sci. USA 86: 3833, 1989. Human REI framework sequences were used for $V_K$, and a combination of EU and NEWM framework sequences were used for $V_H$. There are a number of amino acid changes in each chain outside of the CDR regions when compared to the starting human antibody frameworks. The heavy chain of hA20, hA20$V_H$1, contains nine changes, while hA20$V_H$2 contains three changes from the human EU frameworks. hA20$V_H$2 is preferred because it contains more amino acids from the human antibody framework region than hA20$V_H$1. The light chain of hA20, hA20Vκ, contains seven amino acid changes from the REI framework.

The hLL-2 antibody is a humanized antibody prepared by combining the CDR regions of murine LL-2 antibody (mLL-2) with variable region framework sequences obtained from human antibodies. The sequence of the heavy and light chain variable regions of hLL-2 are shown in FIG. 1 of U.S. Pat. No. 5,789,554. As shown in that figure, the kappa light chain of hLL-2 contains the four light chain CDR regions from mLL-2 and the four framework regions of human antibody REI. The heavy chain of hLL-2 contains the three heavy chain CDRs from mLL-2 combined with three framework regions from human antibody EU, together with a fourth framework region from human antibody NEWM.

XI.A. Definitions

The term "antibody" is meant to encompass an immunoglobulin molecule obtained by in vitro or in vivo generation of an immunogenic response, and includes both polyclonal, antipeptide and monoclonal antibodies. The term "antibody"

also includes genetically engineered antibodies and/or antibodies produced by recombinant DNA techniques and "humanized" antibodies. As described below, humanized and even fully human antibodies can be produced by phage display, gene and chromosome transfection methods, as well as by other means.

An "immunogenic response" or "antigenic response" is one that results in the production of antibodies directed to a compound after the appropriate cells have been contacted therewith. The compound that is used to elicit an immunogenic response is referred to as an immunogen or antigen. The antibodies produced in the immunogenic response specifically bind the immunogen used to elicit the response.

The compound that is used to elicit an immunogenic response is referred to as an immunogen or antigen. An "epitope" or "antigenic determinant" is an area on the surface of an immunogen that stimulates a specific immune response directed to the epitope. In proteins, particularly denatured proteins, an epitope is typically defined and represented by a contiguous amino acid sequence. However, in the case of nondenatured proteins, epitopes also include structures, such as active sites, that are formed by the three-dimensional folding of a protein in a manner such that amino acids from separate portions of the amino acid sequence of the protein are brought into close physical contact with each other.

A "hapten" is a small molecule that cannot provoke an immune response unless first bound to an immunogenic carrier molecule. Although a hapten cannot itself provoke an immune response, it is specifically bound by antibodies generated during an immunogenic response to the hapten-carrier conjugate.

The term "antibody fragment" refers to functional fragments of antibodies, i.e., polypeptides that are smaller than an antibody which have sequences from the antibody, but nevertheless have the ability to specifically bind to an antigenic determinant. Antibody fragments can be prepared by in vitro manipulation of antibodies (e.g., by limited proteolysis of an antibody), or via recombinant DNA technology (e.g., the preparation of single-chain antibodies from phage display libraries).

XI.B. Antibody Structure

Naturally occurring (wildtype) antibody molecules are Y-shaped molecules consisting of four polypeptide chains, two identical heavy chains and two identical light chains, which are covalently linked together by disulfide bonds. Both types of polypeptide chains have constant regions, which do not vary or vary minimally among antibodies of the same class (i.e., IgA, IgM, etc.), and variable regions. The variable regions are unique to a particular antibody and comprise a recognition element for an epitope. The carboxy-terminal regions of both heavy and light chains are conserved in sequence and are called the constant regions (also known as C-domains). The amino-terminal regions (also known as V-domains) are variable in sequence and are responsible for antibody specificity. The antibody specifically recognizes and binds to an antigen mainly through six short complementarity-determining regions (CDRs) located in their V-domains.

Each light chain of an antibody is associated with one heavy chain, and the two chains are linked by a disulfide bridge formed between cysteine residues in the carboxy-terminal region of each chain, which is distal from the amino terminal region of each chain that constitutes its portion of the antigen binding domain. Antibody molecules are further stabilized by disulfide bridges between the two heavy chains in an area known as the hinge region, at locations nearer the carboxy terminus of the heavy chains than the locations where the disulfide bridges between the heavy and light chains are made. The hinge region also provides flexibility for the antigen-binding portions of an antibody.

An antibody's specificity is determined by the variable regions located in the amino terminal regions of the light and heavy chains. The variable regions of a light chain and associated heavy chain form an "antigen binding domain" that recognizes a specific epitope; an antibody thus has two antigen binding domains. The antigen binding domains in a wildtype antibody are directed to the same epitope of an immunogenic protein, and a single wildtype antibody is thus capable of binding two molecules of the immunogenic protein at the same time. Thus, a wildtype antibody is monospecific (i.e., directed to a unique antigen) and divalent (i.e., capable of binding two molecules of antigen).

XI.C. Types of Antibodies

"Polyclonal antibodies" are generated in an immunogenic response to a protein having many epitopes. A composition (e.g., serum) of polyclonal antibodies thus includes a variety of different antibodies directed to the same and to different epitopes within the protein. Methods for producing polyclonal antibodies are known in the art (see, e.g., Cooper et al., Section III of Chapter 11 in: *Short Protocols in Molecular Biology*, 2nd Ed., Ausubel et al., eds., John Wiley and Sons, New York, 1992, pages 11-37 to 11-41).

"Antipeptide antibodies" (also known as "monospecific antibodies") are generated in a humoral response to a short (typically, 5 to 20 amino acids) immunogenic polypeptide that corresponds to a few (preferably one) isolated epitopes of the protein from which it is derived. A plurality of antipeptide antibodies includes a variety of different antibodies directed to a specific portion of the protein, i.e, to an amino acid sequence that contains at least one, preferably only one, epitope. Methods for producing antipeptide antibodies are known in the art (see, e.g., Cooper et al., Section III of Chapter 11 in: *Short Protocols in Molecular Biology*, 2nd Ed., Ausubel et al., eds., John Wiley and Sons, New York, 1992, pages 11-42 to 11-46).

A "monoclonal antibody" is a specific antibody that recognizes a single specific epitope of an immunogenic protein. In a plurality of a monoclonal antibody, each antibody molecule is identical to the others in the plurality. In order to isolate a monoclonal antibody, a clonal cell line that expresses, displays and/or secretes a particular monoclonal antibody is first identified; this clonal cell line can be used in one method of producing the antibodies of the invention. Methods for the preparation of clonal cell lines and of monoclonal antibodies expressed thereby are known in the art (see, for example, Fuller et al., Section II of Chapter 11 in: *Short Protocols in Molecular Biology*, 2nd Ed., Ausubel et al., eds., John Wiley and Sons, New York, 1992, pages 11-22 to 11-11-36).

A "naked antibody" is an antibody that lacks the Fc portion of a wildtype antibody molecule. The Fc portion of the antibody molecule provides effector functions, such as complement fixation and ADCC (antibody dependent cell cytotoxicity), which set mechanisms into action that may result in cell lysis. See, e.g., Markrides, Therapeutic inhibition of the complement system, *Pharmacol. Rev.* 50:59-87, 1998. In some systems, it appears that the therapeutic action of an antibody depends upon the effector functions of the Fc region (see, e.g., Golay et al., Biologic response of B lymphoma cells to anti-CD20 monoclonal antibody rituximab in vitro: CD55 and CD59 regulate complement-mediated cell lysis, *Blood* 95:3900-3908, 2000).

However, it is possible that the Fc portion is not required for therapeutic function in every instance, as other mechanisms, such as apoptosis, can come into play. Moreover, the Fc region may be deleterious in some applications as antibodies comprising an Fc region are taken up by Fc receptor-bearing cells, thereby reducing the amount of therapeutic antibody taken up targeted cells. Vaswani and Hamilton, Humanized antibodies as potential therapeutic drugs. *Ann. Allergy Asthma Immunol.* 81:105-119, 1998. Components of the immune system may recognize and react to antibodies that are clumped together on the surface of tumor cells. It is thus envisioned that the resulting immune response will target and destroy, or at least limit the proliferation of, the tumor cells.

One way to get naked antibodies delivered to surfaces where they will clump together is to use a targetable construct or complex to bring different naked antibodies together on a targeted cellular surface. By way of non-limiting example, an anti-C20 antibody (e.g., Rituxan) and an anti-C22 antibody might be administered separately or together, allowed to clear so that unbound antibodies are removed from the system. The addition of a targetable construct that binds and connects both types antibodies, thereby forming a targetable construct in situ, which is expected to mimic a group of anti-C20 and anti-C22 antibodies clumped on the surface of a tumor cell.

Naked antibodies are also of interest for therapy of diseases caused by parasites, such as malaria. Vukovic et al., Immunoglobulin G3 antibodies specific for the 19-kilodalton carboxyl-terminal fragment of *Plasmodium yoelii* merozoite surface protein 1 transfer protection to mice deficient in Fc-γRI receptors, *Infect. Immun.* 68:3019-22, 2000.

Single chain antibodies (scFv) generally do not include portions of the Fc region of antibodies that are involved in effector functions and are thus naked antibodies, although methods are known for adding such regions to known scFv molecules if desired. See Helfrich et al., A rapid and versitile method for harnessing scFv antibody fragments with various biological functions, *J. Immunol. Meth.* 237:131-145, 2000; and de Haard et al., Creating and engineering human antibodies for immunotherapy, *Adv. Drug Delivery Rev.* 31:5-31, 1998.

XI.D. Antibody Fragments

XI.D.1. Proteolytic Antibody Fragments

Antibody fragments produced by limited proteolysis of wildtype antibodies are called proteolytic antibody fragments. These include, but are not limited to, the following.

"F(ab')$_2$ fragments" are released from an antibody by limited exposure of the antibody to a proteolytic enzyme, e.g., pepsin or ficin. An F(ab')$_2$ fragment comprises two "arms," each of which comprises a variable region that is directed to and specifically binds a common antigen. The two Fab' molecules are joined by interchain disulfide bonds in the hinge regions of the heavy chains; the Fab' molecules may be directed toward the same (bivalent) or different (bispecific) epitopes.

"Fab' fragments" contain a single anti-binding domain comprising an Fab and an additional portion of the heavy chain through the hinge region.

"Fab'-SH fragments" are typically produced from F(ab')$_2$ fragments, which are held together by disulfide bond(s) between the H chains in an F(ab')$_2$ fragment. Treatment with a mild reducing agent such as, by way of non-limiting example, beta-mercaptoethylamine, breaks the disulfide bond(s), and two Fab' fragments are released from one F(ab')$_2$ fragment. Fab'-SH fragments are monovalent and monospecific.

"Fab fragments" (i.e., an antibody fragment that contains the antigen-binding domain and comprises a light chain and part of a heavy chain bridged by a disulfide bond) are produced by papain digestion of intact antibodies. A convenient method is to use papain immobilized on a resin so that the enzyme can be easily removed and the digestion terminated. Fab fragments do not have the disulfide bond(s) between the H chains present in an F(ab')$_2$ fragment.

XI.D.2. Recombinant Antibody Fragments

"Single-chain antibodies" are one type of antibody fragment. The term single chain antibody is often abbreviated as "scFv" or "sFv." These antibody fragments are produced using molecular genetics and recombinant DNA technology. A single-chain antibody consists of a polypeptide chain that comprises both a $V_H$ and a $V_L$ portion. Unlike wildtype antibodies, wherein two separate heavy and light polypeptide chains are conjoined to form a single antigen-binding variable region, a single-chain antibody is a single polypeptide that comprises an antigen-binding variable region. That is, a single-chain antibody comprises the variable, antigen-binding determinative region of a single light and heavy chain of an antibody linked together by a chain of 10-25 amino acids.

The term "single-chain antibody" includes but is not limited to a disulfide-linked Fv (dsFv) in which two single-chain antibodies linked together by a disulfide bond; a bispecific sFv (a sFv or a dsFv molecule having two antigen-binding domains, each of which may be directed to a different epitope); a diabody (a dimerized sFv formed when the $V_H$ domain of a first sFv assembles with the $V_L$ domain of a second sFv and the $Y_L$ domain of the first sFv assembles with the $V_H$ domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes).

"Camelid antibodies" are unlike mammalian antibodies in that they need only V-domain, namely $V_H$, to specifically and effectively bind an antigen. Camelid antibodies or fragments thereof have the advantages of being water soluble and showing good expression in yeast and *Aspergillus* moulds. For reviews, see Muyldermans, Single domain camel antibodies: current status, *J. Biotechnol.* 74:277-302, 2001; and Wernery, Camelid immunoglobulins and their importance for the newborn—a review, *J. Vet. Med. B. Infect. Dis. Vet. Public Health* 48:561-8, 2001. See also Spinelli et al., Camelid heavy-chain variable domains provide efficient combining sites to haptens, *Biochemistry* 39:1217-22, 2000; Muyldermans et al., Unique single-domain antigen binding fragments derived from naturally occurring camel heavy-chain antibodies, *J. Mol. Recog.* 12:131-40, 1999; and Davies et al., Single antibody domains as small recognition units: design and in vitro antigen selection of camelized, human $V_H$ domains with improved protein stability, *Protein Eng.* 9:531-7, 1996. Other immunoglobulin-like molecules from other species may also be used. See, e.g., Roux et al., Structural analysis of the nurse shark (new) antigen receptor (NAR): molecular convergence of NAR and unusual mammalian immunoglobulins, *Proc. Natl. Acad. Sci. USA.* 95:11804-9, 1998. Methods of producing camelid antibodies are known in the art. See, for example, U.S. Pat. Nos. 6,015,695; 6,005,079; 5,874,541; 5,840,526; 5,800,988; and 5,759,808, each of which is entitled Immunoglobulins Devoid of Light Chains.

"Humanized antibodies" have been modified, by genetic manipulation and/or in vitro treatment to be more human, in terms of amino acid sequence, glycosylation pattern, etc., in order to reduce the antigenicity of the antibody or antibody fragment in an animal to which the antibody is intended to be administered. See Gussow and Seemann, Humanization of monoclonal antibodies, *Meth. Enz.* 203:99-121, 1991 and Vaswani and Hamilton, Humanized antibodies as potential therapeutic drugs, *Ann. Allergy Asthma Immunol.* 81:105-119, 1998.

"Fully human antibodies" are human antibodies produced in transgenic animals such as XENOMOUSE®. XENOMOUSE® strains are genetically engineered mice in which the murine IgH and Igk loci have been functionally replaced by their Ig counterparts on yeast artificial YAC transgene. These human Ig transgenes can carry the majority of the human variable repertoire and can undergo class switching from IgM to IgG isotypes. The immune system of the XENOMOUSE® recognizes administered human antigens as foreign and produces a strong humoral response. The use of XENOMOUSE® in conjunction with well-established hybridomas techniques, results in fully human IgG mAbs with sub-nanomolar affinities for human antigens (see U.S. Pat. Nos. 5,770,429, entitled "Transgenic non-human animals capable of producing heterologous antibodies", U.S. Pat. No. 6,162,963, entitled "Generation of xenogenetic antibodies"; U.S. Pat. No. 6,150,584, entitled "Human antibodies derived from immunized XENOMOUSE®", U.S. Pat. No. 6,114,598, entitled "Generation of xenogeneic antibodies"; and U.S. Pat. No. 6,075,181, entitled "Human antibodies derived from immunized XENOMOUSE®"; for reviews, see Green, Antibody engineering via genetic engineering of the mouse: XENOMOUSE® strains are a vehicle for the facile generation of therapeutic human monoclonal antibodies, J. Immunol. Meth. 231:11-23, 1999; Wells, Eek, a XENOMOUSE®: Abgenix, Inc., Chem. Biol. 7:R185-6, 2000; and Davis et al., Transgenic mice as a source of fully human antibodies for the treatment of cancer, Cancer Metastasis Rev. 18:421-5, 1999).

"Complementary determining region peptides" or "CDR peptides" are another form of an antibody fragment. A CDR peptide (also known as "minimal recognition unit") is a peptide corresponding to a single complementarity-determining region (CDR), and can be prepared by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2:106, 1991.

"T-cell receptor (TCR) fragments" are soluble peptides having amino acid sequences corresponding to the variable and constant regions of a T-cell receptor. Soluble TCR fragments can be prepared as a single chain (scTCR) or as separate components with dimerization domain that allow the separate peptides to stably associated with each other. (Willcox et al., Production of soluble alpha:beta T-cell receptor heterodimers suitable for biophysical analysis of ligand binding, *Protein Science* 8:2418-2423, 1999). Soluble TCR molecules made using chinese hamster ovary (CHO) cells are described by Lin et al., Expression of T Cell Antigen Receptor Heterodimers in a Lipid-Linked Form, *Science* 249:677-679, 1990; and Davis et al., TCR Recognition and Selection In Vivo, Cold Spring Harbor Symposia on Quantitative Biology, LIV, 119-128, 1989). Both of these articles describe the use of a GPI linkage approach to produce soluble TCR molecules. For other examplary methods of producing soluble TCR fragments, see, for example, U.S. Pat. Nos. 6,165,745, Recombinant production of immunoglobulin-like domains in prokaryotic cells; U.S. Pat. No. 6,080,840, Soluble T cell receptors; U.S. Pat. No. 5,723,309, Production of subunits of soluble T cell receptors by co-transfection; U.S. Pat. No. 5,552,300, T cell antigen receptor V region proteins and methods of preparation thereof; Novotny et al., *Proc. Natl. Acad Sci USA.* 88:8646-8650, 1991; Ward, *Scand. J. Immunol.* 34:215-220, 1991; and Pecorari et al., Folding, Heterodimeric Association and Specific Peptide Recognition of a Murine $\alpha\beta$ T-cell Receptor Expressed in *Escherichia coli, J. Mol. Biol.* 285:1831-1843, 1999.

"Chimeric antibody derivatives" such as chimeric TCR:Ab molecules have been produced by shuffling the variable and constant domains of murine T-cell receptors with the constant region of an immunoglobulin kappa light chain. For example, Gregoire et al. (*Proc. Natl. Acad. Sci. USA* 88:8077-8081, 1991) show a murine chimera consisting of the C-alpha and V-alpha genes of the KB5-C2 joined to the C region of the kappa light chain of the S105 monoclonal antibody, and a V-beta-C-beta-C-kappa. chimera. Both are transfected into a mammalian B cell myeloma that does not express native immunoglobulin heavy or light chains. See also, Weber et al., *Nature* 356:793-795, 1992.

In "cysteine-modified antibodies," a cysteine amino acid is inserted or substituted on the surface of antibody by genetic manipulation and used to conjugate the antibody to another molecule via, e.g., a disulfide bridge. Cysteine substitutions or insertions for antibodies have been described (see U.S. Pat. No. 5,219,996). Methods for introducing Cys residues into the constant region of the IgG antibodies for use in site-specific conjugation of antibodies are described by Stimmel et al. (*J. Biol. Chem* 275:330445-30450, 2000).

XII. Pharmaceutical Compositions

XII.A. Definitions

A "pharmaceutical composition" refers to a composition comprising a drug wherein the carrier is a pharmaceutically acceptable carrier, while a "veterinary composition" is one wherein the carrier is a veterinarily acceptable carrier. The term "pharmaceutically acceptable carrier" or "veterinarily acceptable carrier" includes any medium or material that is not biologically or otherwise undesirable, i.e, the carrier may be administered to an organism along with a composition or compound of the invention without causing any undesirable biological effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated in its entirety by reference herein into the present application, as is *Pharmaceutical Dosage Forms & Drug Delivery Systems*, 7th Edition, Ansel et al., editors, Lippincott Williams & Wilkins, 1999.

The drug (i.e., targetable construct or complex) is included in the pharmaceutical composition in an amount sufficient to produce the desired effect upon the patient. The pharmaceutical compositions of the invention can further comprise other chemical components, such as diluents and excipients. A "diluent" is a chemical compound diluted in a solvent, preferably an aqueous solvent, that facilitates dissolution of the drug in the solvent, and it may also serve to stabilize the biologically active form of the drug or one or more of its components. Salts dissolved in buffered solutions are utilized as diluents in the art. For example, preferred diluents are buffered solutions containing one or more different salts. A preferred buffered solution is phosphate buffered saline (particularly in conjunction with compositions intended for pharmaceutical administration), as it mimics the salt conditions of human blood. Since buffer salts can control the pH of a solution at low concentrations, a buffered diluent rarely modifies the biological activity of a biologically active peptide.

An "excipient" is any more or less inert substance that can be added to a composition in order to confer a suitable property, for example, a suitable consistency or to form a drug.

Suitable excipients and carriers include, in particular, fillers such as sugars, including lactose, sucrose, mannitol, or sorbitol cellulose preparations such as, for example, maize starch, wheat starch, rice starch, agar, pectin, xanthan gum, guar gum, locust bean gum, hyaluronic acid, casein potato starch, gelatin, gum tragacanth, polyacrylate, methyl cellulose, hydroxypropylmethyl-cellulose, sodium carboxymethylcellulose, and/or polyvinylpyrrolidone (PVP). If desired, disintegrating agents can also be included, such as cross-linked polyvinylpyrrolidone, agar, or alginic acid or a salt thereof such as sodium alginate. Other suitable excipients and carriers include hydrogels, gellable hydrocolloids, and chitosan. Chitosan microspheres and microcapsules can be used as carriers. See WO 98/52547 (which describes microsphere formulations for targeting compounds to the stomach, the formulations comprising an inner core (optionally including a gelled hydrocolloid) containing one or more active ingredients, a membrane comprised of a water insoluble polymer (e.g., ethylcellulose) to control the release rate of the active ingredient(s), and an outer layer comprised of a bioadhesive cationic polymer, for example, a cationic polysaccharide, a cationic protein, and/or a synthetic cationic polymer; U.S. Pat. No. 4,895,724. Typically, chitosan is cross-linked using a suitable agent, for example, glutaraldehyde, glyoxal, epichlorohydrin, and succinaldehyde. Compositions employing chitosan as a carrier can be formulated into a variety of dosage forms, including pills, tablets, microparticles, and microspheres, including those providing for controlled release of the active ingredient(s). Other suitable bioadhesive cationic polymers include acidic gelatin, polygalactosamine, polyamino acids such as polylysine, polyhistidine, polyornithine, polyquaternary compounds, prolamine, polyimine, diethylaminoethyldextran (DEAE), DEAE-imine, DEAE-methacrylate, DEAE-acrylamide, DEAE-dextran, DEAF-cellulose, poly-p-aminostyrene, polyoxethane, copolymethacrylates, polyamidoamines, cationic starches, polythiodiethylaminomethylethylene and polyvinylpyridine.

XII.B. Formulation of Pharmaceutical Compositions

The targetable constructs and complexes of the invention can be formulated in any suitable manner. The targetable constructs and complexes may be uniformly (homogeneously) or non-uniformly (heterogenously) dispersed in the carrier. Suitable formulations include dry and liquid formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a pharmaceutical composition according to the invention is compressed into tablet or pill form suitable for oral administration or compounded into a sustained release formulation. When the pharmaceutical composition is intended for oral administration but the targetable construct or complex is to be delivered to epithelium in the intestines, it is preferred that the formulation be encapsulated with an enteric coating to protect the formulation and prevent premature release of the targetable constructs and complexes included therein. As those in the art will appreciate, the pharmaceutical compositions of the invention can be placed into any suitable dosage form. Pills and tablets represent some of such dosage forms. The pharmaceutical compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

Some preferred embodiments concern compositions that comprise a bioadhesive, preferably a mucoadhesive, coating. A "bioadhesive coating" is a coating that allows a drug to adhere to a biological surface or substance better than occurs absent the coating. A "mucoadhesive coating" is a preferred bioadhesive coating that allows a substance, for example, a composition according to the invention, to adhere better to mucosa occurs absent the coating. For example, micronized particles (e.g., particles having a mean diameter of about 5, 10, 25, 50, or 100 µm) can be coated with a mucoadhesive. The coated particles can then be assembled into a dosage form suitable for delivery to an organism. Preferably, and depending upon the location where the cell surface transport moiety to be targeted is expressed, the dosage form is then coated with another coating to protect the formulation until it reaches the desired location, where the mucoadhesive enables the formulation to be retained while the compositions or compounds of the invention interact with the target cell surface transport moiety.

XII.C. Administration of Pharmaceutical Compositions

The pharmaceutical compositions of the invention facilitate administration of monoclonal antibodies to an organism, preferably an animal, preferably a mammal, bird, fish, insect, or arachnid. Preferred mammals include bovine, canine, equine, feline, ovine, and porcine animals, and non-human primates. Humans are particularly preferred. Multiple techniques of administering or delivering a compound exist in the art including, but not limited to, oral, rectal (e.g., an enema or suppository) aerosol (e.g., for nasal or pulmonary delivery), parenteral, and topical administration. Preferably, sufficient quantities of the composition or compound of the invention are delivered to achieve the intended effect. The particular amount of composition or compound to be delivered will depend on many factors, including the effect to be achieved, the type of organism to which the composition is delivered, delivery route, dosage regimen, and the age, health, and sex of the organism. As such, the particular dosage of a composition or compound of the invention included in a given formulation is left to the ordinarily skilled artisan's discretion.

Those skilled in the art will appreciate that when the pharmaceutical compositions of the present invention are administered as agents to achieve a particular desired biological result, which may include a therapeutic or protective effect(s) (including vaccination), it may be necessary to combine the composition or compound of the invention with a suitable pharmaceutical carrier. The choice of pharmaceutical carrier and the preparation of the composition or compound as a therapeutic or protective agent will depend on the intended use and mode of administration. Suitable formulations and methods of administration of therapeutic agents include, but are not limited to, those for oral, pulmonary, nasal, buccal, ocular, dermal, rectal, or vaginal delivery.

Depending on the mode of delivery employed, the context-dependent functional entity can be delivered in a variety of pharmaceutically acceptable forms. For example, the context-dependent functional entity can be delivered in the form of a solid, solution, emulsion, dispersion, micelle, liposome, and the like, incorporated into a pill, capsule, tablet, suppository, areosol, droplet, or spray. Pills, tablets, suppositories, areosols, powders, droplets, and sprays may have complex, multilayer structures and have a large range of sizes. Aerosols, powders, droplets, and sprays may range from small (1 micron) to large (200 micron) in size.

Pharmaceutical compositions of the present invention can be used in the form of a solid, a lyophilized powder, a solution, an emulsion, a dispersion, a micelle, a liposome, and the like, wherein the resulting composition contains one or more of the targetable constructs or complexes of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Examples of a stabilizing dry agent includes triulose, preferably at concentrations of 0.1% or greater (See, e.g., U.S. Pat. No. 5,314,695).

XII.D. Dosages

Although individual needs may vary, determination of optimal ranges for effective amounts of pharmaceutical compositions is within the skill of the art. Human doses can be extrapolated from animal studies (Katocs et al., Chapter 27 In: *Remington's Pharmaceutical Sciences*, 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s). See, for example, Nies et al., Chapter 3 In: *Goodman & Gilman's The Pharmacological Basis of Therapeutics*, 9th Ed., Hardman et al., eds., McGraw-Hill, New York, N.Y., 1996)

Dosing of therapeutic compositions is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The term "patient" is intended to encompass animals (e.g., cats, dogs and horses) as well as humans. Persons of ordinary skill can easily determine optimum dosages, dosing methodologies and repetition rates. Optimum dosages may vary depending on the relative potency of individual therapeutic agents, and can generally be estimated based on $EC_{50}$ found to be effective in vitro and in vivo animal models.

The range of doses (the amount of targetable construct or complex administered) is broad, since in general the efficacy of a therapeutic effect for different mammals varies widely with doses typically being 20, 30 or even 40 times smaller (per unit body weight) in man than in the rat. In general, dosage is from 0.01 μg to 100 g per kg of body weight, preferably 0.01 μg to 10 g/kg of body weight, 0.01 μg to 1000 mg/kg of body weight, 0.01 μg to 100 mg/kg of body weight, 0.01 μg to 10 mg/kg of body weight, 0.01 μg to 1 mg/kg of body weight, 0.01 μg to 100 μg/kg of body weight, 0.01 μg to 10 μg/kg of body weight, 0.01 μg to 1 μg/kg of body weight, 0.01 μg to 10 μg/kg of body weight, 0.01 μg to 1 μg/kg of body weight, 0.01 μg to 0.1 μg/kg of body weight, and ranges based on the boundaries of the preceding ranges of concentrations. Thus, for example, the preceding description of dosages encompasses dosages within the range of 100 to 10 g per kg of body weight, 10 g to 1000 mg/kg of body weight, 1000 mg to 100 mg, etc.

Doses may be given once or more daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Following successful treatment, it may be desirable to have the patient undergo maintenance therapy to prevent the recurrence of the disease state, wherein the therapeutic agent is administered in maintenance doses, ranging from 0.01 ug to 100 g per kg of body weight, once or more daily, to once every 20 years.

The specific dose is calculated according to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data.

An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308:43-53, 2001; Steimer et al., *Clinica Chimica Acta* 308:33-41, 2001).

XIII. References, Patents and Published Patent Applications

XIII.A. Scientific References

Bamias, A., and Epenetos, A. A. Two-step strategies for the diagnosis and treatment of cancer with bioconjugates. *Antibody, Immunoconjugates, Radiophamm.* 1992; 5: 385-395.

Barbet, J., Peltier, P., Bardet, S., Vuillez, J P., Bachelot, I., Denet, S., Olivier, P., Lecia, F., Corcuff, B., Huglo, D., Proye, C., Rouvier, E., Meyer, P., Chatal, J. F. Radioimmunodetection of medullary thyroid carcinoma using indium-111 bivalent hapten and anti-CEA x anti-DTPA-indium bispecifc antibody. *J. Nucl. Med.* 1998; 39:1172-1178.

Bos, E S., Kuijpers, W H A., Meesters-Winters, M., Pham, D T., deHaan, A S., van Doormalen, Am., Kasperson, F. M., vanBoeckel, C A A and Gouegeon-Bertrand, F. In vivo evaluation of DNA-DNA hybridization as a two-step approach in radioimmunotherapy of cancer. *Cancer Res.* 1994; 54:3479-3486.

Gautherot, E., Bouhou, J., LeDoussal, J.-M., Manetti, C., Martin, M., Rouvier, E., Barbet, J. Therapy for colon carcinoma xenografts with bi-specific antibody-targeted, iodine-131-labeled bivalent hapten. *Cancer suppl.* 1997; 80: 2618-2623.

Gautherot, E., Bouhou, J., Loucif, E., Manetti, C., Martin, M., LeDoussal, J. M., Rouvier, E., Barbet, J. Radioimmunotherapy of LS174T colon carcinoma in nude mice using an iodine-131-labeled bivalent hapten combined with an anti-CEA x anti-indium-DTPA bi-specific antibody. *J. Nucl. Med. Suppl.* 1997; 38: 7p.

Goodwin, D. A., Meares, C F., McCall, M J., McTigue, M., Chaovapong, W. Pre-targeted immunoscintigraphy of murine tumors with indium-111-labeled bifunctional haptens. *J. Nucl. Med.* 1988; 29:226-234.

Greenwood, F. C. and Hunter, W. M. The preparation of I-131 labeled human growth hormone of high specific radioactivity. Biochem. 1963; 89:114-123.

Hawkins, G. A., McCabe, R. P., Kim, C.-H., Subramanian, R., Bredehorst, R., McCullers, G. A., Vogel, C.-W., Hanna, M. G. Jr., and Pomata, N. Delivery of radionuclides to pretargeted monoclonal antibodies using dihydrofolate reductase and methotrexate in an affinity system. *Cancer Res.* 1993; 53: 2368-2373.

Kranenborg, M. h., Boerman, O. C., Oosterwijk-Wakka, j., weijert, M., Corstens, F., Oosterwijk, E. Development and characterization of anti-renal cell carcinoma x antichelate bi-specific monoclonal antibodies for two-phase targeting of renal cell carcinoma. *Cancer Res.* (suppl) 1995; 55: 5864s-5867s.

Penefsky, H. S. A centrifuged column procedure for the measurement of ligand binding by beef heart F1. Part G. Methods Enzymol. 1979; 56:527-530.

Schuhmacher, J., Klivenyi, G., Matys, R., Stadler, M., Regiert, T., Hauser, H., Doll, J., Maier-Borst, W., Zoller, M. Multistep tumor targeting in nude mice using bi-specific antibodies and a gallium chelate suitable for immunocintigraphy with positron emission tomography. *Cancer Res.* 1995; 55, 115-123.

Sharkey, R M., Karacay, H. Griffiths, G L., Behr, T M., Blumenthal, R D., Mattes, M J., Hansen, H J., Goldenberg, D M. Development of a streptavidin-anti-carcinoembryonic antigen antibody, radiolabeled biotin pretargeting method for radioimmunotherapy of colorectal cancer. Studies in a human colon cancer xenograft model. *Bioconjugate Chem* 1997; 8:595-604.

Stickney, D R., Anderson, L D., Slater, J B., Ahlem, C N., Kirk, G A., Schweighardt, S A and Frincke, J M. Bifunctional antibody: a binary radiopharmaceutical delivery system for imaging colorectal carcinoma. Cancer Res. 1991; 51: 6650-6655.

XIII.B. U.S. Patents

U.S. Pat. No. 6,358,489, Fluorination of proteins and peptides for F-18 positron emission tomography U.S. Pat. No. 6,331,175, Method and kit for imaging and treating organs and tissues.

U.S. Pat. No. 6,319,500, Detection and treatment of infections with immunoconjugates.

U.S. Pat. No. 6,306,393, Immunotherapy of B-cell malignancies using anti-CD22 antibodies.

U.S. Pat. No. 6,254,868, Glycosylated humanized B-cell specific antibodies.

U.S. Pat. No. 6,228,362, Boron neutron capture therapy using pre-targeting methods.

U.S. Pat. No. 6,187,287, Immunoconjugates and humanized antibodies specific for B-cell lymphoma and leukemia cells.

U.S. Pat. No. 6,187,284, Fluorination of proteins and peptides for F-18 positron emission tomography.

U.S. Pat. No. 6,183,744, Immunotherapy of B-cell malignancies using anti-CD22 antibodies.

U.S. Pat. No. 6,132,718, Multi-stage cascade boosting vaccine.

U.S. Pat. No. 6,126,916, Radiometal-binding peptide analogues.

U.S. Pat. No. 6,120,768, Dota-biotin derivatives.

U.S. Pat. No. 6,096,289, Intraoperative, intravascular, and endoscopic tumor and lesion detection, biopsy and therapy.

U.S. Pat. No. 6,090,381 Stimulation of an immune response with antibodies labeled with the α-galactosyl epitope.

U.S. Pat. No. 6,083,477 Non-antigenic toxin-conjugate and fusion protein of internalizing receptor system.

U.S. Pat. No. 6,077,499 Targeted combination immunotherapy of cancer

U.S. Pat. No. 6,071,490 Position emission tomography using gallium-68 chelates

U.S. Pat. No. 6,010,680 Thiolation of proteins for radionuclide-based radioimmunodetection and radioimmunotherapy U.S. Pat. No. 5,976,492 Radioactive phosphorus labeled proteins for targeted radiotherapy U.S. Pat. No. 5,965,131 Delivery of diagnostic and therapeutic agents to a target site U.S. Pat. No. 5,958,408 Delivery of diagnostic and therapeutic agents to a target site U.S. Pat. No. 5,922,302 Detection and therapy of lesions with biotin/avidin-metal chelating protein conjugates U.S. Pat. No. 5,874,540 CDR-grafted type III anti-CEA humanized mouse monoclonal antibodies U.S. Pat. No. 5,851,527 Method for antibody targeting of therapeutic agents U.S. Pat. No. 5,846,741 Boron neutron capture therapy using pre-targeting methods U.S. Pat. No. 5,843,397 Cytotoxic therapy for graft rejection U.S. Pat. No. 5,798,100 Multi-stage cascade boosting vaccine U.S. Pat. No. 5,789,554 Immunoconjugates and humanized antibodies specific for B-cell lymphoma and leukemia cells U.S. Pat. No. 5,776,095 Method and kit for imaging and treating organs and tissues U.S. Pat. No. 5,776,094 Method and kit for imaging and treating organs and tissues U.S. Pat. No. 5,776,093 Method for imaging and treating organs and tissues U.S. Pat. No. 5,772,981 Thiolation of proteins for radionuclide-based radioimmunodetection and radioimmunotherapy U.S. Pat. No. 5,753,206 Radiometal-binding analogues of luteinizing hormone releasing hormone U.S. Pat. No. 5,746,996 Thiolation of peptides for radionuclide-based radiodetection and radiotherapy U.S. Pat. No. 5,736,119 Detection and therapy of lesions with biotin/avidin-metal chelating protein conjugates U.S. Pat. No. 5,728,369 Radioactive phosphorus labeling of proteins for targeted radiotherapy U.S. Pat. No. 5,716,595 Intraoperative, intravascular and endoscopic tumor and lesion detection and therapy with monovalent antibody fragments U.S. Pat. No. 5,705,158 Treatment of infectious and inflammatory lesions U.S. Pat. No. 5,698,405 Method of reducing immunogenicity U.S. Pat. No. 5,698,178 Polyspecific immunoconjugates and antibody composites for targeting the multidrug resistant phenotype U.S. Pat. No. 5,697,902 Method for imaging and treating organs and tissues U.S. Pat. No. 5,686,578 Polyspecific immunoconjugates and antibody composites for targeting the multidrug resistant phenotype U.S. Pat. No. 5,677,427 Chimeric antibody for detection and therapy of infectious and inflammatory lesions U.S. Pat. No. 5,670,132 Modified radioantibody fragments for reduced renal uptake U.S. Pat. No. 5,637,288 Chimeric antibody for detection and therapy of infectious and inflammatory lesions U.S. Pat. No. 5,635,603 Preparation and use of immunoconjugates U.S. Pat. No. 5,632,968 Detection of cardiovascular lesions U.S. Pat. No. 5,612,016 Conjugates of antibodies and bifunctional ligands U.S. Pat. No. 5,609,846 Radiolabelled antibody cytotoxic therapy of infectious or autoimmune disease U.S. Pat. No. 5,601,825 Therapeutic conjugates of toxins and drugs U.S. Pat. No. 5,541,297 Therapeutic conjugates of toxins and drugs U.S. Pat. No. 5,525,338 Detection and therapy of lesions with biotin/avidin conjugates.

U.S. Pat. No. 5,514,363 Method for radiolabeling antibody fragments.

U.S. Pat. No. 5,482,698 Detection and therapy of lesions with biotin/avidin polymer conjugates.

U.S. Pat. No. 5,443,953 Preparation and use of immunoconjugates.

U.S. Pat. No. 5,439,665 Detection and treatment of infectious and inflammatory lesions.

U.S. Pat. No. 5,364,612 Detection of cardiovascular lesions.

U.S. Pat. No. 5,334,708 Method for radiolabeling monovalent antibody fragments.

U.S. Pat. No. 5,332,567 Detection and treatment of infections with immunoconjugates.

U.S. Pat. No. 5,328,679 Methods for technetium/rhenium labeling of proteins.

U.S. Pat. No. 5,128,119 Methods for technetium/rhenium labeling of f(ab')$_2$ fragments.

U.S. Pat. No. 5,120,525 Radiolabeled antibody cytotoxic therapy of cancer.

U.S. Pat. No. 5,101,827 Lymphographic and organ imaging method and kit.

U.S. Pat. No. 5,061,641 Method for radiolabeling proteins.

U.S. Pat. No. 4,932,412 Intraoperative and endoscopic tumor detection and therapy.

U.S. Pat. No. 4,925,648 Detection and treatment of infectious and inflammatory lesions.

U.S. Pat. No. 4,900,684 CEA immunoassay free of human anti-mouse antibody false positives.

U.S. Pat. No. 4,824,659 Antibody conjugates.

U.S. Pat. No. 4,792,521 Non-enzymatic immunohistochemical staining system and reagents.

U.S. Pat. No. 4,737,453 Sandwich immunoassay utilizing a separation specific binding substance.

U.S. Pat. No. 4,735,210 Lymphographic and organ imaging method and kit.

U.S. Pat. No. 4,699,880 Method of producing monoclonal anti-idiotype antibody.

U.S. Pat. No. 4,680,338 Bifunctional linker.

U.S. Pat. No. 4,624,846 Method for enhancing target specificity of antibody localization and clearance of non-target diagnostic and therapeutic principles.

U.S. Pat. No. 4,595,654 Method for detecting immune complexes in serum.

XIII.C. Published PCT Patent Applications

WO 02/12347, Immunotherapy for Chronic Myelocytic Leukemia

WO 02/08293, Multivalent Target Binding Protein

WO 02/02150, Stable Radioiodine Conjugates And Methods For Their Synthesis.

WO 01/97855, Targeted Combination Immunotherapy Of Cancer And Infectious Diseases.

WO 00/74718, Immunotherapy Of Autoimmune Disorders Using Antibodies Which Target B-Cells.

WO 00/67795, Immunotherapy Of B-Cell Malignancies Using Anti-Cd22 Antibodies.

WO 00/33874, Boron Neutron Capture Therapy Using Pre-Targeting Methods.

WO 00/21573, Site-Specific Labeling Of Disulfide-Containing Targeting Vectors.

WO 00/16808, Methods And Compositions For Increasing The Target-Specific Toxicity Of A Chemotherapy Drug.

WO 00/14537, Diagnosis Of Multidrug Resistance In Cancer And Infectious Lesions.

WO 99/66951, Use Of Bi-Specific Antibodies For Pre-Targeting Diagnosis And Therapy.

WO 99/59633, Therapeutics Using A Bispecific Anti-HLA Class Ii Invariant Chain X Anti-Pathogen Antibody.

WO 99/56792, Positron Emission Tomography Using Gallium-68 Chelates.

WO 99/46389, Recombinant Onconase, And Chemical Conjugates And Fusion Proteins Of Recombinant Onconase.

WO 99/30745, Dota-Biotin Derivatives.

WO 99/24472, Glycosylated Antibodies And Antibody Fragments Having Reactive Ketone Groups.

WO 99/11590, Fluorination Of Proteins And Peptides For F-18 Positron Emission Tomography.

WO 99/11294, Stable Radioiodine Conjugates And Methods For Their Synthesis. WO 98/50435, Immunotoxins, Comprising An One Protein, Directed Against Malignant Cells.

WO 98/42378, Immunotherapy Of B-Cell Malignancies Using Anti-CD22 Antibodies.

WO 98/34957, Stimulation Of An Immune Response With Antibodies Labeled With The ±-Galactosyl Epitope.

WO 98/16254, Non-Antigenic Toxin-Conjugate And Fusion Protein Of Internalizing Receptor System.

WO 98/08548, Stable Radioiodine Conjugates And Methods For Their Synthesis

WO 98/04917, Boron Neutron Capture Therapy Using Pre-Targeting Methods Immunomedics Inc.

WO 98/04293, Improved Detection And Therapy Of Lesions With Biotin-Chelate Conjugates.

WO 98/02192, Radiometal-Binding Peptide Analogues.

WO 97/41898, Targeted Combination Immunotherapy Of Cancer.

WO 97/40384, Mass Spectrometry And X-Ray Crystallization Analysis Of Biological Material Via Solid Phase Support.

WO 97/34636, Humanization Of An Anti-Carcinoembryonic Antigen Anti-Idiotype Antibody And Use As A Tumor Vaccine And For Targeting Applications.

WO 97/34632, Glycosylated Humanized B-Cell Specific Antibodies.

WO 97/23237, Use Of Immunoconjugates To Enhance The Efficacy Of Multi-Stage Cascade Boosting Vaccines.

WO 97/11370, Recombinant Proteins Having Multiple Disulfide Bonds And Thiol-Substituted Conjugates Thereof.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

EXAMPLES

Reagents
Mono-DPTA Peptides

```
IMP 233
                                            (SEQ ID NO: 5)
Ac-Phe-Gln-Tyr-Lys(DTPA)-NH₂
```

Described herein

```
IMP 240 Ac-Lys(DPTA)-Cys-NH₂
```

Described herein
Di-DPTA Peptides

```
IMP 156
                                            (SEQ ID NO: 1)
Ac-Phe-Lys(DTPA)-Tyr-Lys(DTPA)-NH₂
```

See Boerman et al., Pretargeting of renal cell carcinoma: improved tumor targeting with a bivalent chelate, *Cancer Res.* 59:4400-5, 1999.

```
IMP 192
                                            (SEQ ID NO: 4)
Ac-Lys(DTPA)-Tyr-Lys(DTPA)-Lys(TSCG-Cys)-NH₂
```

See Karacay et al., Experimental pretargeting studies of cancer with a humanized anti-CEA x murine anti-[In-DTPA] bispecific antibody construct and a (99m)Tc-/(188)Re-labeled peptide, *Bioconjug Chem.* 11:842-54, 2000.

```
IMP 222
                                            (SEQ ID NO: 6)
Ac-Cys-Lys(DTPA)-Tyr-Lys(DTPA)-NH₂
```

Described Herein

```
IMP 240 Ac-Lys(DTPA)-Cys-NH₂
```

Described herein
Tetra-DPTA Peptides

```
IMP 246
        (Core sequence disclosed as SEQ ID NO: 6)
[Ac-Cys-Lys(DTPA)-Tyr-Lys(DTPA)-NH₂]₂

(aka [IMP 222]₂)
```

Described Herein
Bi-Specific Antibodies $$hMN-14IgG-(734scFv)_2$$

See published PCT Application WO 99/66951 by Hansen et al., entitled "Use of Bi-specific Antibodies for Pretargeting Diagnosis and Therapy."

$$hMN-14IgG^{(I253A)}-(734scFv)_2$$

This mutant derivative of hMN-14IgG-(734scFv)$_2$, which has a substitution of its 253rd amino acid residue from isoleucine to alanine, is described in U.S. Provisional Application Ser. No. 60/361,037, which was filed Mar. 1, 2002, and is entitled "Bispecific Antibody Point Mutations for Enhancing Rate of Clearance."

Example 1

Synthesis of Mono-DTPA Peptide IMP 233

IMP 233 Ac-Phe-Gln-Tyr-Lys(DTPA)-NH₂ (SEQ ID NO: 5)

The IMP 233 peptide was synthesized by solid phase peptide synthesis using the Fmoc strategy and Rink Amide Resin (0.25 g, 0.8 mmol/g substitution). The protected amino acids Fmoc-Lys(Aloc)-OH, Fmoc-Tyr(But)-OH, Fmoc-Gln(Trt)OH, Fmoc-Phe-OH and Acetic anhydride were added in that order to the resin.

The Aloc side chain protecting group was removed and the DTPA tetra-t-butyl ester was added. The peptide was cleaved and purified by HPLC to afford 0.009 g of the purified peptide (ESMS MH⁺ 1002).

Example 2

Synthesis of Di-DTPA Peptide IMP 156

```
IMP 156
                                            (SEQ ID NO: 1)
Ac-Phe-Lys(DTPA)-Tyr-Lys(DTPA)-NH₂
```

The IMP 156 peptide was synthesized by solid phase peptide synthesis using the Fmoc method and Rink Amide Resin (or Sieber amide resin). The protected amino acids; Fmoc-Lys(Aloc)-OH, Fmoc-Tyr(But)-OH, Fmoc-Lys(Aloc)OH, Fmoc-Phe-OH and Acetic anhydride were added in that order to the resin.

The Aloc side chain protecting groups were removed and the DTPA tetra-t-butyl ester was added. The peptide was cleaved and purified by HPLC (ESMS MH$^+$ 1377).

Example 3

Synthesis of Di-DTPA Peptide IMP 222

```
IMP 222
                                    (SEQ ID NO: 6)
Ac-Cys-Lys(DTPA)-Tyr-Lys(DTPA)-NH₂
```

The IMP 222 peptide was synthesized by solid phase peptide synthesis using the Fmoc and Rink Amide Resin (0.25 g, 0.8 mmol/g substitution). The protected amino acids; Fmoc-Lys(Aloc)-OH, Fmoc-Tyr(But)-OH, Fmoc-Lys(Aloc)-OH, Fmoc-Cys(Trt)-OH and Acetic anhydride were added in that order to the resin. The Aloc side chain protecting groups were removed and the DTPA tetra-t-butyl ester was added. The peptide was cleaved and purified by HPLC to afford 0.125 g of the purified peptide (ESMS MH$^+$ 1333).

Example 4

Synthesis of Tetra-DTPA Peptide IMP 246

```
IMP 246
    (Core sequence disclosed as SEQ ID NO: 6)
[Ac-Cys-Lys(DTPA)-Tyr-Lys(DTPA)-NH₂]₂
```

The peptide, 0.0531 G (IMP 222, 3.98×10$^{-5}$ MOL, AC-Cys-Lys(DTPA)-Tyr-Lys(DTPA)-NH$_2$) (SEQ ID NO:6) was dissolved in a solution which contained 1.0 mL DMSO, 0.2 mL Diisopropylethylaminie, and 0.3 mL water. The solution was incubated at room temperature for four days and then purified by reverse phase HPLC to afford 0.0336 g of the disulfide (ESMS MH$^+$ 2663).

Example 5

IMP 246 Kits

The peptide (0.0022 g) was dissolved in 100 mL of a solution that contained 0.418 g citric acid and 10.06 g of HPCD buffered at pH 4.3. The solution was sterile filtered through a 0.22 µM MILLEX® GV filter in 1 mL aliquots into vials which were immediately frozen and lyophilized.

Example 6

In-111 Labeling of IMP 246

The In-111 (0.4 mCi) was diluted with 0.5 mL water and added to a lyophilized IMP 246 kit. The solution was incubated at room temperature for 10 min. A 1.5 mL aliquot of a solution containing 2.56×10$^{-5}$ M Indium in 0.5 M NaOAc Buffer pH 7.17 was then added to the kit.

Example 7

Evaluation of Affinity of di-DTPA Peptide IMP 192 Complexes Comprising hMN-14IgG$^{(I253A)}$-(734scFv)$_2$ by HPLC The binding of In-DTPA peptides to the anti-In-DTPA antibody hMN-14IgG$^{(I253A)}$-(734scFv)$_2$ was examined by size exclusion HPLC. The bsMAb was radioiodinated using chloramines-T (Greenwood and Hunter). Binding of the radioiodinated bsMAbs to CEA, WI2 (rat anti-MN-14 idiotypic antibody) and radiolabeled peptidyl DTPA chelate was examined on analytical size exclusion HPLC. Approximately 90% of the radioiodinated bsMAb bound to CEA upon treatment with 10-20× molar excess of CEA. The bsMAb complexed with radiolabeled indium-DTPA chelates (IMP-156 or IMP-192).

An IMP 192 kit was labeled with Tc-99m 20.9 mCi. Aliquots from the kit were diluted and mixed with hMN-14IgG$^{(I253A)}$-(734scFv)$_2$ in the following molar ratios (peptide/Ab) 1:5, 1:1, and 20:1. The peptide/antibody mixtures, the peptide alone and the antibody alone were examined on a BIO-SIL® SEC 250 300 mm×7.8 mm HPC column eluted at 1 mL/min with 0.2 M phosphate buffer pH 6.8.

Figure 3:
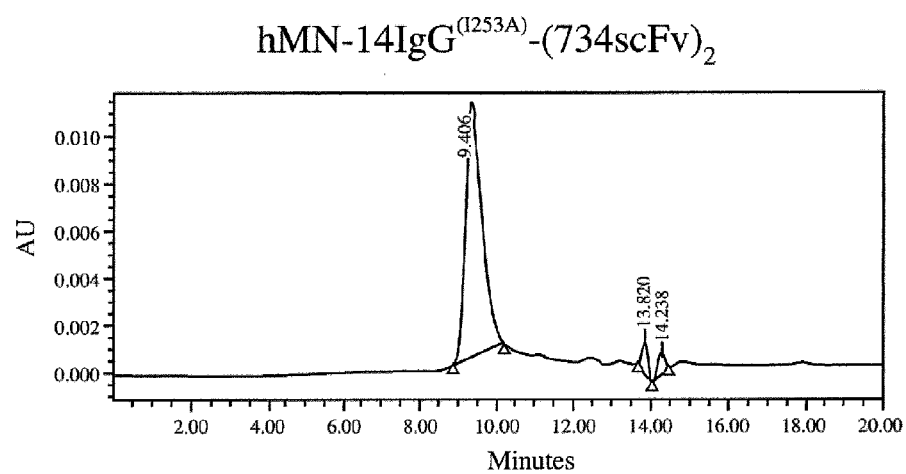
FIGS. 3-7 show HPLC traces of peptide/antibody complexes.
Figure 4:
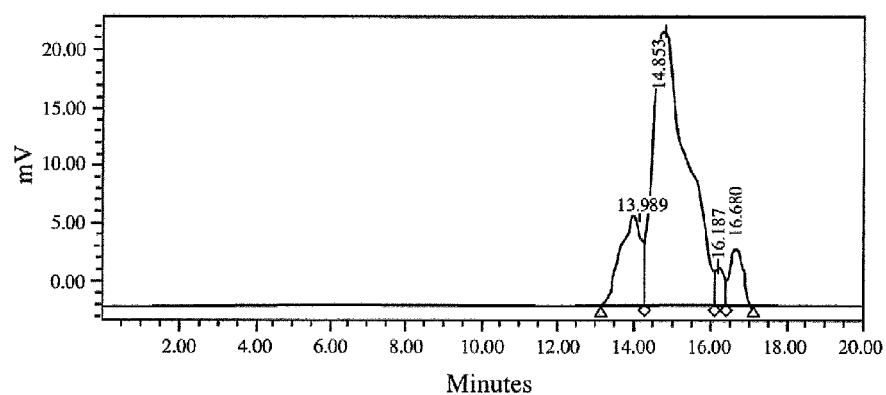
Figure 5:
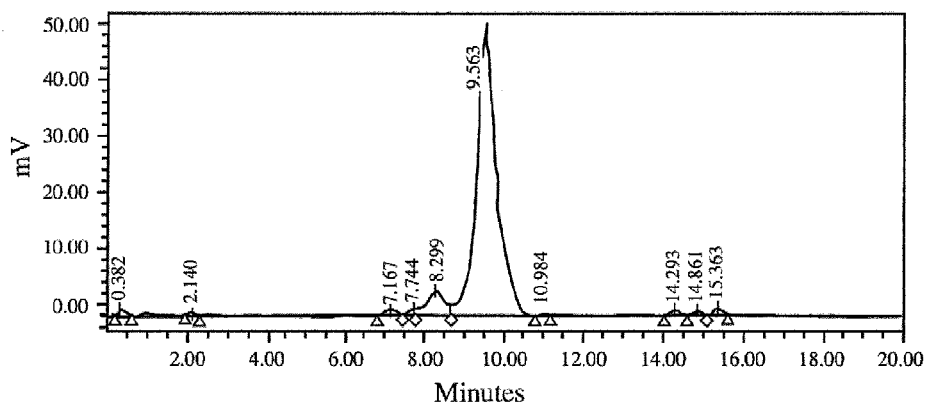
Figure 6:
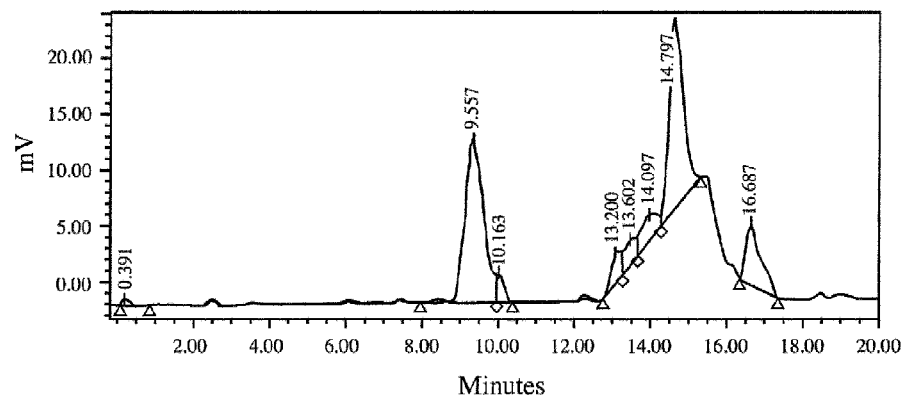
Figure 7:
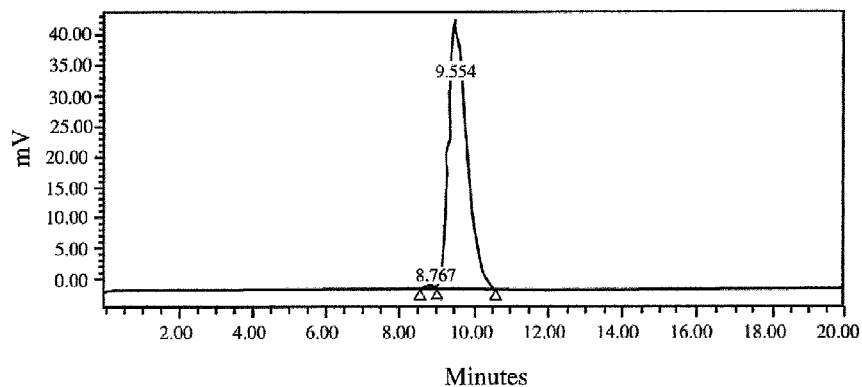

The HPLC traces (FIGS. 3-7) show that essentially only one peptide/antibody complex is formed. A known standard of hMN-14IgG$^{(I253A)}$-(734scFv)$_2$ eluted from the column at about 9.41 minutes (FIG. 3). A known standard of Tc-99m IMP 192 eluted from the column at about 14.85 minutes (FIG. 4). When a 1:1 mixture of hMN-14IgG$^{(I253A)}$-(734scFv)$_2$ to Tc-99m IMP 192 was applied to the column, only one peak was observed at about 9.56 minutes (FIG. 5). In contrast, when a 1:5 mixture of hMN-14IgG$^{(I253A)}$-(734scFv)$_2$ to Tc-99m IMP 192 was applied to the column, two major peaks were observed, one at about 9.56 minutes (hMN-14IgG$^{(I253A)}$-(734scFv)$_2$ and the other at about 14.80 minutes (Tc-99m IMP 192) (FIG. 6). When a 20:1 mixture of hMN-14IgG$^{(I253A)}$-(734scFv)$_2$ to Tc-99m IMP 192 was applied to the column, only one peak was observed at 9.56 minutes (FIG. 7).

Example 8

Stoichiometry of Targetable Complexes

This Example describes experiments designed to determine the stoichiometry of different species of targetable complexes that arise when the targetable divalent construct IMP 246 is mixed with bsAbs hMN-14IgG$^{(I253A)}$-(734scFv)$_2$, and hMN-14IgG-(734scFv)$_2$.

The peptide IMP 246 was dissolved in 100 mL of a solution which contained 0.418 g citric acid and 10.06 g of HPCD buffered at pH 4.3. The solution was filter sterilized through 0.22 µm MILLEX® GV filters in 1 mL aliquots into vials that were immediately frozen and lyophilized.

The IMP 246 was labeled with In-111 as follows. The In-111 was diluted with 0.5 mL water and added to a lyophilized IMP 246 kit. The solution was allowed to incubate at room temperature for 10 min. A 1.5 mL aliquot of a solution containing 2.56×10$^{-5}$ Indium in 0.5 M NaOAc buffer pH 7.17 was then added to the kit.

Figure 8A:
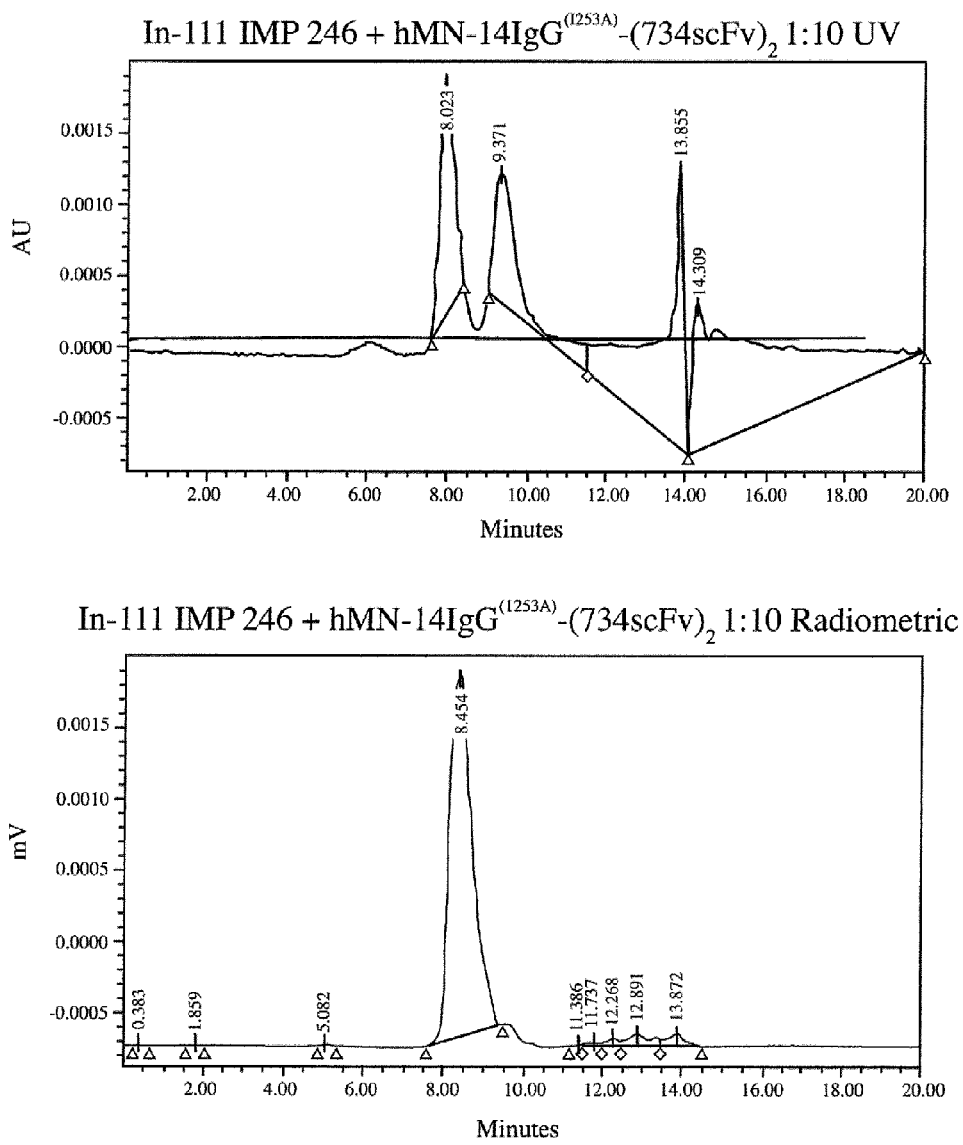
FIG. 8 shows HPLC traces of targetable complexes formed by mixing IMP 246 with hMN-14IgG$^{(J253A)}$-(734scFv)$_2$ (panel A) or with m734 IgG (panel B) mixed in a ratio of 1:10 (peptide:antibody).
Figure 8B:
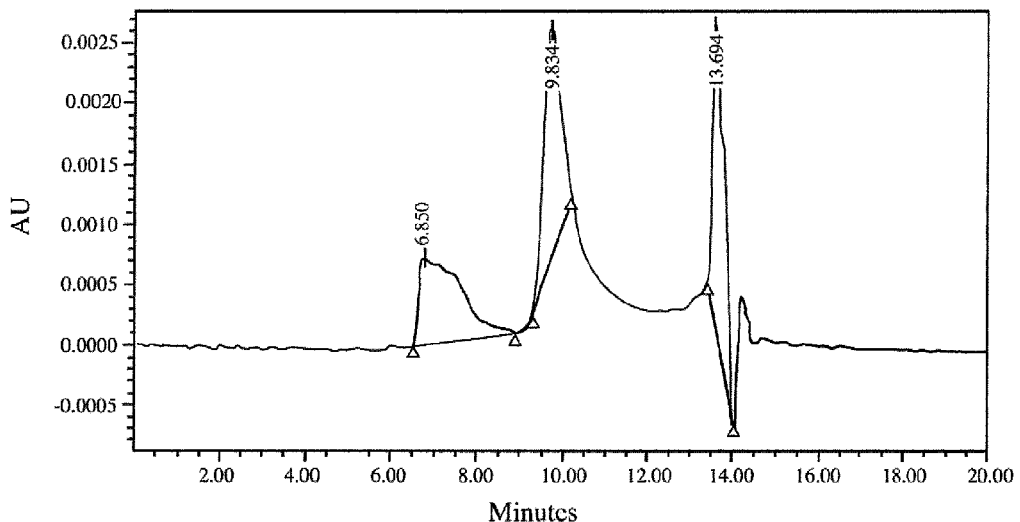
Figure 8B:
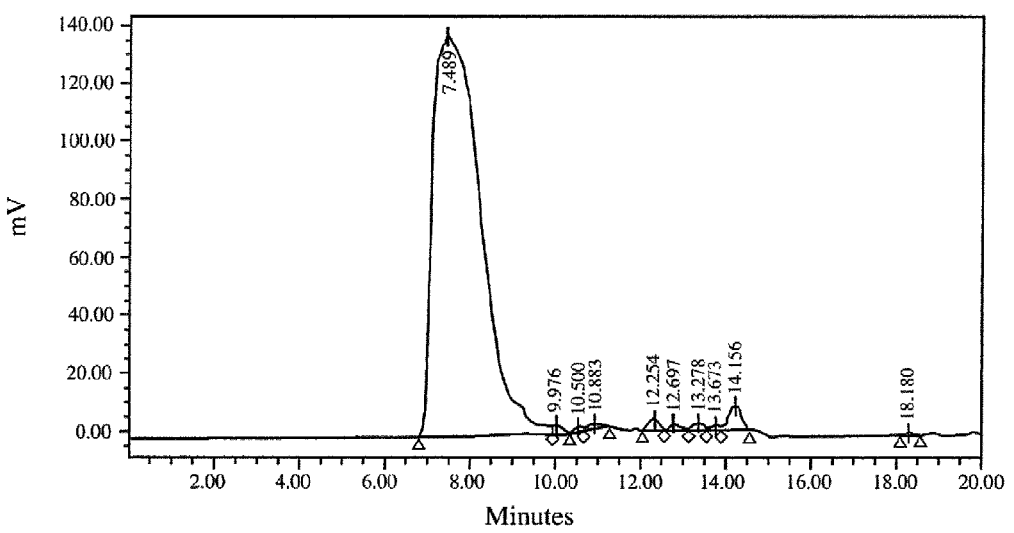

The In-111-labelled IMP 246 was mixed with bsAb in a 1:10 (IMP 246:bsAb) mole ratio and then examined by size exclusion HPLC. The results are shown in FIG. 8. When mixed with the mutant bsAb, i.e., hMN-14IgG$^{(I253A)}$-(734scFv)$_2$, about 90% of the In-111 label was found at a clean sharp peak at 8.5 min (FIG. 8A). When mixed with hMN-14IgG-(734scFv)$_2$, the peak was somewhat broader, comprised about 83% of the In-111 label and was found at 7.5 min (FIG. 8B). In contrast, the antibody:peptide complexes formed when IMP 192 was used were found at 9.5 min (FIG. 7).

Example 9

Synthesis of Mono-DTPA Peptide IMP 240

IMP 240 Ac-Lys(DTPA)-Cys-NH$_2$

The Tetra t-butyl ester of DTPA (J Med Chem 1996 Aug. 30; 39(18):3451-60, Reassessment of diethylenetriaminepentaacetic acid (DTPA) as a chelating agent for indium-111 labeling of polypeptides using a newly synthesized monoreactive DIVA derivative. Arano Y, Uezono T, Akizawa H, Ono M, Wakisaka K, Nakayama M, Sakahara H, Konishi J, Yokoyama A.) 1.424 g was dissolved in 5.5 mL dioxane. N-Hydroxysuccinimide, 0.304 g was added followed by 0.4 mL of diisopropylcarbodiimide (DIC) and mixed for 1 hr at room temperature. The remaining reagents 1.049 g Na$_2$CO$_3$ and 0.862 g Ac-Lys-OH were mixed then added 5 mL water was added. The lysine/carbonate solution was then mixed with the activated DIVA reagent. The reaction was stirred at room temperature overnight and then quenched with 20 mL 1M citric acid. The citric acid solution was extracted with 2×50 mL portions of chloroform, dried over Na$_2$SO$_4$ and concentrated under reduced pressure to obtain 2.031 g of crude product. The crude product was dissolved in 6 mL dioxane and mixed with 0.264 g N-Hydroxysuccinimide and 0.38 mL DIC. The reaction was mixed at room temperature for 2.5 hr then 0.414 g H-Cys(Trt)-NH$_2$ was added along with 0.3 mL diisopropylethylamine. The reaction was stirred at room temperature overnight and then filtered. The solids were washed with dioxane and the filtrates were combined. The crude product was concentrated under reduced pressure. The crude product was treated with a cleavage solution of 25 mL Trifluoro acetic acid, 1 mL triisopropylsilane and 1 mL anisole. The cleavage reaction mixture was poured into 2×40 mL ether after 3.5 hr. The peptide was collected by centrifugation. The precipitated peptide was washed with 3×30 mL ether. The precipitate was dried then purified by reverse phase HPLC to obtain 0.2152 g of the desired product MNa$^+$688.

Example 10

Binding Studies Using Surface Plasmon Resonance

The binding of In-DTPA peptides to the anti-In-DTPA antibody hMN-14IgG$^{(I253A)}$-(734scFv)$_2$ was examined by affinity blocking studies using the IMP 240 peptide, Ac-Lys(DPTA)-Cys-NH$_2$, which comprises a single DPTA group and a single Cys residue that can be used to form disulfide bridges with a second molecule having a free sulfhydryl group.

Preparation of IMP 240-Coated BIACORE® Chip

The binding studies were performed on a chip coated with IMP 240 using the disulfide connection as recommended by BIACORE®. The chip surface was regenerated after each assay with 100 µL 0.025 M In-DTPA in HBS-In-citrate buffer as described. The binding studies were done with picomoles of antibody therefore binding was very sensitive to the slightest trace of In-DTPA left after the displacement wash.

IMP 156 Binding to hMN-14IgG$^{(I253A)}$-(734scFv)$_2$

The affinity studies show that when IMP 156 was mixed with hMN-14IgG$^{(I253A)}$-(734scFv)$_2$ in a 1:1 ratio the antibody binding to the IMP 240 chip was blocked. This indicates that both 734 binding sites were filled with the two DTPA's on a single peptide.

IMP 233 Binding to hMN-14IgG$^{(I253A)}$-(734scFv)$_2$

The affinity studies show the binding of the antibody was not completely blocked even when four equivalents of the mono-DTPA peptide were premixed with the antibody. Although not wishing to be bound by any particular theory, this is probably due to the dissociation of a portion of the mono-DTPA peptide from the antibody during the test.

Binding Studies of IMP 156 Binding to c734 IgG

Studies were performed with c734-IgG to compare the In-DTPA peptide binding behavior of this IgG to the hMN-14IgG$^{(I253A)}$-(734scFv)$_2$. It was necessary to add two or more equivalents of IMP 156 to block the binding of c734 to the chip whereas the hMN-14IgG$^{(I253A)}$-(734scFv)$_2$ was blocked by one equivalent of IMP 156.

This indicates that both In/DTPA's of IMP 156 were simultaneously bound to both scFv's of hMN-14IgG$^{(I253A)}$-(734scFv)$_2$ whereas only one In/DTPA of IMP 156 was bound to the binding arm of c734-IgG and another In/DTPA on another molecule of IMP 156 was needed to block the other binding arm of c734-IgG.

Binding Studies of IMP 233 Binding to c734 IgG

The affinity studies showed that even 4:1 IMP 233/c734 IgG did not completely block the binding of the antibody to the IMP 240 chip.

This experiment demonstrated that it was difficult to completely block the binding of the binding of c734 IgG to the IMP 240 chip with a peptide bearing a single In-DTPA (IMP 233). This meant that either there was a certain amount of free c734 IgG (or at least one binding arm available for binding) or the In-DTPA on the chip was able to displace the In-DTPA of IMP 233. The fact that IMP 156 completely blocked the binding of hMN-14IgG$^{(I253A)}$-(734scFv)$_2$ (when mixed in a 1:1 ratio Peptide:Antibody) to the IMP 240 chip demonstrated that both of the DTPA binding sites were filled and that the affinity of the hMN-14IgG$^{(I253A)}$-(734scFv)$_2$ for In-IMP 156 was far higher than the affinity of a single In-DTPA for a c734 IgG binding arm.

Example 11

Attachment of IMP 222 to a BIAcore Chip

The CM-5 Chip has a carbohydrate attached to a gold surface which has been derivitized with carboxylic acids. The carboxylic acids on the surface were activated with NHS (N-hydroxysuccinimide) and a water soluble carbodiimide, EDC (N-ethyl-N'-(3-dimethyl aminopropyl)-carbodiimide hydrochloride) essentially according to the manufacturer's instructions.

A solution of 2-(2-pyridinylthio)ethaneamine hydrochloride (PDEA) in 0.1 M pH 8.5 borate buffer was then added essentially according to the manufacturer's instructions. The IMP 222 peptide, Ac-Cys-Lys(DTPA)-Tyr-Lys(DTPA)-NH$_2$ (SEQ ID NO:6), was dissolved in 0.01 M pH 4.3 formate buffer then added to the chip as described.

The peptide forms a disulfide linkage to the chip when added in this manner. Finally, the remaining unreacted active ester and PDEA are quenched by the addition of a solution containing cysteine and NaCl in 0.1 M formate buffer pH 4.3.

Example 12

Serum Stability

Stability of bsAb in Serum

Bi-specific antibody (bsAb) was radioiodinated and tested for stability in fresh human serum at 37° C. under a humidified 5% $CO_2$ atmosphere. Aliquots were examined on SE-HPLC. In order to detect radioiodine associated with serum proteins, the aliquots were mixed with WI2 to shift the bsMAb peak to earlier retention times. The bsMAbs showed about 3-5% loss of binding capacity to WI2 after 48 h incubation in serum. Slight aggregate formation (about 4-7%) was observed upon incubation of the bsMAbs in serum for 72 hours.

Stability of Targetable Constructs in Serum

A 40 μL aliquot of the labeled peptide was diluted with 400 μL of fresh mouse serum and incubated at 37° C. for 17.5 hours. A 10 μL aliquot was removed and mixed with 5 μl, of 3.2 mg/mL 14IgG$^{(J253A)}$-(734scFv)$_2$ and diluted with 40 μL water. A 10 μl aliquot of the diluted mixture was then examined by size exclusion HPLC.

Stability of Targetable Complexes in Serum

Peptide Plus hMN-14IgG$^{(J253A)}$-(734scFv)$_2$ Serum Stability:

A 4 μL aliquot of the labeled peptide solution was mixed with 10 μL of the 3.2 mg/mL hMN-14 IgG$^{(J253A)}$-(734scFv)$_2$ and diluted in 400 μL of fresh mouse serum. The serum sample was incubated at 37° C. for 16 hr and then analyzed by size exclusion HPLC.

The IMP 246 peptide was unstable in mouse serum after 16 hours, as demonstrated by the presence of several overlapping peaks in the HPLC tracing. Three broad peaks comprised about 20%, 41% and 37% of the area under the curve of the HPLC tracing. In contrast, the stability of IMP 246 was greatly increased in the presence of the bi-specific antibody, as 90% of the area under the curve of the HPLC tracing was found in a distinct peak at the predicted position.

Example 13

Evaluation of Complexes Comprising hA20-IgG-(734scFv)$_2$ in vitro hA20-IgG-(734scFv)$_2$ is made using methods described in PCT Application Publication No. WO 99/66951 by Hansen et al., with the only change being that cDNA coding for the variable chains of hA20 is used in place of cDNA coding for hMN-14 variable chains. The cDNA coding for the constant regions of both hMN-14 and hA20 are identical, as is the cDNA coding for the linker and scFv of monoclonal antibody 734.

Raji cells in culture are incubated with hA20IgG-(734scFv)$_2$. To one set of wells is added IMP-246 to cross-link molecules of hA20IgG-(734scFv)$_2$ bound to CD20 on the surface of the Raji cells. A second set of wells to which IMP-246 is not added serve as controls, and both sets of wells incubated at 37 degrees C. After 3 days, the cells to which IMP-246 was added are determined to have undergone extensive apoptosis. Minimal apoptosis was observed in the control wells to which IMP-246 was not added.

An average of 5 molecules IMP-222 are conjugated to human serum albumin (hAlb-222). The experiment described in the paragraph above is repeated, but hAb-222 is used to cross-link molecules of hA20IgG-(734scFv)$_2$ bound to CD20 on the surface of the Raji cells, in place of IMP-246. Extensive apoptosis of cells is observed in wells to which hAlb-222 was added.

Illustrated Embodiments

Additional embodiments are within the scope of the invention. For example, the invention is further illustrated by the following numbered embodiments:

1. A targetable construct comprising (i) a molecular scaffold and (ii) two pairs of a carrier epitope, wherein said targetable construct, when combined with a bi-specific antibody comprising (i) two copies of a first arm comprising a binding site for said carrier epitope, and (ii) two copies of a second arm comprising a binding site for a target epitope, forms a targetable complex, wherein one or more of the following applies:

(a) said targetable complexes have a Kd for said target epitope from about 0.1 nM to about 100 nM, (b) mixing said targetable construct and said bi-specific antibody at relative concentrations ranging from about $10^{-3}$ to about $10^3$ results in a mixture in which greater than about 75% of the complexes therein have a defined stoichiometry of two molecules of said bi-specific antibody, and one molecule of said targetable construct, and (c) a pair of carrier epitopes is simultaneously bound by said two copies of a first arm comprising a binding site for said carrier epitope, wherein said two copies of a first arm comprising a binding site for said carrier epitope are part of said bi-specific antibody.

2. The targetable construct of embodiment 1, wherein mixing said targetable construct and said bi-specific antibody at relative concentrations ranging from about $10^{-3}$ to about $10^3$ results in a mixture in which greater than about 85% of the multimeric complexes have a defined stoichiometry of two molecules of said bi-specific antibody, and one molecule of said targetable construct.

3. The targetable construct of embodiment 1, wherein mixing said targetable construct and said bi-specific antibody at relative concentrations ranging from about $10^{-3}$ to about $10^3$ results in a mixture in which greater than about 95% of the multimeric complexes have a defined stoichiometry of two molecules of said bi-specific antibody, and one molecule of said targetable construct.

4. The targetable construct of embodiment 1, wherein mixing said targetable construct and said bi-specific antibody at relative concentrations ranging from about $10^{-3}$ to about $10^3$ results in a mixture in which greater than about 99% of the multimeric complexes have a defined stoichiometry of two molecules of said bi-specific antibody and one molecule of said targetable construct.

5. The targetable construct of embodiment 1, wherein said Kd for said target epitope is from about 0.1 nM to 10 nM.

6. The targetable construct of embodiment 5, wherein said Kd for said target epitope is from about 0.5 nM to about 5 nM.

7. The targetable construct of embodiment 6, wherein said Kd for said target epitope is about 1 nM.

8. The targetable construct of embodiment 1, wherein said molecular scaffold is a peptide or peptide derivative.

9. The targetable construct of embodiment 1, wherein targetable construct is IMP 246.

10. The targetable construct of embodiment 1, wherein said targetable construct comprises two constructs that are conjugated to each other, wherein each construct comprises a molecular scaffold and a pair of carrier epitopes.

11. The targetable construct of embodiment 10, wherein each of said constructs is independently selected from the group consisting of IMP 156, IMP 192 and IMP 222.

12. The targetable construct of embodiment 1, wherein said carrier epitope is a hapten.

13. The targetable construct of embodiment 1, wherein said carrier epitope is a chelator, or a complex between a chelator and a metal ion.

14. The targetable construct of embodiment 13, wherein said chelator is selected from the group consisting of DTPA, DOTA, benzyl DTPA, NOTA, and ETA.

15. The targetable construct of embodiment 1, wherein said bi-specific antibody is [IgG]-[scFv]2; wherein IgG is a human, chimeric or CDR-grafted antibody; further wherein scFv is a human, chimeric or CDR-grafted single chain antibody specific for a hapten; and further wherein said scFv is extended from the carboxyl terminal amino acid of the heavy chains of said IgG by a linker peptide.

16. The targetable construct of embodiment 15, wherein said bi-specific antibody is selected from the group consisting of hMN-14IgG-(734scFv)$_2$ and hMN-14IgG$^{(I253A)}$-(734scFv)$_2$.

17. The targetable construct of embodiment 15, wherein said bi-specific antibody is selected from the group consisting of hMN-14IgG-(679scFv)$_2$ and hMN-14IgG$^{(I253A)}$-(679scFv)$_2$.

18. The targetable construct of embodiment 15, wherein said bi-specific antibody is selected from the group consisting of hA20IgG-(734scFv)$_2$ and hA20IgG$^{(I253A)}$-(734scFv)$_2$.

19. The targetable construct of embodiment 15, wherein said bi-specific antibody is selected from the group consisting of hA20IgG-(679scFv)$_2$ and hA20IgG$^{(I253A)}$-(679scFv)$_2$.

20. The targetable construct of embodiment 15, wherein said bi-specific antibody is selected from the group consisting of hLL2IgG-(734scFv)$_2$ and hLL2IgG$^{(I253A)}$-(734scFv)$_2$.

21. The targetable construct of embodiment 15, wherein said bi-specific antibody is selected from the group consisting of hLL2IgG-(679scFv)$_2$ and hLL2IgG$^{(I253A)}$-(670scFv)$_2$.

22. The targetable construct of embodiment 1, wherein said targetable construct further comprises a bioactive moiety.

23. The targetable construct of embodiment 22, wherein said bioactive moiety is selected from the group consisting of a drug, a prodrug, an enzyme, a hormone, an immunomodulator, an oligonucleotide; a radionuclide, an image enhancing agent and a toxin.

24. The targetable construct of embodiment 23, wherein said enzyme is selected from the group consisting of malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

25. The targetable construct of embodiment 23, wherein said immunomodulator is selected from the group consisting of a cytokine, a stem cell growth factor, a lymphotoxin, a hematopoietic growth factor, a colony stimulating factor (CSF), an interferon (IFN), erythropoietin, thrombopoietin and a combination thereof.

26. The targetable construct of embodiment 23, wherein said immunomodulator consists essentially of IL-1, IL-2, IL-3, IL-6, IL-10, IL-12, IL-18, IL-21, G-CSF, GM-CSF, interferon-γ, -α, -β or -γ, TNF-α, and "S1 factor.

27. The targetable construct of embodiment 23, wherein said oligonucleotide is an anti-sense oligonucleotide.

28. The targetable construct of embodiment 27, wherein said anti-sense oligonucleotide is bcl-2 or p53.

29. A solid support to which the targetable construct of embodiment 1 is bound.

30. A biosensor comprising the targetable construct of embodiment 1.

31. A targetable construct comprising (i) a molecular scaffold and (ii) two pairs of carrier epitopes, wherein the first of said two pairs of carrier epitopes is specifically bound by a first bi-specific antibody, and the second of said two pairs of carrier epitopes is specifically bound by a second bi-specific antibody, wherein said targetable construct forms a targetable complex when combined with (i) a first bi-specific antibody, said first bi-specific antibody comprising (a) two copies of a first arm comprising a binding site for said carrier epitope, and (b) two copies of a second arm comprising a binding site for a first target epitope, and (ii) a second bi-specific antibody, said second bi-specific antibody comprising (a) two copies of a first arm comprising a binding site for said carrier epitope, and (b) two copies of a second arm comprising a binding site for a second target epitope;

wherein said first bi-specific antibody and said second bi-specific antibody can be the same or different, said pairs of carrier epitopes can be the same or different, and said target epitopes can be the same or different, and wherein one or more of the following applies:

(a) said targetable complex has a Kd of from about 0.1 nM to about 100 nM for either or both of said target epitopes, (b) mixing said targetable construct and said bi-specific antibodies at relative concentrations ranging from about $10^{-3}$ to about $10^3$ results in a mixture in which greater than about 75% of the multimeric complexes have a defined stoichiometry of one molecule of said first bi-specific antibody, one molecule of said second bi-specific antibody, and one molecule of said targetable construct; and (c) a pair of carrier epitopes is simultaneously bound by said two copies of a first arm comprising a binding site for said carrier epitope, wherein said two copies of a first arm comprising a binding site for said carrier epitope are part of said bi-specific antibody.

32. The targetable construct of embodiment 31, wherein said pairs of carrier epitopes are different, but said target epitopes are the same.

33. The targetable construct of embodiment 31, wherein said first antibody and said second antibody are different, but said target epitopes are the same.

34. The targetable construct of embodiment 31, wherein said carrier epitopes are the same, and said first arm comprising a binding site for said carrier epitope of said first bi-specific antibody and said first arm comprising a binding site for said carrier epitope of said second bi-specific antibody are the same, but said first target epitope and said second target epitope are not the same.

35. The targetable construct of embodiment 31, wherein mixing said targetable construct and said bi-specific antibodies at relative concentrations ranging from about $10^{-3}$ to about $10^3$ results in a mixture in which greater than about 85% of the multimeric complexes have a defined stoichiometry of two molecules of said bi-specific antibody or antibody derivative and one molecule of said targetable construct.

36. The targetable construct of embodiment 31, wherein mixing said targetable construct and said bi-specific antibody at relative concentrations ranging from about $10^{-3}$ to about $10^3$ results in a mixture in which greater than about 95% of the multimeric complexes have a defined stoichiometry of two molecules of said bi-specific antibody or antibody derivative and one molecule of said targetable construct.

37. The targetable construct of embodiment 31, wherein mixing said targetable construct and said bi-specific antibody at relative concentrations ranging from about $10^{-3}$ to about $10^3$ results in a mixture in which greater than about 99% of the multimeric complexes have a defined stoichiometry of two molecules of said bi-specific antibody or antibody derivative and one molecule of said targetable construct.

38. The targetable construct of embodiment 31, wherein said Kd for said target epitope is from about 0.1 nM to 10 nM.

39. The targetable construct of embodiment 38, wherein said Kd for said target epitope is from about 0.5 nM to about 5 nM.

40. The targetable construct of embodiment 39, wherein said Kd for said target epitope is about 1 nM.

41. The targetable construct of embodiment 31, wherein said targetable construct comprises two constructs that are conjugated to each other, wherein each construct comprises a molecular scaffold and a pair of carrier epitopes.

42. The targetable construct of embodiment 41, wherein each of said constructs is independently selected from the group consisting of IMP 156, IMP 192 and IMP 222.

43. The targetable construct of embodiment 31, wherein said molecular scaffold is a peptide or peptide derivative.

44. The targetable construct of embodiment 31, wherein said carrier epitope is a hapten.

45. The targetable construct of embodiment 31, wherein said carrier epitope is a chelator, or a complex between a chelator and a metal ion.

46. The targetable construct of embodiment 45, wherein said chelator is selected from the group consisting of DTPA, DOTA, benzyl DTPA, NOTA, and TSTA.

47. The targetable construct of embodiment 31, wherein said targetable construct further comprises a bioactive moiety.

48. The targetable complex of embodiment 47, wherein said bioactive moiety is selected from the group consisting of a drug, a prodrug, an enzyme, a hormone, an immunomodulator, an oligonucleotide, a radionuclide, an image enhancing agent and a toxin.

49. The targetable construct of embodiment 48, wherein said enzyme is selected from the group consisting of malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

50. The targetable construct of embodiment 48, wherein said immunomodulator is selected from the group consisting of a cytokine, a stem cell growth factor, a lymphotoxin, a hematopoietic growth factor, a colony stimulating factor (CSF), an interferon (IFN), erythropoietin, thrombopoietin and a combination thereof.

51. The targetable construct of embodiment 48, wherein said immunomodulator consists essentially of IL-1, IL-2, IL-3, IL-6, IL-10, IL-12, IL-18, IL-21, G-CSF, GM-CSF, interferon-γ, -α, -β or -γ, TNF-α, and "S1 factor.

52. The targetable construct of embodiment 48, wherein said oligonucleotide is an anti-sense oligonucleotide.

53. The targetable construct of embodiment 52, wherein said anti-sense oligonucleotide is bcl-2 or p53.

54. The targetable construct of embodiment 34, wherein said first arm comprising a binding site for said carrier epitope of said first bi-specific antibody, and said first arm comprising a binding site for said carrier epitope of said second bi-specific antibody, are both [734scFv]$_2$.

55. A solid support to which the targetable construct of embodiment 31 is bound.

56. A biosensor comprising the targetable construct of embodiment 31.

57. A targetable construct comprising a molecular scaffold and X pairs of carrier epitopes, wherein each of said pairs of carrier epitopes is specifically bound by one of X bi-specific antibodies, each bi-specific antibody comprising (a) two copies of a first arm comprising a binding site for a carrier epitope, and (b) two copies of a second arm comprising a binding site for one of Y target epitopes, and wherein
(i) X is a whole integer 3,
(ii) Y is a whole integer 1,
(iii) said X bi-specific antibodies can be the same or a mixture of different bi-specific antibodies,
(iv) said X pairs of carrier epitopes can be the same or a mixture of different carrier epitopes, and
(v) when Y≧2, said Y target epitopes can be the same or a mixture of different target epitopes,
and wherein one or more of the following applies:
(a) said targetable complex has a Kd of from about 0.1 nM to about 100 nM for at least one of said target epitopes,
(b) a pair of carrier epitopes is simultaneously bound by said two copies of a first arm comprising a binding site for said carrier epitope, wherein said two copies of a first arm comprising a binding site for said carrier epitope are part of said bi-specific antibody.

58. The targetable construct of embodiment 57, wherein said Kd for at least one of said target epitopes is from about 0.1 nM to 10 nM.

59. The targetable construct of embodiment 58, wherein said Kd for at least one of said target epitopes is from about 0.5 nM to about 5 nM.

60. The targetable construct of embodiment 59, wherein said Kd for at least one of target epitope is about 1 nM.

61. The targetable construct of embodiment 57, wherein said molecular scaffold is a peptide or peptide derivative.

62. The targetable construct of embodiment 57, wherein at least one of said carrier epitopes is a hapten.

63. The targetable construct of embodiment 57, wherein said targetable construct further comprises a bioactive moiety.

64. The targetable construct of embodiment 63, wherein said bioactive moiety is selected from the group consisting of a drug, a prodrug, an enzyme, a radionuclide, an image enhancing agent and a toxin.

65. The targetable construct of embodiment 64, wherein said enzyme is selected from the group consisting of malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

66. The targetable construct of embodiment 64, wherein said immunomodulator is selected from the group consisting of a cytokine, a stem cell growth factor, a lymphotoxin, a hematopoietic growth factor, a colony stimulating factor (CSF), an interferon (IFN), erythropoietin, thrombopoietin and a combination thereof.

67. The targetable construct of embodiment 64, wherein said immunomodulator consists essentially of IL-1, IL-2, IL-3, IL-6, IL-10, IL-12, IL-18, IL-21, G-CSF, GM-CSF, interferon-γ, -α, -β or -γ, TNF-α, and "S1 factor.

68. The targetable construct of embodiment 64, wherein said oligonucleotide is an anti-sense oligonucleotide.

69. The targetable construct of embodiment 68, wherein said anti-sense oligonucleotide is bcl-2 or p53.

70. A solid support to which the targetable construct of embodiment 57 is bound.

71. A biosensor comprising the targetable construct of embodiment 57.

72. A targetable complex comprising four arms capable of binding a target epitope, said tetravalent targetable complex comprising:
(a) a targetable construct comprising (i) a molecular scaffold and (ii) two pairs of a carrier epitope; and
(b) two molecules of a bi-specific antibody, each antibody comprising (i) two arms, each arm comprising a binding site for said carrier epitope, and (ii) two arms, each comprising a binding site for said target epitope,
wherein one or more of the following applies:
(I) said targetable complexes have a Kd for said target epitope from about 0.1 nM to about 100 nM,
(II) mixing said targetable construct and said bi-specific antibody at relative concentrations ranging from about $10^{-3}$ to about $10^3$ results in a mixture in which greater than about 75% of the complexes therein have a defined stoichiometry of two molecules of said bi-specific antibody, and one molecule of said targetable construct, and
(III) a pair of carrier epitopes is bound by said bi-specific antibody in a 1:1 ratio.

73. The targetable complex of embodiment 72, wherein mixing said targetable construct and said bi-specific antibody at relative concentrations ranging from about $10^{-3}$ to about $10^3$ results in a mixture in which greater than about 85% of the multimeric complexes have a defined stoichiometry of two molecules of said bi-specific antibody, and one molecule of said targetable construct.

74. The targetable complex of embodiment 72, wherein mixing said targetable construct and said bi-specific antibody at relative concentrations ranging from about $10^{-3}$ to about $10^3$ results in a mixture in which greater than about 95% of the multimeric complexes have a defined stoichiometry of two molecules of said bi-specific antibody, and one molecule of said targetable construct.

75. The targetable complex of embodiment 72, wherein mixing said targetable construct and said bi-specific antibody at relative concentrations ranging from about $10^{-3}$ to about $10^3$ results in a mixture in which greater than about 99% of the multimeric complexes have a defined stoichiometry of two molecules of said bi-specific antibody, and one molecule of said targetable construct.

76. The targetable complex of embodiment 72, wherein said Kd for said target epitope is from about 0.1 nM to 10 nM.

77. The targetable complex of embodiment 76, wherein said Kd for said target epitope is from about 0.5 nM to about 5 nM.

78. The targetable complex of embodiment 77, wherein said Kd for said target epitope is about 1 nM.

79. The targetable complex of embodiment 72, wherein said molecular scaffold is a peptide or peptide derivative.

80. The targetable complex of embodiment 72, wherein said targetable construct is IMP 246.

81. The targetable complex of embodiment 72, wherein said targetable construct comprises two constructs that are conjugated to each other, wherein each construct comprises a molecular scaffold and a pair of carrier epitopes.

82. The targetable complex of embodiment 81, wherein each of said constructs is independently selected from the group consisting of IMP 156, IMP 192 and IMP 222.

83. The targetable complex of embodiment 72, wherein said carrier epitope is a hapten.

84. The targetable complex of embodiment 72, wherein said carrier epitope is a chelator, or a complex between a chelator and a metal ion.

85. The targetable complex of embodiment 84, wherein said chelator is selected from the group consisting of DTPA, DOTA, benzyl DTPA, NOTA, and TETA.

86. The targetable complex of embodiment 72, wherein said bi-specific antibody is selected from the group consisting of hMN-14IgG-(734scFv)$_2$ and hMN-14IgG$^{(J253A)}$-(679scFv)$_2$.

87. The targetable complex of embodiment 72, wherein at least one arm comprising a binding site for said carrier epitope is 734scFv.

88. The targetable complex of embodiment 72, wherein said targetable construct further comprises a bioactive moiety.

89. The targetable complex of embodiment 88, wherein said bioactive moiety is selected from the group consisting of a drug, a prodrug, an enzyme, a radionuclide, an image enhancing agent and a toxin.

90. The targetable construct of embodiment 89, wherein said enzyme is selected from the group consisting of malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

91. The targetable construct of embodiment 89, wherein said immunomodulator is selected from the group consisting of a cytokine, a stem cell growth factor, a lymphotoxin, a hematopoietic growth factor, a colony stimulating factor (CSF), an interferon (IFN), erythropoietin, thrombopoietin and a combination thereof.

92. The targetable construct of embodiment 89, wherein said immunomodulator consists essentially of IL-1, IL-2, IL-3, IL-6, IL-10, IL-12, IL-18, IL-21, G-CSF, GM-CSF, interferon-γ, -α, -β or -γ, TNF-α, and "S1 factor.

93. The targetable construct of embodiment 89, wherein said oligonucleotide is an anti-sense oligonucleotide.

94. The targetable construct of embodiment 93, wherein said anti-sense oligonucleotide is bcl-2 or p53.

95. A solid support to which the targetable complex of embodiment 72 is bound.

96. A biosensor comprising the targetable complex of embodiment 72.

97. A targetable complex, said targetable complex comprising:
(a) a targetable construct comprising (i) a molecular scaffold and (ii) two pairs of carrier epitopes, wherein the first of said two pairs of carrier epitopes is specifically bound by a first bi-specific antibody, and the second of said two pairs of carrier epitopes is specifically bound by a second bi-specific antibody, wherein said targetable construct forms a targetable complex when combined with
(b) a first bi-specific antibody, said first bi-specific antibody comprising (i) two copies of a first arm comprising a binding site for said carrier epitope, and (ii) two copies of a second arm comprising a binding site for a first target epitope, and (c) a second bi-specific antibody, said second bi-specific antibody comprising (i) two copies of a first arm comprising a binding site for said carrier epitope, and (ii) two copies of a second arm comprising a binding site for a second target epitope;

wherein said first bi-specific antibody and said second bi-specific antibody can be the same or different, said pairs of carrier epitopes can be the same or different, and said target epitopes can be the same or different, and wherein one or more of the following applies (I) said targetable complexes have a Kd for said target epitope from about 0.1 nM to about 100 nM, (II) mixing said targetable construct and said bi-specific antibody at relative concentrations ranging from about $10^{-3}$ to about $10^3$ results in a mixture in which greater than about 75% of the complexes therein have a defined stoichiometry of two molecules of said bi-specific antibody, and one molecule of said targetable construct, and (III) each of said pairs of carrier epitopes is bound by one of said bi-specific antibodies in a 1:1 ratio.

98. The targetable complex of embodiment 97, wherein mixing said targetable construct and said bi-specific antibody at relative concentrations ranging from about $10^{-3}$ to about $10^3$ results in a mixture in which greater than about 85% of the multimeric complexes have a defined stoichiometry of two molecules of said bi-specific antibody, and one molecule of said targetable construct.

99. The targetable complex of embodiment 97, wherein mixing said targetable construct and said bi-specific antibody at relative concentrations ranging from about $10^{-3}$ to about $10^3$ results in a mixture in which greater than about 95% of the multimeric complexes have a defined stoichiometry of two molecules of said bi-specific antibody, and one molecule of said targetable construct.

100. The targetable complex of embodiment 97, wherein mixing said targetable construct and said bi-specific antibody at relative concentrations ranging from about $10^{-3}$ to about $10^3$ results in a mixture in which greater than about 99% of the multimeric complexes have a defined stoichiometry of two molecules of said bi-specific antibody, and one molecule of said targetable construct.

101. The targetable complex of embodiment 97, wherein said Kd for said target epitope is from about 0.1 nM to 10 nM.

102. The targetable complex of embodiment 101, wherein said Kd for said target epitope is from about 0.5 nM to about 5 nM.

103. The targetable complex of embodiment 102, wherein said Kd for said target epitope is about 1 nM.

104. The targetable complex of embodiment 97, wherein said molecular scaffold is a peptide or peptide derivative.

105. The targetable complex of embodiment 97, wherein said targetable construct is IMP 246.

106. The targetable complex of embodiment 97, wherein said targetable construct comprises two constructs that are conjugated to each other, wherein each construct comprises a molecular scaffold and a pair of carrier epitopes.

107. The targetable complex of embodiment 107, wherein each of said constructs is independently selected from the group consisting of IMP 156, IMP 192 and IMP 222.

108. The targetable complex of embodiment 97, wherein said carrier epitope is a hapten.

109. The targetable complex of embodiment 97, wherein said carrier epitope is a chelator, or a complex between a chelator and a metal ion.

110. The targetable complex of embodiment 110, wherein said chelator is selected from the group consisting of DTPA, DOTA, benzyl DTPA, NOTA, and TETA.

111. The targetable complex of embodiment 97, wherein said bi-specific antibody is selected from the group consisting of $[hMN]_2$-$[734scFv]_2$ and $[hMN^{(I253A)}]_2$-$[734scFvh]_2$.

112. The targetable complex of embodiment 97, wherein at least one arm comprising a binding site for said carrier epitope is 734scFv.

113. The targetable complex of embodiment 97, wherein said targetable construct further comprises a bioactive moiety.

114. The targetable complex of embodiment 113, wherein said bioactive moiety is selected from the group consisting of a drug, a prodrug, an enzyme, a radionuclide, an image enhancing agent and a toxin.

115. The targetable construct of embodiment 114, wherein said enzyme is selected from the group consisting of malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

116. The targetable construct of embodiment 114, wherein said immunomodulator is selected from the group consisting of a cytokine, a stem cell growth factor, a lymphotoxin, a hematopoietic growth factor, a colony stimulating factor (CSF), an interferon (IFN), erythropoietin, thrombopoietin and a combination thereof.

117. The targetable construct of embodiment 114, wherein said immunomodulator consists essentially of IL-1, IL-2, IL-3, IL-6, IL-10, IL-12, IL-18, IL-21, G-CSF, GM-CSF, interferon-γ, -α, -β or -γ, TNF-α, and "S1 factor.

118. The targetable construct of embodiment 114, wherein said oligonucleotide is an anti-sense oligonucleotide.

119. The targetable construct of embodiment 118, wherein said anti-sense oligonucleotide is bcl-2 or p53.

120. A solid support to which the targetable complex of embodiment 97 is bound.

121. A biosensor comprising the targetable complex of embodiment 97.

122. A targetable complex, said targetable complex comprising:

(A) a targetable construct comprising a molecular scaffold and X pairs of carrier epitopes, wherein each of said pairs of carrier epitopes is specifically bound by one of X bi-specific antibodies, each bi-specific antibody comprising (i) two copies of a first arm comprising a binding site for a carrier epitope, and (ii) two copies of a second arm comprising a binding site for one of Y target epitopes, and (B) X bi-specific antibodies;

wherein:

(1) X is a whole integer >3, (2) Y is a whole integer >1, (3) said X bi-specific antibodies can be the same or a mixture of different bi-specific antibodies, (4) said X pairs of carrier epitopes can be the same or a mixture of different carrier epitopes, and (5) when Y>2, said Y target epitopes can be the same or a mixture of different target epitopes;

wherein one or more of the following applies:

(a) said targetable complex has a Kd of from about 0.1 nM to about 100 nM for at least one of said target epitopes, (b) a pair of carrier epitopes is simultaneously bound by said two copies of a first arm comprising a binding site for said carrier epitope, wherein said two copies of a first arm comprising a binding site for said carrier epitope are part of said bi-specific antibody.

123. The targetable construct of embodiment 122, wherein said Kd for at least one of said target epitopes is from about 0.1 nM to 10 nM.

124. The targetable construct of embodiment 123, wherein said Kd for at least one of said target epitopes is from about 0.5 nM to about 5 nM.

125. The targetable construct of embodiment 124, wherein said Kd for at least one of target epitope is about 1 nM.

126. The targetable construct of embodiment 122, wherein said molecular scaffold is a peptide or peptide derivative.

127. The targetable construct of embodiment 122, wherein at least one of said carrier epitopes is a hapten.

128. The targetable construct of embodiment 122, wherein said targetable construct further comprises a bioactive moiety.

129. The targetable complex of embodiment 123, wherein said bioactive moiety is selected from the group consisting of a drug, a prodrug, an enzyme, a hormone, an immunomodulator, an oligonucleotide, a radionuclide, an image enhancing agent and a toxin.

130. The targetable construct of embodiment 129, wherein said enzyme is selected from the group consisting of malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

131. The targetable construct of embodiment 129, wherein said immunomodulator is selected from the group consisting of a cytokine, a stem cell growth factor, a lymphotoxin, a hematopoietic growth factor, a colony stimulating factor (CSF), an interferon (IFN), erythropoietin, thrombopoietin and a combination thereof.

132. The targetable construct of embodiment 129, wherein said immunomodulator consists essentially of IL-1, IL-2, IL-3, IL-6, IL-10, IL-12, IL-18, IL-21, G-CSF, GM-CSF, interferon-γ, -α, -β or -γ, TNF-α, and "S1 factor.

133. The targetable construct of embodiment 129, wherein said oligonucleotide is an anti-sense oligonucleotide.

134. The targetable construct of embodiment 133, wherein said anti-sense oligonucleotide is bcl-2 or p53.

135. A solid support to which the targetable construct of embodiment 122 is bound.

136. A biosensor comprising the targetable construct of embodiment 122.

137. The targetable construct or the targetable complex of any of embodiments 1, 31, 57, 72, 97 or 122, wherein said targetable construct or said targetable complex has a half-life in a defined set of conditions of from about 24 hours to about 500 days.

138. The targetable construct or the targetable complex of embodiment 137, wherein said targetable construct or said targetable complex has a half-life in a defined set of conditions of from about 24 hours to about 10 days.

139. The targetable construct or the targetable complex of embodiment 137, wherein said targetable construct or said targetable complex has a half-life in a defined set of conditions of from about 24 hours to about 72 hours.

140. The targetable construct or the targetable complex of embodiment 137, wherein said defined set of conditions is a set of physiological conditions.

141. The targetable construct or the targetable complex of embodiment 137, wherein said half-life in a defined set of conditions is a serum half-life in vitro.

142. The targetable construct or the targetable complex of any of embodiments 1, 31, 57, 72, 97 or 122, wherein said target epitope is associated with a hyperproliferative disease.

143. The targetable construct or targetable complex of embodiment 142, wherein said target epitope is a tumor associated antigen associated with a type of cancer selected from the group consisting of acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid, non-Hodgkin's lymphoma, ovarian cancer, pancreatic cancer, glioma, melanoma, liver cancer, prostate cancer, and urinary bladder cancer.

144. The targetable construct or targetable complex of embodiment 142, wherein said target epitope is a tumor associated antigen selected from the group consisting of A3, antigen specific for A33 antibody, BrE3, CD1, CD1a, CD3, CD5, CD15, CD19, CD20, CD21, CD22, CD23, CD25, CD30, CD45, CD74, CD79a, CD80, HLA-DR, NCA 95, NCA90, HCG and its subunits, CEA, CSAp, EGFR, EGP-1, EGP-2, Ep-CAM, Ba 733, HER2/neu, KC4, KS-1, KS1-4, Le-Y, MAGE, MUC1, MUC2, MUC3, MUC4, PAM-4, PSA, PSMA, RS5, S100, TAG-72, p53, tenascin, IL-6, insulin growth factor-1 (IGF-1), Tn antigen, Thomson-Friedenreich antigens, tumor necrosis antigens, VEGF, 17-1A, an angiogenesis marker, a cytokine, an immunomodulator, an oncogene marker, an oncogene product, and other tumor associated antigens.

145. A method of treating a hyperproliferative disease, comprising administering the targetable construct or targetable complex of embodiment 142 to a subject in need thereof.

146. The method of embodiment 148, further comprising administering at least one additional agent suitable for the treatment of said hyperproliferative disease.

147. The targetable construct or the targetable complex of any of embodiments embodiments 1, 31, 57, 72, 97 and 122, wherein said target epitope is associated with a diseased caused by a pathogen.

148. The targetable construct or targetable complex of embodiment 147, wherein said pathogen is selected from the group consisting of a bacterium, an intracellular pathogen, a fungus, a parasite and a virus.

149. The targetable construct or targetable complex of embodiment 147, wherein said pathogen is a bacteria selected from the group consisting of *Streptococcus agalactiae, Legionella pneumophilia, Streptococcus pyogenes, Escherichia coli, Salmonella typhimurium, Neisseria gonorrhoeae, Neisseria meningitidis, Pneumococcus* sp., *Hemophilis influenzae B, Yersina pestis, Mycobacteria* sp., *Mycobacterium leprae, Mycobacterium tuberculosis, Treponema pallidum, Pseudomonas aeruginosa, Francisella tularensis, Brucella* sp., *Brucella abortus, Bacillus anthracis, Clostridium botulinum*, and *Clostridium tetani.*

150. The targetable construct or targetable complex of embodiment 147, wherein said pathogen is an intracellular pathogen selected from the group consisting of *Chlamydia* sp., *Rickettsia* sp., *Leishmania* sp., *Kokzidioa* sp., *Borrelia burgdorfei, Plasmodia* sp., *Plasmodium falciparum, Trypanosoma* sp., *Trypanosoma brucei* and *Trypanosoma cruzi.*

151. The targetable construct or targetable complex of embodiment 147, wherein said pathogen is a fungus selected from the group consisting of *Candida* sp., *Candida albicans, Aspergillus* sp., *Mucor* sp., *Rhizopus* sp., *Fusarium* sp., *Peni-*

*cillium mameffei, Microsporum* sp., *Trichophyton mentagrophytes, Histoplasma capsulatum, Blastomyces dermatitidis* and *Coccidioides immitis.*

152. The targetable construct or targetable complex of embodiment 147, wherein said pathogen is a virus selected from the group consisting of hepatitis type A, hepatitis type B, hepatitis type C, influenza, varicella, adenovirus, HSV-I, HSV-II, rinderpest, rhinovirous, echovirus, rabies virus, Ebola virus, rotavirus, respiratory syncytial virus, papilloma virus, papova virus, CMV, echinovirus, arbovirus, huntavirus, coxsackie virus, mumps virus, measles virus, rubella virus, polio virus, HIV-I, HIV-II, Sendai virus, feline leukemia virus, Reovirus, poliovirus, human serum parvo-like virus, SV40, RSV, MMTV, Varicella-Zoster virus, Dengue virus, rubella virus, measles virus, adenovirus, human T-cell leukemia viruses, Epstein-Barr virus, murine leukemia virus, VSV, Variola virus, Sindbis virus, lymphocytic choriomeningitis virus, Rinderpest virus, wart virus and blue tongue virus.

153. A method of treating a pathogenic disease, comprising administering the targetable construct or targetable complex of embodiment 147 to a subject in need thereof.

154. A method for ablating non-malignant cells or tissue in a patient, said method comprising treating the patient with the targetable construct or targetable complex of any of embodiments 1, 26, 47, 57, 77 or 97, wherein said non-malignant cells or tissue are selected from the group consisting of ectopic tissue, retained tissue, normal organ tissue and bone marrow.

155. A method of treating a disease in a subject, comprising administering to said subject the targetable construct or targetable complex of any of embodiments 1, 31, 57, 72, 97 or 122, in an amount effective to modulate a biochemical process, wherein said target epitope is comprised within, displayed by or released from one or more cells, tissues, organs or systems of a subject comprising said disease.

156. The method of embodiment 155, wherein said bispecific antibody is a naked antibody.

157. The method of embodiment 155, wherein modulating said one or more biochemical processes causes, enhances, limits or prevents cellular quiescence, necrosis, apoptosis or a complement cascade, mutagenesis or carcinogenesis.

158. The targetable construct or the targetable complex of any of embodiments embodiments 1, 31, 57, 72, 97 or 122, wherein said target epitope is associated with a cardiovascular disorder.

159. A method of treating a cardiovascular disorder, comprising administering the targetable construct or targetable complex of embodiment 158 to a subject in need thereof.

160. The method of embodiment 159, further comprising administering at least one additional agent suitable for the treatment of said cardiovascular disorder.

161. The targetable construct or the targetable complex of any of embodiments embodiments 1, 31, 57, 72, 97 or 122, wherein said target epitope is associated with an autoimmune disorder.

162. A method of treating an autoimmune disorder, comprising administering the targetable construct or targetable complex of embodiment 161 to a subject in need thereof.

163. The method of embodiment 162, wherein autoimmune disorder is selected from the group consisting of acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, parnphigus vulgaris, Wegener's granulomatosis, membranous nephropathy, amyotrophic lateral sclerosis, tabes dorsalis, giant cell arteritis/polymyalgia, perniciousanemia, rapidly progressive glomerulonephritis and fibrosing alveolitis.

164. The method of embodiment 162, further comprising administering at least one additional agent suitable for the treatment of said hyperproliferative disease.

165. A pharmaceutical composition comprising the targetable construct or targetable complex of any of embodiments 1, 31, 57, 72, 97 or 122.

166. A method of treating a disease in a subject, comprising administering to said subject the pharmaceutical composition of embodiment 165.

167. A kit comprising the targetable construct or targetable complex of any of embodiments 1, 31, 57, 72, 97 or 122.

168. A method of detecting a substance in a sample, comprising contacting said sample with the targetable construct or targetable complex of any one of embodiments any of embodiments 1, 31, 57, 72, 97 or 122, wherein said substance is or comprises a target epitope.

169. A method of detecting a substance in a sample, wherein said substance is or comprises a target epitope, comprising contacting said sample with the biosensor of any of embodiments 1, 30, 56, 71, 96 or 121, and detecting a signal therefrom.

170. The method of embodiment 169, wherein said sample is a biological sample.

171. The method of embodiment 170, wherein said biological sample is selected from the group consisting of a sample of serum, blood, plasma, lymph, urine, feces, skin, intraocular fluid, synovial fluid, phlegm, cartilage and bone, and a biopsy sample.

172. A method of detecting a substance in an environment, wherein said substance is or comprises a target epitope, comprising exposing the biosensor of any of 1, 30, 56, 71, 96 or 121 to said environment, and detecting a signal therefrom.

173. A solid support comprising the targetable construct or targetable complex of any of embodiments 1, 31, 57, 72, 97 or 122.

174. The solid support of embodiment 173, wherein said solid support is selected from the group consisting of a dipstick, a bead, an interior surface of a well in a multiwell plate, and a membrane.

175. A method of purifying a substance, wherein said substance is or comprises a target epitope, said method comprising contacting a sample comprising said substance to the solid support of embodiment 173.

176. A method of detecting a substance in a sample, wherein said substance is or comprises a target epitope, said method comprising contacting said sample with the solid support of embodiment 173.

177. A dipstick comprising the solid support of embodiment 173.

178. A method of detecting a substance in a fluid sample, wherein said substance is or comprises a target epitope, said method comprising contacting said fluid sample with the dipstick of embodiment 177.

179. A multiwell plate comprising the targetable construct or targetable complex of any of embodiments 1, 31, 57, 72, 97 or 122.

180. A method of detecting a substance in a sample, wherein said substance is or comprises a target epitope, said method comprising contacting said sample with the multiwell plate of embodiment 179.

181. An immunoassay for a substance, wherein said substance is or comprises a target epitope, said method comprising contacting said substance with the multiwell plate of embodiment 179.

182. A membrane comprising the targetable construct or targetable complex of any of embodiments 1, 31, 57, 72, 97 or 122.

183. A method of detecting a substance, wherein said substance is or comprises a target epitope, said method comprising contacting said substance with the membrane of embodiment 182.

184. A bead comprising the targetable construct or targetable complex of any of embodiments 1, 31, 57, 72, 97 or 122.

185. A method of purifying a substance, wherein said substance is or comprises a target epitope, said method comprising contacting said substance with the bead of embodiment 184.

186. A method of binding a substance to a solid support, wherein said substance is or comprises a target epitope, said method comprising contacting said substance with the solid support of embodiment 173.

187. A method of removing all or some of a substance from a composition, wherein said substance is or comprises a target epitope, said method comprising contacting said composition with the solid support of embodiment 173.

188. The method of embodiment 187, wherein said composition is a fluid.

189. The method of embodiment 187, wherein said composition is a biological sample.

190. The method of embodiment 189, wherein said sample is a biological sample which is selected from the group consisting of serum, blood, plasma, lymph, urine, feces, sweat, intraocular fluid, semen, synovial fluid, mucus, exudent, bone marrow and a biopsy sample.

191. A method of removing all or some of a substance from a tissue in a patient, wherein said substance is or comprises a target epitope, said method comprising contacting said tissue with the solid support of embodiment 173 and reintroducing said tissue into said patient.

192. The method of embodiment 191, wherein said tissue is selected from the group consisting of serum, blood, plasma, lymph, intraocular fluid, bone marrow.

193. The method of embodiment 191, wherein said substance is or is part of a toxin, a pathogen, a hyperproliferative cell and an infected cell.

194. A device for treating a fluid of a patient in order to remove a substance therefrom and reintroducing said fluid into said patient, wherein said substance is or comprises a target epitope, said device comprising the solid support of embodiment 173.

195. A method of treating a patient, said method comprising removing a fluid from a patient, passing said fluid through the device of embodiment 194, and reintroducing said fluid into said patient.

196. The method of embodiment 187, further comprising separating said substance from said solid support.

197. The method of embodiment 187, wherein said substance is an undesirable substance.

198. The method of embodiment 187, wherein said substance is a compound of interest.

199. The method of embodiment 187, wherein said method is part of a manufacturing process.

200. The method of embodiment 159, wherein said cardiovascular disease is an atherosclerotic plaque, ischemia, fibrin clot, vascular clot, and myocardial infarction.

201. The method of embodiment 200, wherein said vascular clot is an embolus or thrombosis.

202. The method of embodiment 155, wherein said tissue is hypoplastic, absent, anatomically displaced or ectopic.

203. The method of embodiment 155, wherein said disease or disorder is a neurdegenerative or metabolic disease.

204. The method of embodiment 203, wherein said metabolic disease is amyloidosis and said targetable construct binds amyloid.

205. The method of embodiment 203, wherein said neurodegenerative disease is Alzheimer's disease.

206. A method of diagnosing/detecting a disease in a subject, comprising administering to said subject the targetable construct or targetable complex of any of embodiments 1, 31, 57, 72, 97 or 122, in an amount effective to modulate a biochemical process, wherein said target epitope is comprised within, displayed by or released from one or more cells, tissues, organs or systems of a subject comprising said disease.

207. The method of embodiment 206, wherein said method is suitable for detecting a cardiovascular lesion.

208. The method of embodiment 207, wherein said method is suitable for photodynamic diagnosis.

209. The method of embodiment 208, wherein said targetable construct comprises a photosensitizer selected from the group consisting of dihematoporphyrin, benzoporphyrin monoacid ring A, tin etiopurpurin, sulfonated aluminum phthalocyanine, and lutetium texaphyrin.

The invention claimed is:

1. A composition comprising a tetravalent targetable complex comprising the structure $(IgG1)_2$-$(scFv)_4$, wherein said tetravalent targetable complex is formed by linking two IgG1-$(scFv)_2$ molecules with a targetable construct comprising four DTPA (diethylenetriamine-pentaacetic acid) residues, wherein each IgG1-$(scFv)_2$ molecule comprises a pair of heavy chains and a pair of light chains, wherein each heavy chain comprises a humanized, chimeric or human IgG1 heavy chain and an scFv, wherein said scFv is fused to the C-terminus of said IgG1 heavy chain, wherein each scFv binds to a DTPA residue and wherein greater than 75% of the complexes in the composition have a stoichiometry of two molecules of IgG1-$(scFv)_2$ and one molecule of the targetable construct.

2. The composition according to claim 1, wherein each of said scFv molecules is murine or humanized.

3. The composition according to claim 1, wherein each IgG1 is an I253A human IgG1.

4. The composition according to claim 1, wherein said targetable complex further comprises a moiety selected from the group consisting of a drug, a prodrug, an enzyme, a hormone, an immunomodulator, an oligonucleotide, a radionuclide, an image enhancing agent and a toxin.

5. The composition according to claim 4, wherein said moiety is attached to the targetable construct.

6. The composition according to claim 4, wherein said enzyme is selected from the group consisting of malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

7. The composition according to claim 4, wherein said immunomodulator is selected from the group consisting of a cytokine, a stem cell growth factor, a lymphotoxin, a hematopoietic growth factor, a colony stimulating factor (CSF), an interferon (IFN), erythropoietin and thrombopoietin.

8. The composition according to claim 4, wherein said immunomodulator is selected from the group consisting of IL-1, IL-2, IL-3, IL-6, IL-10, IL-12, IL-18, IL-21, G-CSF, GM-CSF, interferon-γ, interferon-α, interferon-β, TNF-α and S1 factor.

9. The composition according to claim 4, wherein said drug is selected from the group consisting of doxorubicin, daunomycin, calicheamicin, maytansinoid, methotrexate, etoposide, CPT-11 and SN38.

10. The composition according to claim 4, wherein said radionuclide is selected from the group consisting of Ac-225, Ag-111, As-77, At-211, At-217, Au-198, Au-199, Bi-211, Bi-212, Bi-213, Br-80m, Co-58, Cu-64, Cu-67, Dy-152, Er-169, Fe-59, Fm-255, Fr-221, Ga-67, Ho-161, Ho-166, I-125, I-131, In-111, Ir-192, Ir-194, Lu-177, Mo-99, Os-189m, P-32, P-33, Pb-211, Pb-212, Pd-109, Pm-149, Po-215, Pr-142, Pr-143, Pt-109, Ra-223, Re-186, Re-188, Re-189, Rh-103m, Rh-105, Rn-219, Sb-119, Sc-47, Se-75, Sm-153, Sr-89, Tb-161, Tc-99m and Y-90.

11. The composition according to claim 1, wherein each IgG binds to a tumor-associated antigen selected from the group consisting of A3, CD1, CD1a, CD3, CD5, CD15, CD19, CD20, CD21, CD22, CD23, CD25, CD30, CD33, CD45, CD74, CD79a, CD80, NCA90, NCA95, HLA-DR, CEA, CSAp, EGFR, EGP-1, EGP-2, Ep-CAM, Ba 733, HER2/neu, KC4, KS-1, KS1-4, Le-Y, S100, MAGE, MUC1, MUC2, MUC3, MUC4, PSA, PSMA, AFP, HCG, RS5, TAG-72, tenascin, IL-6, IL-2 receptor, insulin-like growth factor-1 (IGF-1), Tn antigen, Thomson-Friedenreich antigens, tumor necrosis antigens, VEGF, 17-1A, an angiogenesis marker, a cytokine, an immunomodulator and an oncogene product.

12. The composition of claim 1, wherein the targetable complex is constructed with two IgG1 antibodies having the same specificity.

13. The composition of claim 1, wherein the targetable complex is constructed with two IgG1 antibodies having different specificities.

14. The composition according to claim 1, wherein said composition is a pharmaceutical composition.

* * * * *

SEQUENCE LISTING

<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (2)..(2)
<223> OTHER INFORMATION: Lys(diethylenetriaminepentaacetic acid)

```
<220> FEATURE:
<221> NAME/KEY: MOD_RES
<222> LOCATION: (4)..(4)
<223> OTHER INFORMATION: Lys(diethylenetriaminepentaacetic acid)
<220> FEATURE:
<223> OTHER INFORMATION: C-term amidated

<400> SEQUENCE: 1

Phe Lys Tyr Lys
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Lys Tyr Lys
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (1,4,7,10-tetraazacyclododecanetetraacetic
      acid)Phe
<220> FEATURE:
<221> NAME/KEY: MOD_RES
<222> LOCATION: (2)..(2)
<223> OTHER INFORMATION: Lys(histamine succinyl glycyl)
<220> FEATURE:
<221> NAME/KEY: MOD_RES
<222> LOCATION: (4)..(4)
<223> OTHER INFORMATION: Lys(histamine succinyl glycyl)
<220> FEATURE:
<223> OTHER INFORMATION: C-term amidated

<400> SEQUENCE: 3

Phe Lys Tyr Lys
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Lys(diethylenetriaminepentaacetic acid)
<220> FEATURE:
<221> NAME/KEY: MOD_RES
<222> LOCATION: (3)..(3)
<223> OTHER INFORMATION: Lys(diethylenetriaminepentaacetic acid)
<220> FEATURE:
<221> NAME/KEY: MOD_RES
<222> LOCATION: (5)..(5)
<223> OTHER INFORMATION: Thiosemicarbazonylglyoxyl-Cys
<220> FEATURE:
<223> OTHER INFORMATION: C-term amidated
```

-continued

```
<400> SEQUENCE: 4

Lys Tyr Lys Lys Cys
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (4)..(4)
<223> OTHER INFORMATION: Lys(diethylenetriaminepentaacetic acid)
<220> FEATURE:
<223> OTHER INFORMATION: C-term amidated

<400> SEQUENCE: 5

Phe Gln Tyr Lys
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (2)..(2)
<223> OTHER INFORMATION: Lys(diethylenetriaminepentaacetic acid)
<220> FEATURE:
<221> NAME/KEY: MOD_RES
<222> LOCATION: (4)..(4)
<223> OTHER INFORMATION: Lys(diethylenetriaminepentaacetic acid)
<220> FEATURE:
<223> OTHER INFORMATION: C-term amidated

<400> SEQUENCE: 6

Cys Lys Tyr Lys
1
```